US 7,163,791 B2

(12) United States Patent
Sasaki et al.

(10) Patent No.: US 7,163,791 B2
(45) Date of Patent: Jan. 16, 2007

(54) α,2,8-SIALYLTRANSFERASE

(75) Inventors: Katsutoshi Sasaki, Tokyo (JP);
Kazumi Miura, Kanagawa (JP); Nobuo Hanai, Kanagawa (JP); Tatsunari Nishi, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 238 days.

(21) Appl. No.: 10/430,325

(22) Filed: May 7, 2003

(65) Prior Publication Data

US 2004/0002138 A1    Jan. 1, 2004

Related U.S. Application Data

(60) Division of application No. 08/361,304, filed on Nov. 29, 1994, now Pat. No. 6,596,523, which is a continuation-in-part of application No. PCT/JP94/00495, filed on Mar. 28, 1994.

(30) Foreign Application Priority Data

Mar. 29, 1993  (JP) .................................. 5-69988

(51) Int. Cl.
 C12N 15/54    (2006.01)
 C12N 15/63    (2006.01)
 C12N 1/21     (2006.01)
 C12Q 1/68     (2006.01)
 C12N 9/10     (2006.01)

(52) U.S. Cl. .................. 435/6; 435/320.1; 435/440; 435/91.4; 435/193; 435/325; 435/252.3; 435/252.33; 536/23.2

(58) Field of Classification Search ............ 435/320.1, 435/440, 91.4, 193, 325, 6, 252.3, 252.33; 536/23.2
See application file for complete search history.

(56) References Cited

U.S. PATENT DOCUMENTS 5,324,663 A * 6/1994 Lowe ..................... 435/320.1

OTHER PUBLICATIONS

S. Ohta et al. "Antitumor Effects of a Novel Monoclonl Antibody With high Binding Affinity to Ganglioside GD3", Cancer Immunol. Immunother. 36: 260-266. (1993).*
Yoshida, et al., The Journal of Biological Chemistry, vol. 270, No. 24, Issue of Jun. 16, pp. 14628-14633, 1996, Molecular Cloning of Siaα2,3Galβ1,4GlcNAc α2,8-Sialyltransferase from Mouse Brain.
Paulson, et al., The Journal of Biological Chemistry, vol. 252, No. 7, Issue of Apr. 10, pp. 2356-2362, 1977, Purification of Sialyltransferase from Bovine Colostrum by Affinity Chromatography on CDP-agarose.
Weinstein, et al., The Journal of Biological Chemistry, vol. 257, No. 22, Issue of Nov. 25, pp. 13835-13844, 1982, Purification of a Galβ1→A4GlcNAc α2→6 Sialyltransferase and a Galβ1→3(4)G1cNAc α2→3.

Sadler, et al., The Journal of Biological Chemistry, vol. 254, No. 11, Issue of Jun. 10, pp. 4434-4443, 1979, Purification to Homogeneity of a β-Galactoside α2→3 Sialyltransferase and Partial Purification of an α-N-Acetylgalactosaminide α2→6 Sialyltransferase from Porcine Submaxillary Glands.
Rosenberg, et al., Enzymatic Basis for Increased Expression of GD3 on Human Melanoma Cells Derived from Metastatic Lesions, Journal of Clinical Laboratory Analysis, vol. 2, No. 2, 1988, pp. 91-100.
Thampoe, et al., Sialyltransferase Levels and Ganglioside Expression in Melanoma and Other Cultured Human Cancer Cells, Cancer Res. 49(22) 6258-6264 (1989).
Gu, et al., Purification to Homogeneity of GD3 Synthase and Partial Purification of GM3 Synthase From Rat Brain, Biochem. Biophys. Res. Commun. 166(1) 387-383.
Nara, et al., Expression Cloning of a CMP-NeuAc:NeuAcalpha2-3Galbeta 1-4Glcbeta1-1'Ceralpha2,8-Sialyltransferase (GD3 Synthase) From Human Melanoma Cells), Proc. Natl. Acad. Sci. 91(17) 7952-7956 (Aug. 1994).
Sasaki, et al., Expression Cloning of a GM3-Specific Alpha-2,8-Sialyltransferase (GD3 Synthase), J. Biol. Chem. 269(22) 15950-15956 (Jun. 1994).
Haraguchi, et al., Isolation of GD3 Synthase Gene by Expression Cloning of GM3 Alpha-2,8-Sialyltransferase cDNA Using Anti-GD2 Monoclonal Antibody, Proc. Natl. Acad. Sci. 91(22)10455-10459 (Oct. 1994).
Grundmann, et al., Complete cDNA Sequence Encoding Human β-Galatoside Alpha-2,6-Sialyltransferase, Nuc. Acids Res. 18(3) 667 (1990).
Agostaro, et al., Cloning of cDNA Encoding the Membrane-Bound Form of Bovine β1,4-Galactosyltransferase, Eur. J. Biochem. 183: 211-217 (1989).
Sakar, et al., Molecular Cloning and Expression of cDNA Encoding the Enzyme that Controls Conversion of High-Mannose to Hybrid and Complex N-glycans: UDP-N-Acetylglucosamine: Alpha-3-D-Mannoside β-1,2-N-Acetyglucosaminyltransferase 1, PNAS 88: 234-238 (Jan. 1991).
Sadler, et al., JBC, vol. 254, No. 13, Jul. 10, pp. 5934-5941, 1979 Purification to homogeneity and Enzymatic Characterization of an α-N-Acetylgalactosaminide α2→6 Sialyltransferase from Porcine Submaxillary Glands.
Yamashiro et al (Cancer Research 53:5395-5400 (1993)).
Weisgerber (Glycobiology 1(4):357-365 (1991)).

* cited by examiner

*Primary Examiner*—Rebecca Prouty
(74) *Attorney, Agent, or Firm*—Nixon & Vanderhye P.C.

(57) ABSTRACT

The invention provides a novel α-2,8-sialyltransferase expressed by a gene cloned from animal cells, a cDNA coding for the α-2,8-sialyltransferase, a method of detecting, or suppressing the production of α-2,8-sialyltransferase by using the cDNA, a recombinant vector containing the DNA as an insert and cells harboring the recombinant vector as well as methods of preparing same. The α-2,8-sialyltransferase of the invention is useful, for example, in the production of carbohydrate chains having a useful physiological activity, for example the ganglioside GD3, and modifications thereof.

11 Claims, 24 Drawing Sheets

StuI partial digestion

BamHI linker
(5' pCCGGATCCGG 3')

BamHI

T4-DNA ligase

BalI

ScaI linker
(5' pAAGTACTT 3')

T4-DNA ligase ural structure is maintained.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 2117
      (B) TYPE: nucleic acid
      (C) STRANDEDNESS: double
      (D) TOPOLOGY: linear (ii) MOLECULE TYPE: cDNA to mRNA (vi) ORIGINAL SOURCE:
      (A) ORGANISM: Homo sapiens
      (B) STRAIN: WM266-4 cell
      (G) CELL TYPE: melanoma -continued (xi) SEQUENCE DESCRIPTION: SEQ ID NO: 1:

```
GGGGGGGGTT GCCTGGCGGC GCAGCAGCGC GGGAGGCGGC GAAGGGCGCA GGAGCATCGC    60

TCGGAGGGGA CAAGGGGACG CCACGGGCCA CATGTTTAGG AGGGAGCCGA GCCTTCTCCC   120

GGACCCTCGC CGAGGGCGAC CGTGATGCTG CAGAACCGGC GGGAGCGACT CGCCGCCGCC   180

GCTCTCTGCG CACTCGGAGA CCCCAGCGCC CGCCTTCTGC AGGGGAAGCG ACCATGGCCA   240

TAGATCGTGA CTTCACCCCC AGCCACTTCC CCTAGAAAGA AATCCTTGGA AAAGTTGCAT   300

TTGAAAAAAT CCTTGCGCTG ACCTTTGGGG CCGACGGGGC CGAAGAAGCG TGCGTGCGTT   360

TGCAAGTAAG AGAACCAAAG GTGTGTGTGC ATGGGGGGCT GGCGGTGGGG GACCCTCCGC   420

TGCCACTTCG CCTAGCTTTG TGCTGAGGCC CCGGCCCCCG CCCCTGGGAC GCCGGGGCTG   480
```

```
CG ATG AGC CCC TGC GGG CGG GCC CGG CGA CAA ACG TCC AGA GGG GCC       527
   Met Ser Pro Cys Gly Arg Ala Arg Arg Gln Thr Ser Arg Gly Ala
   1               5                  10                  15

ATG GCT GTA CTG GCG TGG AAG TTC CCG CGG ACC CGG CTG CCC ATG GGA     575
Met Ala Val Leu Ala Trp Lys Phe Pro Arg Thr Arg Leu Pro Met Gly
                20                  25                  30

GCC AGT GCC CTC TGT GTC GTG GTC CTC TGT TGG CTC TAC ATC TTC CCC     623
Ala Ser Ala Leu Cys Val Val Val Leu Cys Trp Leu Tyr Ile Phe Pro
                35                  40                  45

GTC TAC CGG CTG CCC AAC GAG AAA GAG ATC GTG CAG GGG GTG CTG CAA     671
Val Tyr Arg Leu Pro Asn Glu Lys Glu Ile Val Gln Gly Val Leu Gln
            50                  55                  60

CAG GGC ACG GCG TGG AGG AGG AAC CAG ACC GCG GCC AGA GCG TTC AGG     719
Gln Gly Thr Ala Trp Arg Arg Asn Gln Thr Ala Ala Arg Ala Phe Arg
        65                  70                  75

AAA CAA ATG GAA GAC TGC TGC GAC CCT GCC CAT CTC TTT GCT ATG ACT     767
Lys Gln Met Glu Asp Cys Cys Asp Pro Ala His Leu Phe Ala Met Thr
    80                  85                  90                  95

AAA ATG AAT TCC CCT ATG GGG AAG AGC ATG TGG TAT GAC GGG GAG TTT     815
Lys Met Asn Ser Pro Met Gly Lys Ser Met Trp Tyr Asp Gly Glu Phe
                100                 105                 110

TTA TAC TCA TTC ACC ATT GAC AAT TCA ACT TAC TCT CTC TTC CCA CAG     863
Leu Tyr Ser Phe Thr Ile Asp Asn Ser Thr Tyr Ser Leu Phe Pro Gln
            115                 120                 125

GCA ACC CCA TTC CAG CTG CCA TTG AAG AAA TGC GCG GTG GTG GGA AAT     911
Ala Thr Pro Phe Gln Leu Pro Leu Lys Lys Cys Ala Val Val Gly Asn
        130                 135                 140

GGT GGG ATT CTG AAG AAG AGT GGC TGT GGC CGT CAA ATA GAT GAA GCA     959
Gly Gly Ile Leu Lys Lys Ser Gly Cys Gly Arg Gln Ile Asp Glu Ala
    145                 150                 155

AAT TTT GTC ATG CGA TGC AAT CTC CCT CCT TTG TCA AGT GAA TAC ACT    1007
Asn Phe Val Met Arg Cys Asn Leu Pro Pro Leu Ser Ser Glu Tyr Thr
160                 165                 170                 175

AAG GAT GTT GGA TCC AAA AGT CAG TTA GTG ACA GCT AAT CCC AGC ATA    1055
Lys Asp Val Gly Ser Lys Ser Gln Leu Val Thr Ala Asn Pro Ser Ile
                180                 185                 190

ATT CGG CAA AGG TTT CAG AAC CTT CTG TGG TCC AGA AAG ACA TTT GTG    1103
Ile Arg Gln Arg Phe Gln Asn Leu Leu Trp Ser Arg Lys Thr Phe Val
            195                 200                 205

GAC AAC ATG AAA ATC TAT AAC CAC AGT TAC ATC TAC ATG CCT GCC TTT    1151
Asp Asn Met Lys Ile Tyr Asn His Ser Tyr Ile Tyr Met Pro Ala Phe
        210                 215                 220

TCT ATG AAG ACA GGA ACA GAG CCA TCT TTG AGG GTT TAT TAT ACA CTG    1199
Ser Met Lys Thr Gly Thr Glu Pro Ser Leu Arg Val Tyr Tyr Thr Leu
    225                 230                 235
```

```
TCA GAT GTT GGT GCC AAT CAA ACA GTG CTG TTT GCC AAC CCC AAC TTT      1247
Ser Asp Val Gly Ala Asn Gln Thr Val Leu Phe Ala Asn Pro Asn Phe
240                 245                 250                 255

CTG CGT AGC ATT GGA AAG TTC TGG AAA AGT AGA GGA ATC CAT GCC AAG      1295
Leu Arg Ser Ile Gly Lys Phe Trp Lys Ser Arg Gly Ile His Ala Lys
                260                 265                 270

CGC CTG TCC ACA GGA CTT TTT CTG GTG AGC GCA GCT CTG GGT CTC TGT      1343
Arg Leu Ser Thr Gly Leu Phe Leu Val Ser Ala Ala Leu Gly Leu Cys
                275                 280                 285

GAA GAG GTG GCC ATC TAT GGC TTC TGG CCC TTC TCT GTG AAT ATG CAT      1391
Glu Glu Val Ala Ile Tyr Gly Phe Trp Pro Phe Ser Val Asn Met His
                290                 295                 300

GAG CAG CCC ATC AGC CAC CAC TAC TAT GAC AAC GTC TTA CCC TTT TCT      1439
Glu Gln Pro Ile Ser His His Tyr Tyr Asp Asn Val Leu Pro Phe Ser
305                 310                 315

GGC TTC CAT GCC ATG CCC GAG GAA TTT CTC CAA CTC TGG TAT CTT CAT      1487
Gly Phe His Ala Met Pro Glu Glu Phe Leu Gln Leu Trp Tyr Leu His
320                 325                 330                 335

AAA ATC GGT GCA CTG AGA ATG CAG CTG GAC CCA TGT GAA GAT ACC TCA      1535
Lys Ile Gly Ala Leu Arg Met Gln Leu Asp Pro Cys Glu Asp Thr Ser
                340                 345                 350

CTC CAG CCC ACT TCC TAG GAACAATGGA AGAAGAAAGG ACTGAACCAG             1583
Leu Gln Pro Thr Ser TER
                355

GGTATTTTTG TTAGGTTTTC TATGTGACTC CAAGAGGGAA TGGTCAAGTT GTTTCATGAG    1643

TTTGCATGGG CCCTTGGAAA AACAGGAAAG GAGCAATGAA GATCCAAGCA AAACTTTACT    1703

TTCAGCGTTG GCTTGGAGGA CAAATAAGAA ATGAAACATC CTATGAAATA CTTTATAGCA    1763

CATGGCAGAT TTGCAACTAG TAAAATGCTG GTGAAATGCT GTTGGTAAAG CACATGGTTC    1823

AAATCTAGAA GATGCAGTTC AAAAACAAGA CAGACTCGAG TTGTTAGGGC TGAGGAACCA    1883

ATCAAGGTAG AACAAAGAAA ATGTTGGGGT AAAAGTGTTG CTGATTGTCA ACACAAACTG    1943

GCTTAATAAT ATTAATAAGA ACCTGTCTTA TTAAGACTGG CTTTAGAACC GTAGGTTTTT    2003

TTAAAAAATT ATTATTTATT TTTGCCCTCT TTGGGGAAGT GGGTGGGTAG ATTTAAAAAA    2063

TCCCTTCCTG AGTAATAAAG ATACAAAATG TTACTGCTGA TAAAAAAAAA AAAA          2117

(2) INFORMATION FOR SEQ ID NO: 2:

(i) SEQUENCE CHARACTERISTICS:
        (A) LENGTH: 356
        (B) TYPE: amino acid
        (D) TOPOLOGY: linear (ii) MOLECULE TYPE: protein (vi) ORIGINAL SOURCE:
        (A) ORGANISM: Homo sapiens
        (B) STRAIN: WM266-4 cell
        (G) CELL TYPE: melanoma (xi) SEQUENCE DESCRIPTION: SEQ ID NO: 2:

Met Ser Pro Cys Gly Arg Ala Arg Arg Gln Thr Ser Arg Gly Ala
1               5                   10                  15

Met Ala Val Leu Ala Trp Lys Phe Pro Arg Thr Arg Leu Pro Met
                20                  25                  30

Gly Ala Ser Ala Leu Cys Val Val Val Leu Cys Trp Leu Tyr Ile
                35                  40                  45

Phe Pro Val Tyr Arg Leu Pro Asn Glu Lys Glu Ile Val Gln Gly
                50                  55                  60
```

-continued

```
Val Leu Gln Gln Gly Thr Ala Trp Arg Arg Asn Gln Thr Ala Ala
                65                  70                  75

Arg Ala Phe Arg Lys Gln Met Glu Asp Cys Cys Asp Pro Ala His
                80                  85                  90

Leu Phe Ala Met Thr Lys Met Asn Ser Pro Met Gly Lys Ser Met
                95                 100                 105

Trp Tyr Asp Gly Glu Phe Leu Tyr Ser Phe Thr Ile Asp Asn Ser
               110                 115                 120

Thr Tyr Ser Leu Phe Pro Gln Ala Thr Pro Phe Gln Leu Pro Leu
               125                 130                 135

Lys Lys Cys Ala Val Gly Asn Gly Ile Leu Lys Ser
               140                 145                 150

Gly Cys Gly Arg Gln Ile Asp Glu Ala Asn Phe Val Met Arg Cys
               155                 160                 165

Asn Leu Pro Pro Leu Ser Ser Glu Tyr Thr Lys Asp Val Gly Ala
               170                 175                 180

Lys Ser Gln Leu Val Thr Ala Asn Pro Ser Ile Ile Arg Gln Arg
               185                 190                 195

Phe Gln Asn Leu Leu Trp Ser Arg Lys Thr Phe Val Asp Asn Met
               200                 205                 210

Lys Ile Tyr Asn His Ser Tyr Ile Tyr Met Pro Ala Phe Ser Met
               215                 220                 225

Lys Thr Gly Thr Glu Pro Ser Leu Arg Val Tyr Tyr Thr Leu Ser
               230                 235                 240

Asp Val Gly Ala Asn Gln Thr Val Leu Phe Ala Asn Pro Asn Phe
               245                 250                 255

Leu Arg Ser Ile Gly Lys Phe Trp Lys Ser Arg Gly Ile His Ala
               260                 265                 270

Lys Arg Leu Ser Thr Gly Leu Phe Leu Val Ser Ala Ala Leu Gly
               275                 280                 285

Leu Cys Glu Glu Val Ala Ile Tyr Gly Phe Trp Pro Phe Ser Val
               290                 295                 300

Asn Met His Glu Gln Pro Ile Ser His His Tyr Tyr Asp Asn Val
               305                 310                 315

Leu Pro Phe Ser Gly Phe His Ala Met Pro Glu Glu Phe Leu Gln
               320                 325                 330

Leu Trp Tyr Leu His Lys Ile Gly Ala Leu Arg Met Gln Leu Asp
               335                 340                 345

Pro Cys Glu Asp Thr Ser Leu Gln Pro Thr Ser
               350                 355 356
```

(2) INFORMATION FOR SEQ ID NO: 3:

(i) SEQUENCE CHARACTERISTICS:
        (A) LENGTH: 52
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO: 3:

TCGACAAGCT TGATATCGGC CTGTGAGGCC TCACTGGCCG CGGCCGCGGT AC      52

(2) INFORMATION FOR SEQ ID NO: 4:

(i) SEQUENCE CHARACTERISTICS:

-continued

```
    (A) LENGTH: 44
    (B) TYPE: nucleic acid
    (C) STRANDEDNESS: double
    (D) TOPOLOGY: linear (ii) MOLECULE TYPE: other nucleic acid, synthetic DNA (xi) SEQUENCE DESCRIPTION: SEQ ID NO: 4:

GTTCGAACTA TAGCCGGACA CTCCGGAGTG ACCGGCGCCG GCGC            44

(2) INFORMATION FOR SEQ ID NO: 5:

(i) SEQUENCE CHARACTERISTICS:
        (A) LENGTH: 11
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO: 5:

CTTTAGAGCA C                                                11

(2) INFORMATION FOR SEQ ID NO: 6:

(i) SEQUENCE CHARACTERISTICS:
        (A) LENGTH: 36
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO: 6:

CTCTCGGATA TCCGATCGTG CAGGGGGTGC TGCAAC                     36

(2) INFORMATION FOR SEQ ID NO: 7:

(i) SEQUENCE CHARACTERISTICS:
        (A) LENGTH: 37
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO: 7:

GTCAACGGTA CCTTCCTAGG AAGTGGGCTG GAGTGAG                    37
```

α,2,8-SIALYLTRANSFERASE

The present application is a divisional of application Ser. No. 08/361,304, filed Nov. 29, 1994 now U.S. Pat. No. 6,596,523, which is a CIP of PCT/JP94/00495, filed Mar. 28, 1994.

FIELD OF THE INVENTION

The present invention relates to α-2,8-sialyltransferase, a cDNA coding for the α-2,8-sialyltransferase, a recombinant vector containing the cDNA as an insert and a cell harboring the recombinant vector as well as methods of producing same. The invention further relates to a method of producing carbohydrate chains using the α-2,8-sialyltransferase and to a method of producing carbohydrate chains through production of the α-2,8-sialyltransferase in transformant cells. Still further, it relates to a method of detecting the α-2,8-sialyltransferase and a method of inhibiting the production of the α-2,8-sialyltransferase, each using DNA coding for the α-2,8-sialyltransferase of the invention. The α-2,8-sialyltransferase of the invention is useful, in particular, in the production of carbohydrate chains having a useful physiological activity, for example the ganglioside GD3, and modifications thereof.

BACKGROUND ART

While proteins produced in prokaryotes, for example *Escherichia coli*, have no carbohydrate chain, proteins and lipids produced in eukaryotes such as yeast, fungi, plant cells and animal cells have a carbohydrate chain bound thereto in many instances.

Carbohydrate chains bound to proteins in animal cells include N-glycoside bond type carbohydrate chains (also called N-glycans) bound to an asparagine (Asn) residue in the protein and O-glycoside bond type carbohydrate chains (also called O-glycans) bound to a serine (Ser) or threonine (Thr) residue. It has recently been revealed that a certain kind of lipid containing a carbohydrate chain is covalently bound to a number of proteins and that those proteins are attached to the cell membrane through the lipid. This carbohydrate chain-containing lipid is called glycosyl phosphatidylinositol anchor.

Other carbohydrate chains, including glycosaminoglycans, are also present in animal cells. Compounds comprising a protein covalently bound to a glycosaminoglycan are called proteoglycans. The glycosaminoglycans of the carbohydrate chains of proteoglycans are similar in structure to O-glycans, which are carbohydrate chains of glycoproteins, but differ chemically therefrom. Glycosaminoglycans comprise repeating disaccharide units composed of glucosamine or galactosamine and a uronic acid (except for keratan sulfate which has no uronic acid residue) and have a covalently bound sulfate residue (except for hyaluronic acid which has no sulfate residue).

Further, carbohydrate chains in animal cells are also present in substances called glycolipids. Sphingoglycolipids are one type of glycolipid present in animal cells. Sphingoglycolipids are composed of a carbohydrate, a long-chain fatty acid and sphingosine, a long-chain base, covalently bound together. Glyceroglycolipids are composed of a carbohydrate chain and glycerol covalently bound together.

Recent advances in molecular biology and cellular biology have made it possible to clarify the functions of carbohydrate chains. To date, a variety of functions of carbohydrate chains have been elucidated. First, carbohydrate chains play an important role in the clearance of glycoproteins in blood. It is known that erythropoietin produced by introducing the relevant gene into *Escherichia coli* retains activity in vitro but undergoes rapid clearance in vivo [Dordal et al.: Endocrinology, 116, 2293 (1985) and Browne et al.: Cold Spring Harbor Symposia on Quantitative Biology, 51, 693 (1986)]. It is known that while native human granulocyte-macrophage colony stimulating factor (hGM-CSF) has two carbohydrate chains of the N-glycoside bond type, a reduction in the number of carbohydrate chains results in a proportional increase in the rate of clearance in rat plasma [Donahue et al.: Cold Spring Harbor Symposia on Quantitative Biology, 51, 685 (1986)]. The rate of clearance and the site of clearance may vary or differ depending on the structure of the carbohydrate chain in question. For example, it is known that hGM-CSF having a sialic acid residue undergoes clearance in the kidney while hGM-CSF deprived of sialic acid shows an in creased rate of clearance and undergoes clearance in the liver. Alpha1-acid glycoproteins differing in carbohydrate structure and biosynthesized in the presence of various N-glycoside type carbohydrate chain biosynthesis inhibitors using a rat liver primary culture system were studied with respect to their rate of clearance from rat plasma and their rate of clearance from rat perfusate. In both cases, the rate of clearance was reduced in the order: high mannose type, carbo hydrate chain-deficient type, hybrid type and composite type (natural type). It is known that the clearance from blood of tissue-type plasminogen activator (t-PA), which is used medicinally as a thrombolytic agent, is greatly influenced by the structure of its carbohydrate chain.

It is known that carbohydrate chains give protease resistance to proteins. For example, when carbo hydrate formation on fibronectin is inhibited with tunicamycin, the rate of degradation of intracellular carbohydrate chain-deficient fibronectin increases. It is also known that addition of a carbohydrate chain may result in increased heat stability or freezing resistance. In the case of erythropoietin and β-interferon, among others, the carbohydrate chain is known to contribute to increased solubility of the protein.

Carbohydrate chains also serve to maintain protein tertiary structure. It is known that when the membrane binding protein of vesicular stomatitis virus is devoid of the two naturally-occurring N-glycoside bond type carbohydrate chains, transport of the protein to the cell surface is inhibited and that when new carbohydrate chains are added to the protein, it is transported. It was revealed that, in that case, intermolecular association of the protein through disulfide bonding is induced following the elimination of carbohydrate chains and, as a result, protein transport is inhibited. When carbohydrate chains are added, association is inhibited, and the proper tertiary protein structure is maintained and protein transport becomes possible. As regards the site of addition of the new carbohydrate, it has been shown that there is a considerable amount of flexibility. In contrast, it has also been shown in certain instances that, depending on the site of carbohydrate chain introduction, the transport of a protein having a natural carbohydrate chain or chains may be completely inhibited.

Examples are also known where a carbohydrate chain serves to mask an antigenic site of a poly peptide. In the case of hGM-CSF, prolactin, inter feron-γ, Rauscher leukemia virus gp70 and influenza hemagglutinin, experiments using a polyclonal antibody or a monoclonal antibody to a specific site on the peptide suggest that carbohydrate chains of these proteins inhibit antibody binding. Cases are also known where carbohydrate chains themselves are directly involved in the expression of activity by aglyco protein. For instance, carbohydrates are thought to be associated with the expression of activity of such glycoprotein hormones as luteinizing hormone, follicle stimulating hormone and chorionic gonadotropin.

Carbohydrate chains serve an important function in the phenomenon of recognition between cells, between proteins or between a cell and a protein. For example, it is known that structurally different carbohydrate chains undergo clearance in vivo at different sites. It has recently been revealed that the ligand of the protein ELAM-1, which is expressed specifically on vascular endothelial cells during an inflammatory response and promotes adhesion to neutrophils, is a carbohydrate chain called sialyl Lewis x [NeuAcα2-3Galβ1-4(Fucα1-3)GlcNAc; where NeuAc: sialic acid; Gal: galactose; Fuc: fucose; GlcNAc: N-acetylglucosamine]. The possibile use of carbohydrate chains themselves or modifications thereof as drugs or the like is thus suggested [Phillips et al.: Science, 250, 1130 (1990); Goelz et al.: Trends in Glycoscience and Glycotechnology, 4, 14 (1992)]. Like ELAM-1, L-selectin, expressed in some T lymphocytes or neutrophils, and GMP-140 (also called P-selectin), expressed in platelets or on the membrane surface of vascular endothelial cells upon inflammatory stimulation, are associated with inflammatory responses. It is suggested that their ligand may be a carbohydrate chain analogous to sialyl Lewis x, the ELAM-1 ligand [Rosen et al.: Trends in Glycoscience and Glycotechnology, 4, 1 (1992); Larsen et al.: Trends in Glycoscience and Glycotechnology, 4, 25 (1992); Aruffo et al.: Trends in Glycoscience and Glycotechnology, 4, 146 (1992)].

It has been suggested that, in cancer metastatis, as in inflammatory responses, ELAM-1 and GMP-140 cause adhesion of cancer cells to the vascular endothelium or aggregation of cancer cells with platelets and thereby promote cancer metastatis [Goelz et al.: Trends in Glycoscience and Glycotechnology, 4, 14 (1992); Larsen et al.: Trends in Glycoscience and Glycotechnology, 4, 25 (1992)]. This is in agreement with the finding that the level of expression of the sialyl Lewis x carbohydrate chain is high in cancer cells that are highly metastatic [Irimura et al.: Jikken Igaku (Experimental Medicine), 6, 33 (1988)].

Gangliosides constitute a group of cell membrane constituent glycolipids. They are molecules composed of a sialic acid residue-containing carbohydrate chain, which is a hydrophilic side chain, sphingosine, which is a hydrophobic side chain, and a fatty acid. It is known not only that the expression of gangliosides varies with the cell, organ and animal species but also that gangliosides undergo quantitative and qualitative changes during the process of cell differentiation or oncogenesis [Hakomori: Cancer Research, 45, 2405 (1985)]. Scores of gangliosides have been discovered so far, including GM3 which is expressed in a variety of normal cells, and gangliosides occurring in extremely small amounts [Wiegant: Gangliosides and Cancer, Verlagsgesellschaft, 1989, pages 5–15]. GD3, for example, occurs in small amounts in normal tissues but it is expressed at high levels in neuroectodermal tumors, such as malignant melanoma. It is therefore believed to be a type of cancer antigen [Tsuchida et al.: Journal of the National Cancer Institute, 78, 45–54 (1987)]. A recent report shows that the proportions of GD3 and GM3 vary according to the degree of malignancy of malignant melanoma [Ravindranath et al.: Cancer, 67, 3029 (1991)] and it is widely known that GD3 is an important cancer antigen. Furthermore, it has been demonstrated that the expression of GD3 is induced in cells into which an oncogene has been introduced, supporting the close relation between cell transformation and GD3 expression [Sanai et al.: Journal of Biochemistry, 107, 740–742 (1990)]. As for the functions of GD3, it has been suggested that it plays an important role in adhesion of cancer cells to extracellular substrates [Burns et al.: Journal of Cell Biology, 107, 1225–1230 (1988)].

It has been suggested that abnormal expression of GD3 is due to α-2,8-sialyltransferase, which is a GD3 synthetase [Yusuf et al.: Biological Chemistry Hoppe-Seyler, 368, 455–462 (1987)]. Only the partial purification of GD3 synthetase has been reported [Gu et al.: Biochemical and Biophysical Research Communications, 166, 387–393 (1990)]. No GD3 synthetase has been isolated as yet.

Attempts have been made to effect passive immunization of cancer patients by administering a monoclonal antibody to GD3 [Houghton et al.: Proceedings of the National Academy of Sciences of the U.S.A., 82, 1242 (1985)] and to effect active immunization of cancer patients by administering GD3 per se as a vaccine [Portoukalian et al. International Journal of Cancer, 49, 893–899 (1991); Ritter et al.: International Journal of Cancer, 48, 379–385 (1991)]. GD3 is thus a valuable cancer antigen. The quantity of GD3 that can be obtained by purification from tissues, however, is limited [Takamizawa et al.: Journal of Biological Chemistry, 261, 5625–5630 (1986)]. Chemical synthesis of GD3 requires sophisticated techniques and yields are very low [Ito et al.: Journal of the American Chemical Society, 111, 8508–8510 (1989)].

In view of the above-described association of GD3 with oncogenesis or cancer metastasis, it is expected that cancer might be treated by inhibiting the enzymatic activity of the GD3 synthetase α-2,8-sialyltransferase or suppressing expression of the relevant gene. Antisense RNA/antisense DNA techniques [Tokuhisa: Bioscience and Industry, 50, 322 (1992); Murakami; Kagaku (Chemistry), 46, 681 (1991)] and triple helix techniques [Chubb and Hogan: Trends in Biotechnology, 10, 132 (1992)] can be used to suppress gene expression specifically. For suppressing expression of a specific glycosyltransferase using the antisense RNA/DNA technique, the gene in question or information about the base sequence of the gene is required. It is thus important to clone the desired glycosyltransferase gene and determine the base sequence of same.

Further, as mentioned above, GD3 synthetase α-2,8-sialyltransferase is associated with oncogenesis and it is thus expected that it could be used in cancer diagnosis, that is, that the level of expression of the synthetase could be used to detect the presence of a tumor. The following can be used to assay expression of the α-2,8-sialyltransferase (GD3 synthetase) gene: Northern hybridization using the gene in a labeled form, for example in a radiolabeled form, as a probe [Sambrook, Fritsch and Maniatis: Molecular Cloning—A laboratory manual, second edition, Cold Spring Harbor Laboratory Press, 1989] and polymerase chain reaction (hereinafter, "PCR") [Innis et al.: PCR Protocols, Academic Press, 1990]. In applying these techniques, the gene for the GD3 synthetase α-2,8-sialyltransferase or knowledge of the base sequence thereof is required. From this viewpoint as well, it is important to clone the gene for GD3 synthetase α-2,8-sialyltransferase and determine its base sequence.

JP-A-2-227075 discloses the possibility of improving the properties of physiologically active useful proteins, such as granulocyte colony stimulating factor (G-CSF) and prourokinase (pro-UK), by artificially introducing a carbohydrate chain into the proteins using recombinant DNA technology.

It is an important problem from an industrial viewpoint to modify the structure of the carbohydrate chain of a glycoprotein or a glycolipid, or to prepare a specific carbohydrate chain or a modification thereof in large quantities, making use of α-2,8-sialyltransferase activity of the GD3 synthetase.

There have been marked advances in recent years in the means for modifying carbohydrate chain structures. In particular, it is now possible to structurally modify carbohydrate chains using highly specific enzymes (exoglucosidases) that are capable of releasing carbohydrate units one by one from the end of the carbohydrate chain, or glycopeptidases or endoglycosidases that are capable of cleaving the site of binding to the peptide chain without causing any change in either the peptide or carbohydrate chains, and accordingly, to study biological roles of carbohydrate chains in detail. The recent discovery of endoglycoceramidases that are capable of cleaving the glycolipids at the site between the carbohydrate chain and the ceramide [Ito and Yamagata: Journal of Biological Chemistry, 261, 14278 (1986)] has not only made it easy to prepare carbohydrate chains of glycolipids but has also promoted investigations into functions of glycolipids, in particular glycolipids occurring in cell surface layers. Further, it has become possible to add new carbohydrate chains using glycosyl-transferases. Thus, for instance, sialic acid can be added to a carbohydrate chain terminus using sialyltransferase [Sabesan and Paulson: Journal of the American Chemical Society, 108, 2068 (1986)]. It is also possible, using various glycosyltransferases or glycosidase inhibitors, to modify carbohydrate chains that are to be added [Allan et al.: Annual Review of Biochemistry, 56, 497 (1987)]. However, there is no means available for producing glycosyltransferases for use in synthesizing carbohydrate chains. It is desirable to produce glycosyltransferases in large quantities by cloning glycosyl-transferase genes and causing efficient expression of glycosyl-transferases in host cells utilizing recombinant DNA technology.

As far as sialyltransferase is concerned, a gene for an enzyme having β-galactoside α-2,6-sialyl transferase activity has been isolated and the base sequence thereof has been reported [Weinstein et al.: Journal of Biological Chemistry, 262, 17735 (1987)]. As regards an enzyme having β-galactoside α-2,3-sialyltransferase activity, cloning of a gene coding for an enzyme catalyzing the addition of sialic acid to galactose in an O-glycoside bond type carbohydrate chain (carbohydrate chain added to a serine or threonine residue) of glycoproteins has been reported by Gillespie et al. but the base sequence of said gene has not been reported [Gillespie et al.: Glycoconjugate Journal, 7, 469 (1990)]. Weinstein et al. reported a method of purifying an enzyme having β-galactoside α-2,3-sialyltransferase activity from rat liver [Weinstein et al.: Journal of Biological Chemistry, 257, 13835 (1982)]. This method, however, provides the desired enzyme only in very small amounts. This rat liver β-galactoside α-2,3-sialyltransferase gene has been cloned by Wen et al. [Wen et al.: Journal of Biological Chemistry, 267, 21011 (1992)]. There has been no report, however, of the cloning of a gene for human galactoside α-2,8-sialyltransferase. Large scale preparation of a sialyltransferase species having α-2,8-sialyltransferase activity or cloning of a gene for encoding a product having sialyltransferase activity has not been reported as yet. Therefore, no means is currently available for large scale preparation of a sialyl transferase having α-2,8-sialyltransferase activity, in particular human galactoside α-2,8-sialyltransferase. Methods of detecting or suppressing expression of the enzyme have also not been established.

It is an object of the present invention to provide a novel α-2,8-sialyltransferase species that would make possible efficient production of the ganglioside GD3, a cDNA coding for α-2,8-sialyltransferase, and a vector containing that cDNA. Another object is to provide a method of detecting α-2,8-sialyltransferase activity, which method would be useful in the diagnosis or treatment of diseases such as cancer, and a method of suppressing the expression of α-2,8-sialyltransferase.

DISCLOSURE OF THE INVENTION

The present inventors extracted mRNA from the human melanoma cell line WM266-4, synthesized cDNA using the mRNA as a template, inserted the cDNA into an expression cloning vector, introduced the thus-constructed cDNA library into cells, selected, from among the cells obtained, cells strongly reactive with an antibody specific for the ganglioside GD3 using a fluorescence activated cell sorter (hereinafter, "FACS") and thus successfully cloned a gene coding for a novel species of α-2,8-sialyltransferase. They further introduced the α-2,8-sialyltransferase-encoding gene into Namalwa cells to effect expression of the gene and found that the novel α-2,8-sialyltransferase was expressed in the cells and further that the amount of the ganglioside GD3 present on the cell surface increased.

The present invention is described in detail as follows.

The present invention relates, in one embodiment, to a novel α-2,8-sialyltransferase species comprising the amino acid sequence defined in SEQ ID NO:2. The invention further relates to a cDNA coding for α-2,8-sialyltransferase and to a recombinant vector harboring the cDNA, and to a cell containing the recombinant vector. The α-2,8-sialyltransferase of the present invention catalyzes the addition of a sialic acid residue, in α2→8 linkage, to a sialic acid residue contained in the ganglioside GM3 which is an acceptor.

DNA sequences coding for the α-2,8-sialyltransferase of the present invention include, (a) DNA comprising the base sequence defined in SEQ ID NO:1; (b) DNA containing a base sequence different from the base sequence defined in SEQ ID NO:1, the difference being due to the availability of a plurality of codons for one amino acid or to spontaneous mutation occurring in individual animals including human; and (c) DNA derived from the DNA defined in (a) or (b) by mutation, such as substitution, deletion or insertion mutation, that does not cause loss of α-2,8-sialyltransferase activity, for example, DNA encoding a modified amino acid sequence derived from the sequence defined in SEQ ID NO:2 from which the first to 56th amino acid residues from the N-terminus are deleted as shown in Example 3 below, or DNA homologous to the α-2,8-sialyltransferase-encoding DNA defined in (a) or (b) that can be isolated by the hybridization. Homologous DNA means DNA obtainable by the colony hybridization or plaque hybridization technique using a DNA containing the base sequence defined in SEQ ID NO:1 as a probe. Specifically, homologous DNA means DNA identifiable by performing hybridization at 65° C. in the presence of 0.7–1.0 M sodium chloride using a filter with a colony- or plaque-derived DNA fixed thereon and then washing the filter in a 0.1-fold to 2-fold concentrated SSC solution (1-fold concentrated SSC solution comprising 150 mM sodium chloride and 15 mM sodium citrate) at 65° C. The hybridization procedure is described in Molecular Cloning—A Laboratory Manual, 2nd Edition, edited by Sambrook, Fritsch and Maniatis, Cold Spring Harbor Laboratory Press, 1989. Any α-2,8-sialyltransferase species encoded by DNAs defined above in (a), (b) and (c) is included in the α-2,8 sialyltransferase of the present invention.

The following describes a method of producing DNA coding for the α-2,8-sialyltransferase of the present invention is described, taking DNA defined above in (a) as an example.

A cDNA library is constructed by inserting cDNA synthesized using mRNA extracted from the animal cell as a template into an expression cloning vector. This cDNA library is introduced into animal cells or insect cells, then cells that react strongly with an antibody specific for the ganglioside GD3 are enriched and isolated utilizing a FACS. The desired α-2,8-sialyltransferase-encoding cDNA is isolated from the cells.

Animal cells suitable for use in the above process can be any cells provided that they are animal cells in which the α-2,8-sialyltransferase of the present invention is expressed. Thus, for instance, the human melanoma cell line WM266-4 (ATCC CRL 1676) can be used. The vector into which the cDNA synthesized using the mRNA extracted from these cells as a template is to be inserted can be any vector provided that it allows insertion thereinto and expression of the cDNA. For instance, pAMoPRC3Sc or the like can be used. The animal or insect cells into which the cDNA library constructed using the vector is introduced can be any cells provided that they allow introduction therein and expression of the cDNA library. Thus, for instance, human Namalwa cells [Hosoi et al.: Cytotechnology, 1, 151 (1988)] or the like can be used. In particular, a direct expression cloning system using Namalwa cells as the host is advantageous in that the efficiency of introduction of a cDNA library into host Namalwa cells is very high and in that the plasmids (cDNA library) introduced can be maintained extrachromosomally in the system and can be readily recovered from the cells obtained by screening using a carbohydrate chain-specific antibody and a FACS. Therefore, this system is preferred. The anti-ganglioside GD3 antibody to be used in the practice of the invention can be any antibody provided that it reacts with the ganglioside GD3. For instance, KM-643 (EP-A-0493686) can be used. The animal cells, after introduction thereinto of the cDNA library, are fluorescence-labeled using the anti-GD3 antibody and then cells showing increased binding to the antibody are separated and enriched using a FACS. From the cells thus obtained, a plasmid or DNA fragment containing the cDNA coding for the α-2,8 sialyltransferase of the present invention is re covered using, for example, known methods, e.g. the Hart method [Robert F. Margolskee et al.: Molecular and Cellular Biology, 8, 2837 (1988)]. Plasmids of the invention containing cDNA coding for the enzyme include pUC119-WP1R. *Escherichia coli* JM105/pUC119-WP1R, an *Escherichia coli* strain harboring pUC119-WP1R, was deposited, on Feb. 18, 1993, at the National Institute for Bioscience and Human Technology, Agency of Industrial Science and Technology of 1–3, Higashi 1-chome, Tsukuba-shi, Ibaraki 305, JAPAN under the deposit number FERM BP-4192 (Budapest Treaty deposit).

The DNA defined above in (b) or (c) can be produced using the well-known recombinant DNA techniques [JP-A-2-227075; Molecular Cloning—A Laboratory Manual, 2nd Edition, Cold Spring Harbor Laboratory Press, 1989; etc.], such as hybridization techniques or methods of introducing mutation into DNA, based on the α-2,8-sialyltransferase-encoding cDNA obtained by the method described above. The α-2,8-sialyltransferase-encoding cDNA of the present invention can also be produced by chemical synthesis.

The α-2,8-sialyltransferase of the present invention can be produced by constructing a recombinant vector by inserting DNA coding for the α-2,8-sialyltransferase of the present invention obtained, for example, by the method described above into an appropriate vector and in operable linkage with a suitable promoter, introducing the recombinant vector into host cells and cultivating the cells obtained. The host cells to be used here can be any host cells suitable ror use in recombinant DNA technology, for example, prokaryotic cells, animal cells, yeasts, fungi and insect cells. An example of a suitable prokaryotic cell is *Escherichia coli*. CHO cells (Chinese hamster cells), COS cells (sminian cells) and Namalwa cells (human cells) are examples of suitable animal cells.

Vectors into which DNA coding for the α-2,8-sialyltransferase of the present invention is inserted can be any vector provided that it allows insertion therein of the α-2,8-sialyltransferase-encoding DNA and expression of the DNA in host cells. pAGE107 [JP-A-3-22979; Miyaji et al.: Cytotechnology, 3, 133 (1990)], pAS3-3 (JP-A-2-227075), pAMoERC3Sc, and CDM8 [Brian Seed et al.: Nature, 329, 840 (1987)] are examples. For the expression of the enzyme of the present invention in *Escherichia coli*, a plasmid is preferably used. The foreign DNA is inserted into the plasmid so that it is operably linked to a promoter with potent transcription activity, for example, the trp promoter, and so that the distance between the Shine-Dalgarno sequence (hereinafter, "SD sequence") and the initiation codon is of an appropriate length (for example 6–18 bases). Plasmid pKYP10 (JP-A-58-110600), pLSA1 [Miyaji et al.: Agricultural and Biological Chemistry, 53, 277 (1989)] and pGEL1 [Sekine et al.: Proceedings of the National Academy of Sciences of the U.S.A., 82, 4306 (1985)] are specific examples.

Recombinant DNA techniques to be used in the practice of the invention include those described in JP-A-2-227075 or those described in Sambrook, Fritsch, Maniatis et al.: Molecular Cloning—A Laboratory Manual, 2nd Edition, Cold Spring Harbor Laboratory Press, 1989. A number of commercially available kits can be used for mRNA isolation and cDNA library construction. Known methods can be used to introduce the DNA into animal cells. The electroporation method [Miyaji et al.: Cytotechnology, 3, 133 (1990)], the calcium phosphate method (JP-A-2-227075) and the lipofection method [Philip L. Felgner et al.: Proceedings of the National Academy of Sciences of the U.S.A., 84, 7413 (1987)] are examples. Transformant isolation and cultivation can be performed essentially according to the method described in JP-A-2-227075 or JP-A-2-257891.

Suitable methods of producing the α-2,8-sialyltransferase include the method of intracellular production in a host, the method of extracellular production or the method of production on a host cell membrane external layer. The site of production varies depending on the kind of host cell used and the form of the glycosyltransferase to be produced. In cases where animal cells are used as the host and a glycosyltransferase is produced in its native form, the enzyme is generally produced within the host cells or on the host cell membrane external layer and a portion of the enzyme produced is cleaved with protease and secreted extracellularly. The DNA recombination technique of Paulson et al. [C. Paulson et al.: The Journal of Biological Chemistry, 264, 17619 (1989)] and Low et al. [John B. Lowe et al., Proceedings of the National Academy of Sciences of the U.S.A., 86, 8227 (1989); John B. Lowe et al.: Genes & Development, 4, 1288 (1990)] can be used to cause production of the enzyme in a form composed of a glycosyltransferase portion containing the active site and a signal peptide added thereto.

Production of the enzyme can be increased by utilizing a gene amplification system using the dihydrofolate reductase gene, for example, as described in JP-A-2-227075.

Alpha-2,8-sialyltransferase produced in accordance with the present invention can be purified using ordinary methods of purifying glycosyltransferases [J. Evan. Sadler et al.: Methods of Enzymology, 83, 458]. When produced in *Escherichia coli*, the enzyme can be efficiently purified by a combination of the above method and the method described in JP-A-63-267292. It is also possible to produce the enzyme of the present invention in the form of a fusion protein and to purify the same by affinity chromatography using a substance having affinity for the fused protein. For example, the enzyme of the present invention can be produced fused with protein A. Such a protein can be purified by affinity chromatography using immunoglobulin G, essentially according to the method of Lowe et al. [John B. Lowe et a;.: Proceedings of the National Academy of Sciences of the U.S.A., 86, 8227 (1989); John B. Lowe et al.: Genes & Development, 4, 1288 (1990). It is also possible to purify the enzyme by affinity chromatography using an antibody to the enzyme.

The sialyltransferase activity can be determined according to known methods [J. Evan. Sadler et al.: Methods in Enzymology, 83, 458; Bo E. Samuelson: Methods in Enzymology, 138, 567; Manju Basu et al.: Methods in Enzymology, 138, 575; and Naoyuki Taniguti et al.: Methods in Enzymology, 179, 397].

Carbohydrate chains can be synthesized in vitro using the α-2,8-sialyltransferase of the present invention. For example, the nonreducing end of oligosaccharides NeuAc α2→3Gal β1→4Glc can be provided with a sialic acid residue in α2→8 linkage. Further, the ganglioside GM3 which serves as a substrate, when treated with the α-2,8-sialyltransferase of the present invention, can be modified to the ganglioside GD3.

By using DNA coding for the α-2,8-sialyltransferase of the present invention and causing simultaneous production of α-2,8-sialyltransferase and a carbohydrate chain (a glycoprotein, glycolipid or oligosaccharide) to serve as an acceptor substrate of the α-2,8-sialyltransferase in animal or insect cells that are producing the carbohydrate chain, it is possible to cause the α-2,8-sialyltransferase produced to act on the carbohydrate chain in the cells to provide a sialic acid residue with a nonreducing end of the carbohydrate chain. For instance, the ganglioside GD3 can be produced by effecting simultaneous production of the α-2,8-sialyltransferase in cells that are producing the ganglioside GM3.

Furthermore, it is also possible to excise, by known enzymatic or chemical techniques, a part of the oligosaccharide from the glycoprotein, glycolipid or oligosaccharide having a modified carbohydrate chain structure as produced in the above manner.

DNA coding for the α-2,8-sialyltransferase of the present invention can be used not only to effect modification of a carbohydrate chain of a protein or glycolipid or to effect efficient production of a specific carbohydrate chain, but also to treat diseases, such as inflammation and cancer metastasis utilizing, for example, antisense RNA/DNA techniques. Such DNA can also be used in the diagnosis of such diseases, for example, utilizing Northern hybridization and PCR techniques.

For instance, DNA coding for the α-2,8-sialyltransferase of the present invention can be used to prevent expression of the α-2,8-sialyltransferase by antisense RNA/DNA technology [Tokuhisa: Bio science and Industry, 50, 322–326 (1992); Murakami: Kagaku (Chemistry), 46, 681–684 (1991); Miller: Bio technology, 9, 358–362 (1992); Cohen: Trends in Biotechnology, 10, 87–91 (1992); Agrawal: Trends in Biotechnology, 10, 152–158 (1992)] or triple helix techniques [Chubb and Hogan: Trends in Biotechnology, 10, 132–136 (1992)]. More specifically, based on a part of the base sequence of the DNA coding for the α-2,8-sialyltransferase of the present invention, preferably a base sequence of 10–50 bases in length as occurring in the translation initiation region, an oligonucleotide can be designed and prepared and administered in vivo, under conditions such that production of the α-2,8-sialyltransferase is suppressed. The base sequence of the synthetic oligonucleotide can be one that is in agreement with a part of the base sequence of the antisense strand of the DNA of the present invention or one that is modified without causing loss of its ability to inhibit the activity expression of the α-2,8-sialyltransferase. When the triple helix technique is employed, the base sequence of the synthetic oligonucleotide can be designed based on the base sequence of both the sense and antisense strands.

It is also possible to detect the production of the α-2,8-sialyltransferase of the present invention using the hybridization or PCR technique. For detecting the production of the α-2,8-sialyltransferase of the present invention using the Northern hybridization or PCR technique, the DNA coding for the α-2,8-sialyltransferase of the present invention or a synthetic oligonucleotide synthesized based on the base sequence thereof can be used. Northern hybridization and PCR can be carried out in a conventional manner [Sambrook, Fritsch and Maniatis: Molecular Cloning—A Laboratory Manual, 2nd Edition, Cold Spring Harbor Laboratory Press, 1989; Innis et al.: PCR protocols, Academic Press, 1990].

The symbols used in the figures respectively have the following meanings:
  dhfr: Dihydrofolate reductase gene
  hG-CSF: Human granulocyte colony stimulating factor gene
  bp: Base pairs
  kb: Kilobase pairs
  G418/Km: Transposon 5 (Tn 5)-derived G418/kanamycin resistance gene
  hyg: Hygromycin resistance gene
  Ap: pBR322-derived ampicillin resistance gene
  Tc: pBR322-derived tetracycline resistance gene
  P1: pBR322-derived P1 promoter
  Ptk: Herpes simplex virus (HSV) thymidine kinase (tk) gene promoter
  Sp.βG: Rabbit β globin gene splicing signal
  A.βG: Rabbit β globin gene poly(A) addition signal
  A.SE: Simian virus 40 (SV40) early gene poly(A) addition signal
  Atk: Herpes simplex virus (HSV) thymidine kinase (tk) gene poly(A) addition signal
  Pse: Simian virus 40 (SV40) early gene promoter
  Pmo: Moloney murine leukemia virus long terminal repeat (LTR) promoter
  HTLV-1: Human T cell leukemia virus type-1 (HTLV-1) gene
  EBNA-1: Epstein-Barr virus EBNA-1 gene
  oriP: Epstein-Barr virus replication origin
  ori: pUC119 replication origin
  Lac'Z: Part of *Escherichia coli* β galactosidase gene
  IG: M13 phage DNA intergenic region
  G-CSF der.: Human granulocyte colony stimulating factor derivative gene
  S: Gene portion coding for human granulocyte colony stimulating factor signal peptide
  A or ProA: Gene portion coding for binding region of *Staphylococcus aureus* protein A to IgG
  WP1: GD3 synthetase gene obtained from WM266-4 cells (full-length gene or active region gene)

Certain aspects of the present invention are described in greater detail in the non-limiting Examples that follow.

EXAMPLE 1

Cloning of α-2,8-sialyltransferase-Encoding DNA (WP1) from Cells of Human Melanoma Cell Line WM266-4

1. Construction of Direct Expression Cloning Vectors pAMoERC3Sc and pAMoPRC3Sc pAMoERC3Sc was constructed according to steps (1) to (14) described below.

Figure 1:
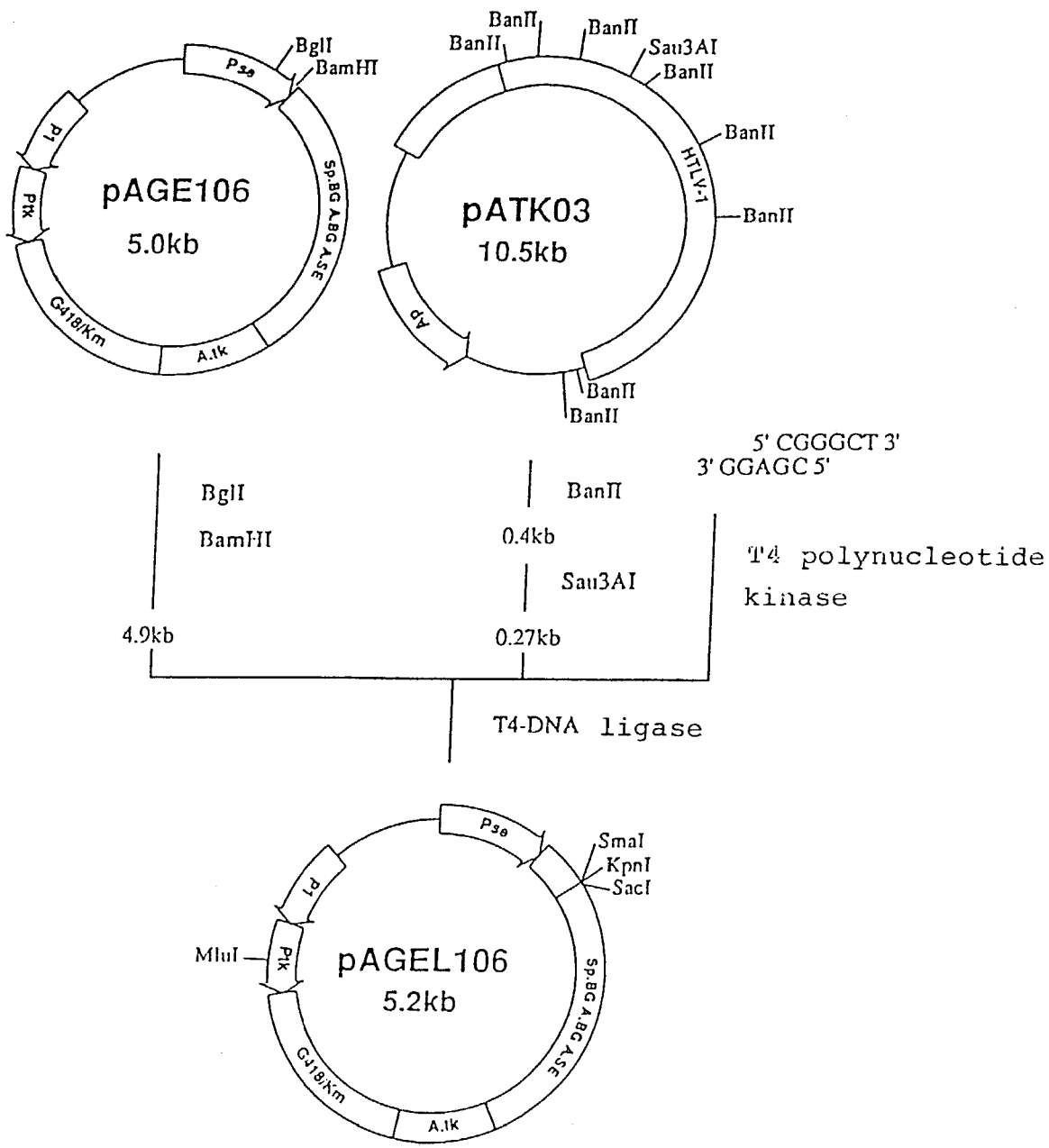
FIG. 1 shows a construction scheme for the plasmid pAGEL106.

(1) Construction of pAGEL106 (cf. FIG. 1)

A plasmid, pAGEL106, having a promoter resulting from fusion of the simian virus 40 (SV40) early gene promoter and parts of the R and U5 regions of the long terminal repeat (LTR) of the human T-cell leukemia virus type-1 (HTLV-1) was constructed. A DNA fragment [BanII-Sau3A fragment (0.27 kb)] containing parts of the R and U5 regions was excised from pATK03 and inserted into pAGE106 between BglI-BamHI sites via a synthetic linker.

pAGE106 (JP-A-2-227075) (1 μg) was dissolved in 30 μl of a buffer comprising 10 mM Tris-hydrochloride (pH 7.5), 6 mM magnesium chloride, 100 mM sodium chloride and 6 mM 2-mercaptoethanol (hereinafter "Y-100 buffer"), 10 units of BglI (Takara Shuzo; unless otherwise specified, the restriction enzymes mentioned hereinafter were products of Takara Shuzo) and 10 units of BamHI were added and the digestion reaction was carried out at 37° C. for 2 hours. The reaction mixture was subjected to agarose gel electrophoresis and a DNA fragment of about 4.9 kb was recovered.

Separately, 1 μg of pATK03 [Shimizu et al.: Proceedings of the National Academy of Sciences of the U.S.A., 80, 3618 (1983)] was dissolved in 30 μl of Y-100 buffer, 10 units of BanII was added and the digestion reaction was carried out at 37° C. for 2 hours. The reaction mixture was subjected to agarose gel electrophoresis and a DNA fragment of about 0.4 kb was recovered. The DNA fragment recovered was dissolved in 30 μl of Y-100 buffer, 10 units of Sau3AI was added and the digestion reaction was carried out at 37° C. for 2 hours. The reaction mixture was subjected to agarose gel electrophoresis and a DNA fragment of about 0.27 kb was recovered.

Further, separately, the following DNA linker was synthesized and used for linking the BglI and BanII cleavage sites together.

```
5' - CGGGCT - 3'  (6 mer)

3' - GGAGC  - 5'  (5 mer)
```

The 5 mer and 6 mer single-stranded DNAs for preparing the DNA linker were synthesized using an Applied Biosystems model 380A DNA synthesizer. The DNAs synthesized (0.2 μg each) were dissolved in 40 μl of a buffer comprising 50 mM Tris-hydrochloride (pH 7.5), 10 mM magnesium chloride, 5 mM dithiothreitol (hereinafter, DTT), 0.1 nM EDTA and 1 mM adenosine triphosphate (hereinafter ATP) (hereinafter "T4 kinase buffer"), 30 units of T4 polynucleotide kinase (Takara Shuzo; hereinafter the same shall apply) was added and the phosphorylation reaction was carried out at 37° C. for 2 hours.

The pAGE106-derived BglI-BamHI fragment (4.9 kb; 0.2 μg) and pATK03-derived BanII-Sau3A fragment (0.27 kb; 0.01 μg) obtained as described above were dissolved in 30 μl of a buffer containing 66 mM Tris-hydrochloride (pH 7.5), 6.6 mM magnesium chloride, 10 mM DTT and 0.1 mM ATP (hereinafter "T4 ligase buffer"), 0.01 μg of the DNA linker described above and 175 units of T4 DNA ligase (Takara Shuzo; hereinafter the same shall apply) were added and the ligation reaction was carried out at 12° C. for 16 hours.

The reaction mixture was used to transform *Escherichia coli* HB101 [Bolivar et al: Gene, 2, 75 (1977)] by the method of Cohen et al. [S. N. Cohen et al.: Proceedings of the National Academy of Sciences of the U.S.A., 69, 2110 (1972)] (hereinafter, this method was used for transforming *Escherichia coli*) and an ampicillin-resistant strain was obtained. From this transformant, a plasmid was isolated by a known method [H. C. Birnboim et al.: Nucleic Acids Research, 7, 1513 (1979)] (hereinafter this method was used for plasmid isolation). This plasmid was named pAGEL106 and its structure was identified by digestion with restriction enzymes.

Figure 2:
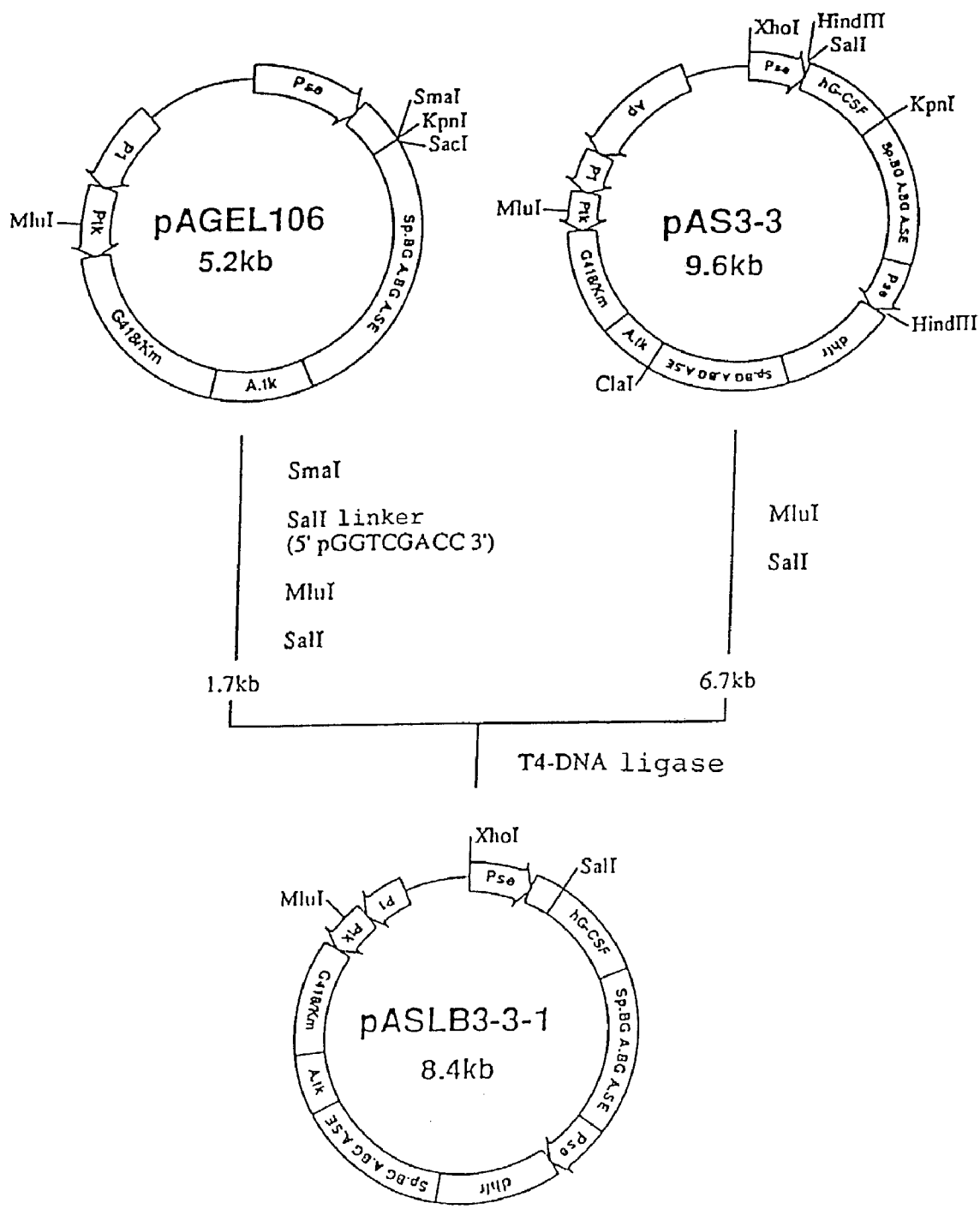
FIG. 2 shows a construction scheme for the plasmid pASLB3-3-1.

(2) Construction of pASLB3-3-1 (cf. FIG. 2)

A human granulocyte colony stimulating factor (hG-CSF) expression plasmid, pASLB3-3-1, having a promoter resulting from fusion of the SV40 early gene promoter and parts of the R and U5 regions of the long terminal repeat (LTR) of HTLV-1 was constructed in the following manner.

pAGEL106 (0.5 μg) obtained in (1) was dissolved in 30 μl of a buffer comprising 10 mM Tris-hydrochloride (pH 7.5), 6 mM magnesium chloride, 20 mM potassium chloride and 6 mM 2-mercaptoethanol (hereinafter "K-20 buffer"), 10 units of SmaI was added and the digestion reaction was carried out at 37° C. for 2 hours. After precipitation with ethanol, the precipitate was dissolved in 30 μl of T4 ligase buffer, 0.01 μg of a SalI linker (5'-pGGTCGACC-3'; Takara Shuzo) and 175 units of T4 DNA ligase were added and the ligation reaction was carried out at 12° C. for 16 hours. After precipitation with ethanol, the precipitate was dissolved in 30 μl of a buffer comprising 10 mM Tris-hydrochloride (pH 7.5), 6 mM magnesium chloride, 175 mM sodium chloride and 6 mM 2-mercaptoethanol (hereinafter "Y-175 buffer"), 10 units of SalI and 10 units of MluI were added and the digestion reaction was carried out at 37° C. for 2 hours. The reaction mixture was subjected to agarose gel electrophoresis and a DNA fragment of about 1.7 kb was recovered.

Separately, 1 μg of pAS3-3 (JP-A-2-227075) was dissolved in 30 μl of Y-175 buffer, 10 units of SalI and 10 units of MluI were added and the digestion reaction was carried out at 37° C. for 2 hours. The reaction mixture was subjected to agarose gel electrophoresis and a DNA fragment of about 6.7 kb was recovered.

The pAGEL106-derived MluI-SalI fragment (1.7 kg; 0.1 μg) and pAS3-3-derived MluI-SalI fragment (6.7 kb; 0.2 μg) obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLB3-3-1 and its structure was identified by digestion with restriction enzymes.

Figure 3:
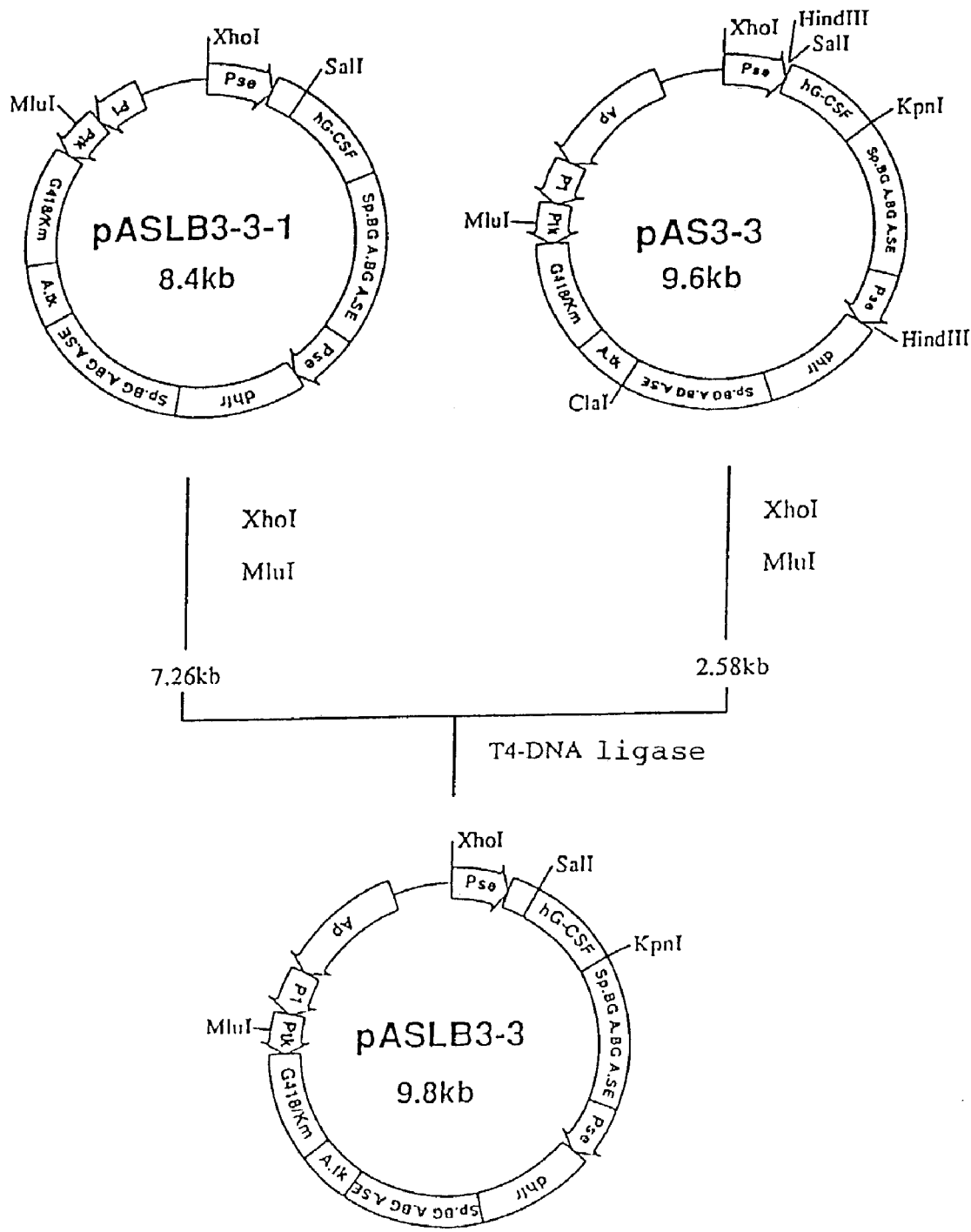
FIG. 3 shows a construction scheme for the plasmid pASLB3-3.

(3) Construction of pASLB3-3 (cf. FIG. 3)

For constructing a plasmid, pASLB3-3, by introducing the ampicillin resistance gene into pASLB3-3-1, an ampicillin resistance gene-containing DNA fragment [XhoI-MluI fragment (7.26 kb)] of pAS3-3 was introduced into pASLB3-3-1 between the XhoI and MluI sites.

pASLB3-3-1 (1 μg) obtained in (2) was dissolved in 30 μl of a buffer comprising 10 mM Tris-hydrochloride (pH 7.5), 6 mM magnesium chloride, 150 mM sodium chloride and 6 mM 2-mercaptoethanol (hereinafter "Y-150 buffer"), 10 units of XhoI and 10 units of MluI and the digestion reaction was carried out at 37° C. for 2 hours. The reaction mixture was subjected to agarose gel electrophoresis and a DNA fragment of about 7.26 kb was recovered.

Separately, 1 μg of pAS3-3 (JP-A-2-227075) was dissolved in 30 μl of Y-150 buffer, 10 units of XhoI and 10 units of MluI were added and the digestion reaction was carried out at 37° C. for 2 hours. The reaction mixture was subjected to agarose gel electrophoresis and a DNA fragment of about 2.58 kb was recovered.

The pASLB3-3-1-derived XhoI-MluI fragment (7.26 kb; 0.2 μg) and pAS3-3-derived XhoI-MluI fragment (2.58 kb; 0.1 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method and named pASLB3-3. Its structure was identified by digestion with restriction enzymes.

Figure 4:
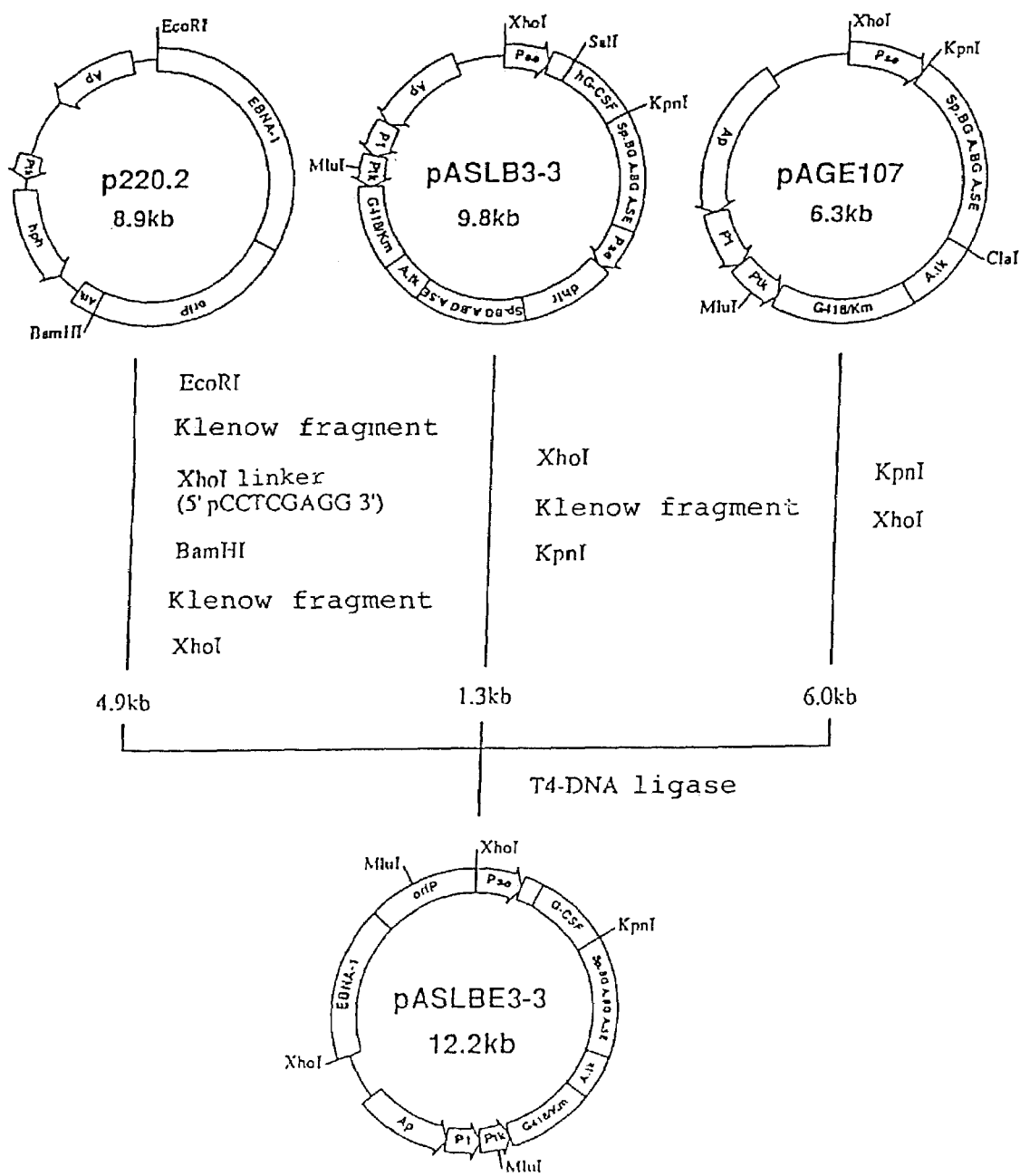
FIG. 4 shows a construction scheme for the plasmid pASLBE3-3.

(4) Construction of pASLBE3-3 (cf. FIG. 4)

A plasmid, pASLBE3-3, was constructed in the manner mentioned below by eliminating from pASLB3-3 the dihydrofolate reductase (dhfr) expression unit and, simultaneously, introducing thereinto the replication origin (oriP) and the EBNA-1 gene (acting trans on the oriP to induce replication) of the Epstein-Barr virus. The oriP and the EBNA-1 gene used were those excised from a plasmid p220.2 produced by incorporating a multicloning site-containing SmaI-HaeIII fragment derived from pUC12 [Messing et al.: Methods in Enzymology, 101 20 (1983)] into p201 [Bill Sugden et al.: Nature, 313, 812 (1985)] at the NarI site thereof.

p220.2 (1 μg) was dissolved in 30 μl of Y-100 buffer, 20 units of EcoRI was added and the digestion reaction was carried out at 37° C. for 2 hours. After precipitation with ethanol, the precipitate was dissolved in 30 μl of DNA polymerase I buffer [50 mM Tris-hydrochloride (pH 7.5), 10 mM magnesium chloride, 0.1 mM dATP (deoxyadenosine triphosphate), 0.1 mM dCTP (deoxycytidine triphosphate), 0.1 mM dGTP (deoxyguanosine triphosphate), 0.1 mM TTP (thymidine triphosphate)], 6 units of *Escherichia coli*-derived DNA polymerase I Klenow fragment was added and the reaction was carried out at 37° C. for 60 minutes to convert the 5' cohesive end formed upon EcoRI digestion to a blunt end. The reaction was terminated by extraction with phenol. After extraction with chloroform and precipitation with ethanol, the precipitate was dissolved in 20 μl of T4 ligase buffer, 0.05 μg of an XhoI linker (5'-pCCTCGAGG-3'; Takara Shuzo) and 175 units of T4 DNA ligase were added and the ligation reaction was carried out at 12° C. for 16 hours. After precipitation with ethanol, the precipitate was dissolved in 30 μl of Y-100 buffer, 10 units of BamHI was added and the digestion reaction was carried out at 37° C. for 2 hours. After precipitation with ethanol, the precipitate was dissolved in 30 μl of DNA polymerase I buffer, 6 units of Escherichia coli-derived DNA polymerase I Klenow fragment was added and the reaction was carried out at 37° C. for 60 minutes to convert the 5' cohesive end resulting from BamHI digestion to a blunt end. The reaction was terminated by extraction with phenol. After extraction with chloroform and precipitation with ethanol, the precipitate was dissolved in 30 μl of Y-100 buffer, 10 units of XhoI was added and the digestion reaction was carried out at 37° C. for 2 hours. The reaction mixture was subjected to agarose gel electrophoresis and a DNA fragment of about 4.9 kb was recovered.

Separately, pASLB3-3 (1 μg) obtained in (3) was dissolved in 30 μl of Y-100 buffer, 20 units of XhoI was added and the digestion reaction was carried out at 37° C. for 2 hours. After precipitation with ethanol, the precipitate was dissolved in 30 μl of DNA polymerase I buffer, 6 units of Escherichia coli-derived DNA polymerase I Klenow fragment was added and the reaction was carried out at 37° C. for 60 minutes to convert the 5' cohesive end resulting from XhoI digestion to a blunt end. The reaction was terminated by extraction with phenol. After extraction with chloro form and precipitation with ethanol, the precipitate was dissolved in 30 μl of a buffer comprising 10 mM Tris-hydrochloride (pH 7.5), 6 mM magnesium chloride and 6 mM 2-mercapto ethanol (hereinafter "Y-0 buffer"), 20 units of KpnI was added and the digestion reaction was carried out at 37° C. for 2 hours. The reaction mixture was subjected to agarose gel electrophoresis and a DNA fragment of about 1.3 kb was recovered.

Further, separately, 1 μg of pAGE107 [JP-A-3-22979; Miyaji et al.: Cytotechnology, 3, 133 (1990)] was dissolved in 30 μl of Y-0 buffer, 20 units of KpnI was added and the digestion reaction was carried out at 37° C. for 2 hours. Then, sodium chloride was added to a sodium chloride concentration of 100 mM, 20 units of XhoI was added and the digestion reaction was further carried out at 37° C. for 2 hours. The reaction mixture was subjected to agarose gel electrophoresis and a DNA fragment of about 6.0 kb was recovered.

The p220.2-derived XhoI-BamHI (blunt end) fragment (4.9 kb; 0.2 μg), pASLB3-3-derived XhoI(blunt end)-KpnI fragment (1.3 kb; 0.1 μg) and pAGE107-derived KpnI-XhoI fragment (6.0 kb; 0.2/μg) obtained as described above were dissolved in 30 μl of T4 ligase buffer, 175 units of T4 DNA ligase was added and the ligation reaction was carried out at 12° C. for 16 hours. The reaction mixture was used to transform Escherichia coli HB101 by the method of Cohen et al. and an ampicillin-resistant strain was obtained. From this transformant, a plasmid was isolated by a known method. This plasmid was named pASLBE3-3 and its structure was identified by digestion with restriction enzymes.

Figure 5:
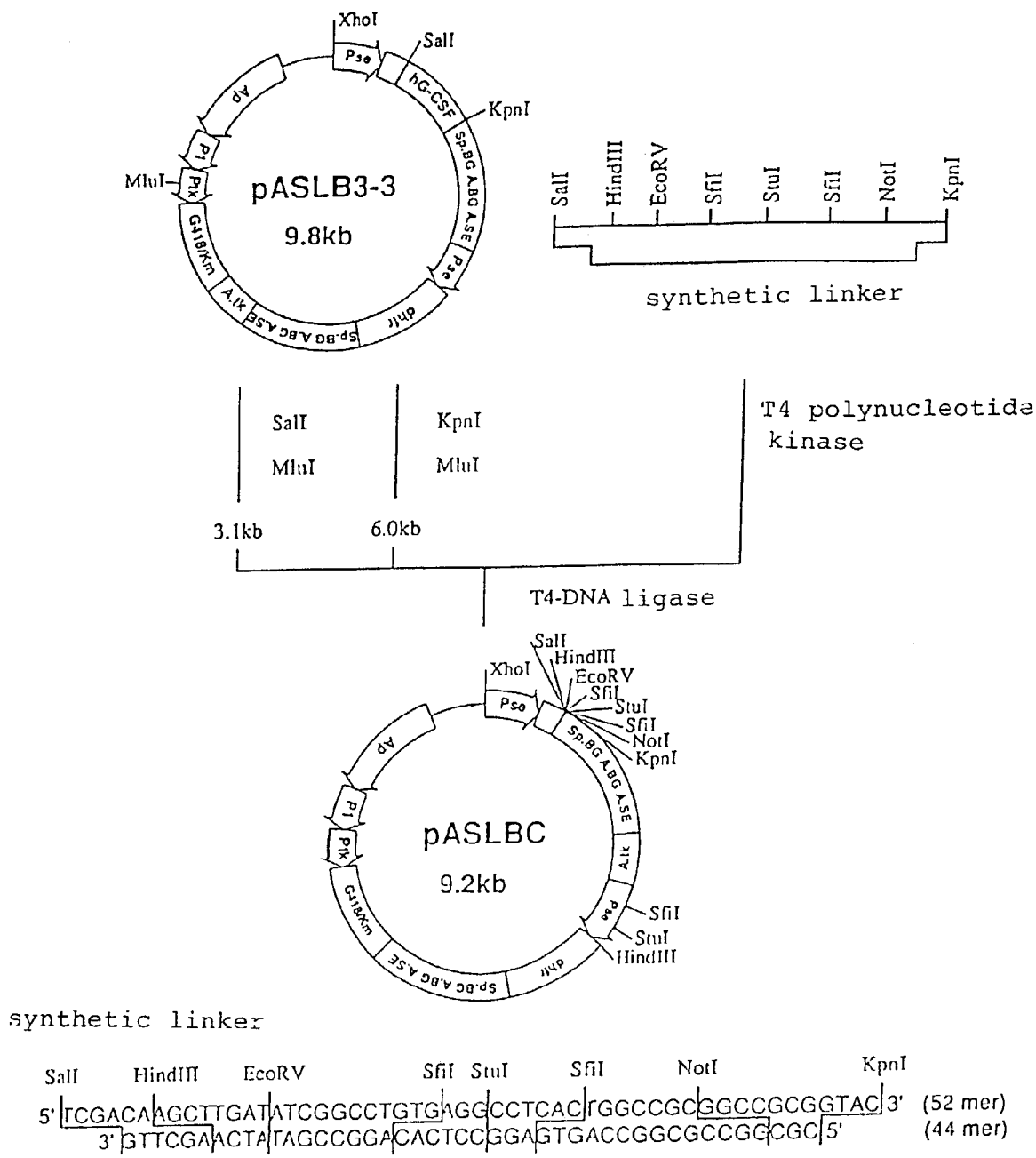
FIG. 5 shows a construction scheme for the plasmid pASLBC.

(5) Construction of pASLBC (cf. FIG. 5)

A plasmid, pASLBC, was constructed by eliminating from pASLB3-3 the hG-CSF gene and, instead, introducing thereinto a multicloning site. The multicloning site was prepared using synthetic DNAs.

pASLB3-3 (1 μg) obtained in (3) was dissolved in 30 μl of Y-175 buffer, 20 units of SalI and 20 units of MluI were added and the digestion reaction was carried out at 37° C. for 2 hours. The reaction mixture was subjected to agarose gel electrophoresis and a DNA fragment of about 3.1 kb was recovered.

Separately, 1 μg of the same plasmid was dissolved in 30 μl of Y-0 buffer, 20 units of KpnI was added and the digestion reaction was carried out at 37° C. for 2 hours. Then, sodium chloride was added to a sodium chloride concentration of 150 mM, 20 units of MluI was added and the digestion reaction was further carried out at 37° C. for 2 hours. The reaction mixture was subjected to agarose gel electrophoresis and a DNA fragment of about 6.0 kb was recovered.

Further, separately, the DNA linker specified below was synthesized as a linker for connecting the SalI cleavage site to the KpnI cleavage site. In this linker, the following restriction enzyme cleavage sites are incorporated: HindIII, EcoRV, SfiI, StuI and NotI. SalI HindIII EcoRV SfiI StuI SfiI NotI KpnI

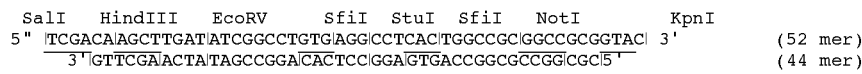

```
        SalI   HindIII    EcoRV      SfiI  StuI  SfiI   NotI         KpnI
5" TCGACA AGCTTGAT ATCGGCCTGTG AGG CCTCAC TGGCCGC GGCCGCGGTAC 3'        (52 mer)
        3' GTTCGA ACTA TAGCCGGA CACTCC GGA GTGACCGGCGCCG CGC 5"         (44 mer)
```

The 52 mer (SEQ ID NO: 3) and 44 mer (SEQ ID NO: 4) single-stranded DNAs of said DNA linker were synthesized using an Applied Biosystems model 380A DNA synthesizer. The thus-synthesized DNAs (0.2 μg each) were dissolved in 20 μl of T4 kinase buffer, 30 units of T4 polynucleotide kinase (Takara Shuzo; hereinafter the same shall apply) was added and the phosphorylation reaction was carried out at 37° C. for 2 hours.

The SalI-MluI fragment (3.1 kb; 0.1 μg) and KpnI-MluI fragment (6.0 kb; 0.2 μg) each derived from pASLB3-3 as described above were dissolved in 30 μl of T4 ligase buffer, 0.01 μg of the DNA linker described above and 175 units of T4 DNA ligase were added and the ligation reaction was carried out at 12° C. for 16 hours. The reaction mixture was used to transform Escherichia coli HB101 by the method of Cohen et al. and an ampicillin-resistant strain was obtained. From this transformant, a plasmid was isolated by a known method. This plasmid was named pASLBC and its structure was identified by digestion with restriction enzymes.

Figure 6:
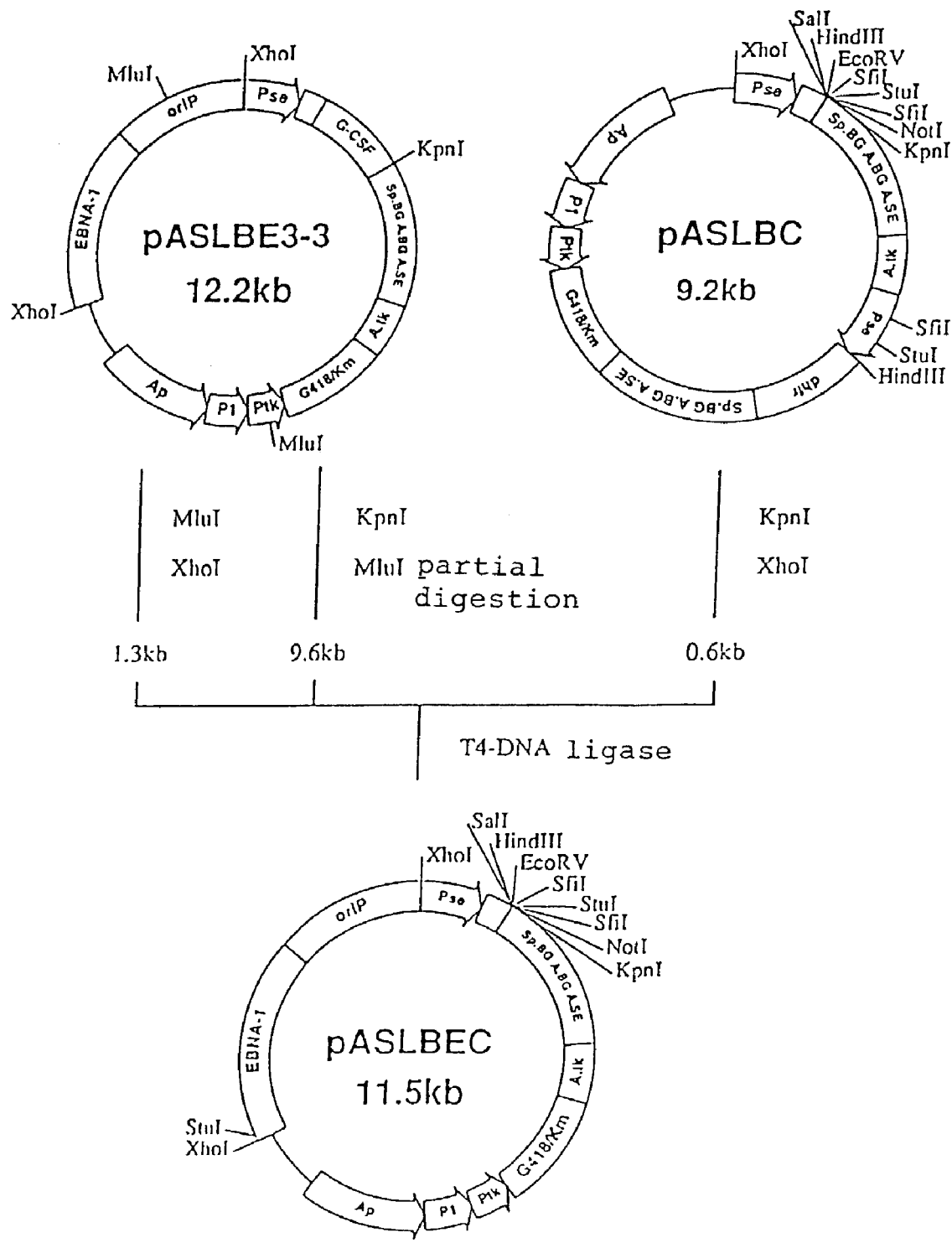
FIG. 6 shows a construction scheme for the plasmid pASLBEC.

(6) Construction of pASLBEC (cf. FIG. 6)

A plasmid, pASLBEC, was constructed by eliminating from pASLBC the dihydrofolate reductase (dhfr) expression unit and, instead, introducing thereinto the oriP and EBNA-1 gene.

pASLBE3-3 (1 μg) obtained in (4) was dissolved in 30 μl of Y-150 buffer, 20 units of MluI and 20 units of XhoI were added and the digestion reaction was carried out at 37° C. for 2 hours. The reaction mixture was subjected to agarose gel electrophoresis and a DNA fragment of about 1.3 kb was recovered.

Separately, 1 μg of the same plasmid was dissolved in 30 μl of Y-0 buffer, 20 units of KpnI was added and the digestion reaction was carried out at 37° C. for 2 hours. Then, sodium chloride was added to a sodium chloride concentration of 150 mM, 5 units of MluI was added and, further, partial digestion was effected at 37° C. for 20 minutes. The reaction mixture was subjected to agarose gel electrophoresis and a DNA fragment of about 9.6 kb was isolated.

Further, separately, pASLBC (1 μg) obtained in (5) was dissolved in 30 μl of Y-0 buffer, 20 units of KpnI was added and the digestion reaction was carried out at 37° C. for 2 hours. Then, sodium chloride was added to a sodium chloride concentration of 100 mM, 20 units of XhoI was added and, further, the digestion reaction was carried out at 37° C. for 2 hours. The reaction mixture was subjected to agarose gel electrophoresis and a DNA fragment of about 0.6 kb was isolated.

The MluI-XhoI fragment (1.3 kb; 0.2 μg) and KpnI-MluI fragment (9.6 kb; 0.2 μg) each derived from pASLBE3-3 as described above and the pASLBC-derived KpnI-XhoI fragment (0.6 kb; 0.05 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBEC and its structure was identified by digestion with restriction enzymes.

Figure 7:
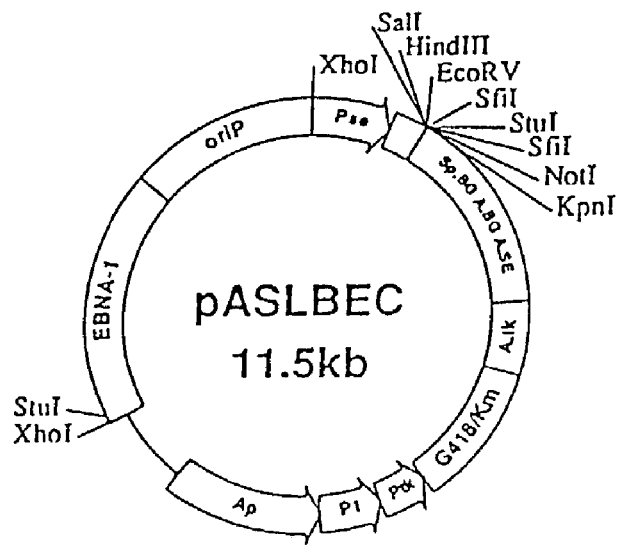
FIG. 7 shows a construction scheme for the plasmid pASLBEC2.
Figure 7:
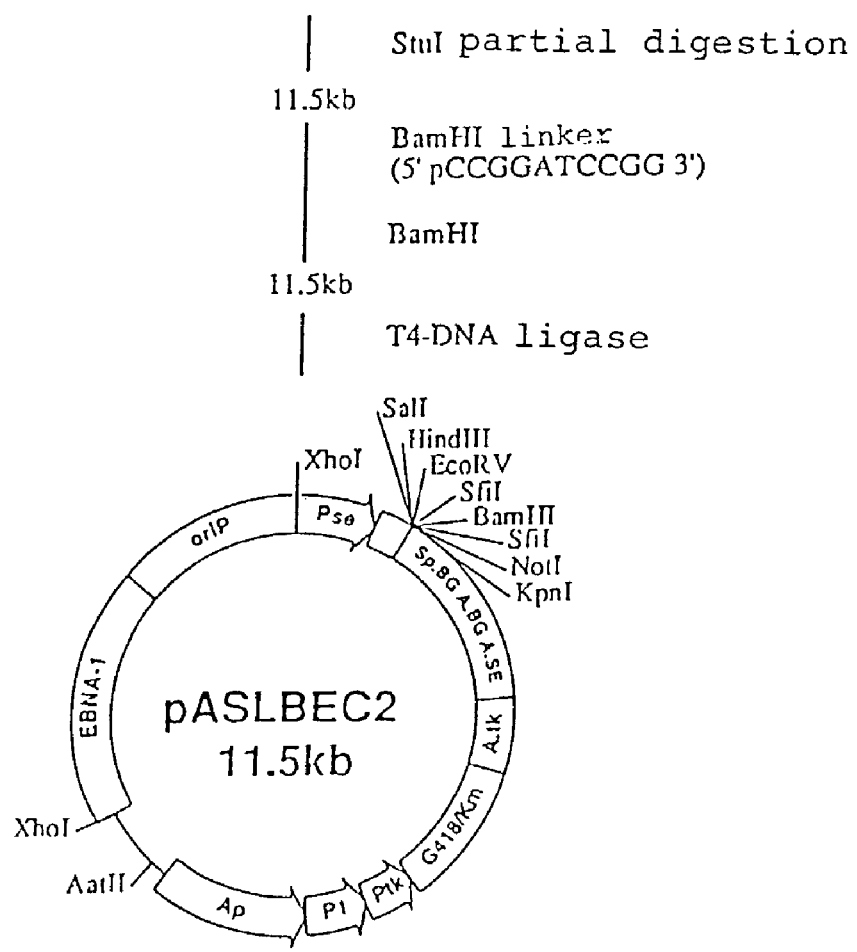

(7) Construction of pASLBEC2 (cf. FIG. 7)

A plasmid, pASLBEC2, was constructed in the manner described below by introducing a BamHI linker into the StuI site in the multicloning site of pASLBEC. In pASBEC2, the StuI site in the multicloning site is missing.

pASLBEC (1 μg) obtained in (6) was dissolved in 30 μl of Y-100 buffer, 5 units of StuI was added and partial digestion was effected at 37° C. for 20 minutes. The reaction mixture was subjected to agarose gel electrophoresis and a DNA fragment of about 11.5 kb was recovered. The DNA recovered was dissolved in 30 μl of T4 ligase buffer, 0.01 μg of a BamHI linker (5'-pCCGGATCCGG-3'; Takara Shuzo) and 175 units of T4 DNA ligase were added and the ligation reaction was carried out at 12° C. for 16 hours. After precipitation with ethanol, the precipitate was dissolved in 30 μl of Y-100 buffer, 20 units of BamHI was added and the digestion reaction was carried out at 37° C. for 2 hours. The reaction mixture was subjected to agarose gel electrophoresis and a DNA fragment of about 11.5 kb was recovered. The DNA fragment recovered was dissolved in 20 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pASLBEC2 and its structure was identified by digestion with restriction enzymes.

Figure 8:
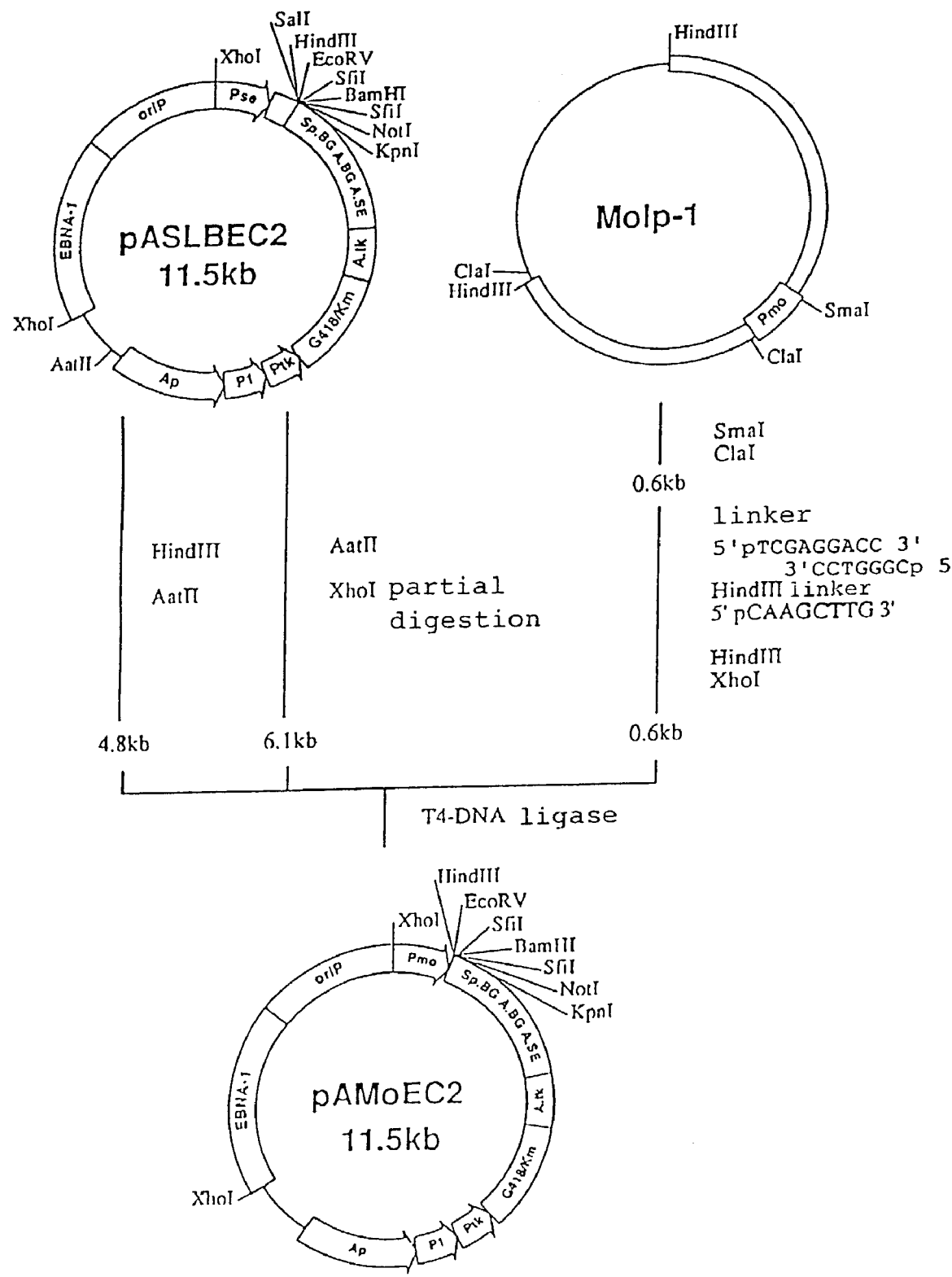
FIG. 8 shows a construction scheme for the plasmid pAMoEC2.

(8) Construction of pAMoEC2 (cf. FIG. 8)

A plasmid, pAMoEC2, was constructed in the manner described below by replacing the promoter in pASLBEC2 [promoter resulting from fusion of the SV40 early gene promoter and parts of the R and U5 regions of the long terminal repeat (LTR) of HTLV-1] with the promoter of the long terminal repeat (LTR) of the Moloney murine leukemia virus. The promoter of Moloney murine leukemia virus LTR was excised for use from the plasmid Molp-1 [Akinori Ishimoto et al.: Virology, 141, 30 (1985)].

pASLBEC2 (1 μg) obtained in (7) was dissolved in 30 μl of a buffer comprising 10 mM Tris-hydrochloride (pH 7.5), 6 mM magnesium chloride, 50 mM potassium chloride and 6 mM 2-mercaptoethanol (hereinafter "K-50 buffer"), 20 units of HindIII and 20 units of AatII (Toyobo) were added and the digestion reaction was carried out at 37° C. for 2 hours. The reaction mixture was subjected to agarose gel electrophoresis and a DNA fragment of about 4.8 kb was recovered.

Separately, 1 μg of the same plasmid was dissolved in 30 μl of K-50 buffer, 20 units of AatII was added and the digestion reaction was carried out at 37° C. for 2 hours. Then, 5 units of XhoI was added and, further, partial digestion was effected at 37° C. for 20 minutes. The reaction mixture was subjected to agarose gel electrophoresis and a DNA fragment of about 6.1 kb was recovered.

Then, the linker shown below was synthesized as a linker for connecting the XhoI cleavage site to the ClaI cleavage site.

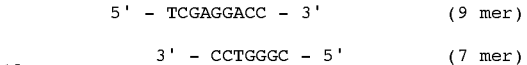

The 9 mer and 7 mer single-stranded DNAs for preparing the above DNA linker were synthesized using an Applied Biosystems model 380A DNA synthesizer. The DNA synthesized (0.2 μg each) were dissolved in 40 μl of T4 kinase buffer, 30 units of T4 polynucleotide kinase was added and the phosphorylation reaction was carried out at 37° C. for 2 hours.

Further, separately, 1 μg of Molp-1 [Akinori Ishimoto et al.: Virology, 141, 30 (1985)] was dissolved in 30 μl of Y-50 buffer, 20 units of ClaI was added and the digestion reaction was carried out at 37° C. for 2 hours. After precipitation with ethanol, the precipitate was dissolved in 30 μl of T4 ligase buffer, 0.01 μg of the DNA linker described above and 175 units of T4 DNA ligase were added and the ligation reaction was carried out at 12° C. for 16 hours. After precipitation with ethanol, the precipitate was dissolved in 30 μl of K-20 buffer, 20 units of SmaI was added and the digestion reaction was carried out at 37° C. for 2 hours. The reaction mixture was subjected to agarose gel electrophoresis and a DNA fragment of about 0.6 kb was recovered. The DNA fragment recovered was dissolved in 30 μl of T4 ligase buffer, 0.03 μg of a HindIII linker (5'-pCAAGCTTG-3'; Takara Shuzo) and 175 units of T4 DNA ligase were added and the ligation reaction was carried out at 12° C. for 16 hours. After precipitation with ethanol, the precipitate was dissolved in 30 μl of a buffer comprising 10 mM Tris-hydrochloride (pH 7.5), 6 mM magnesium chloride, 50 mM sodium chloride and 6 mM 2-mercaptoethanol (hereinafter "Y-50 buffer"), 10 units of HindIII was added and the digestion reaction was carried out at 37° C. for 2 hours. Then, sodium chloride was added to a sodium chloride concentration of 100 mM, 10 units of XhoI was added and the digestion reaction was further carried out at 37° C. for 2 hours. The reaction mixture was subjected to agarose gel electrophoresis and a DNA fragment of about 0.6 kb was recovered.

The HindIII-AatII fragment (4.8 kb; 0.2 μg) and AatII-XhoI fragment (6.1 kb; 0.2 μg) each derived from pASLBEC2 as described above and the Molp-1-derived HindIII-XhoI fragment (0.6 kb; 0.05 μg) were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoEC2 and its structure was identified by digestion with restriction enzymes.

Figure 9:
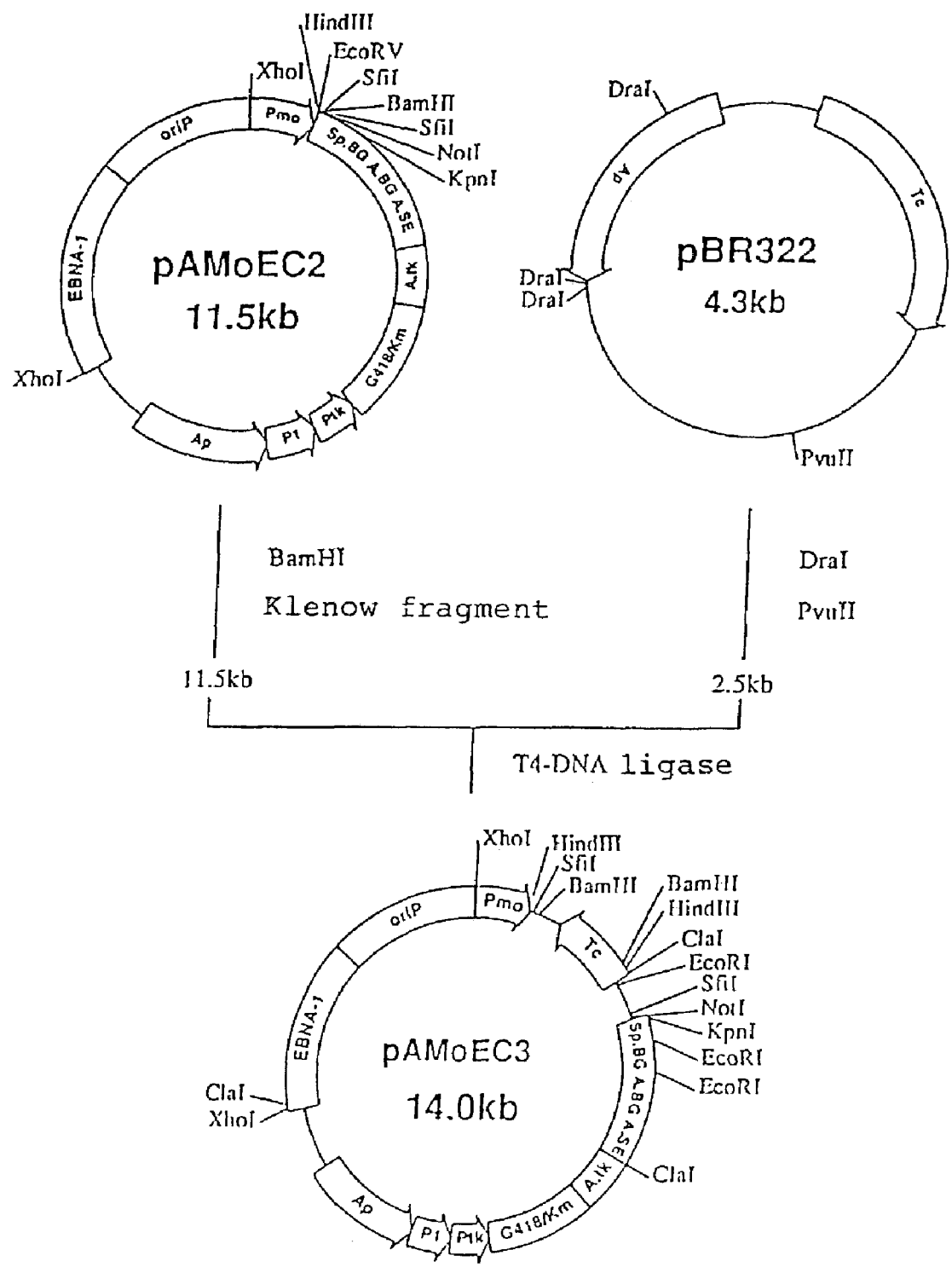
FIG. 9 shows a construction scheme for the plasmid pAMoEC3.

(9) Construction of pAMoEC3 (cf. FIG. 9)

A plasmid, pAMoEC3, was constructed in the manner described below by inserting, as a stuffer DNA, a DNA fragment [DraI-PvuII fragment (2.5 kb)] containing the tetracyline resistance gene of pBR322 into the BamHI site in the multicloning site of pAMoEC2.

pAMoEC2 (1 µg) obtained in (8) was dissolved in 30 µl of Y-100 buffer, 20 units of BamHI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end resulting from BamHI digestion to a blunt end. The reaction mixture was subjected to agarose gel electrophoresis and a DNA fragment of about 11.5 kb was recovered.

Separately, 1 µg of pBR322 [Bolivar et al.: Gene, 2, 95 (1977)] was dissolved in 30 µl of Y-50 buffer, 20 units of DraI and 20 units of PvuII were added and the digestion reaction was carried out at 37° C. for 2 hours. The reaction mixture was subjected to agarose gel electrophoresis and a DNA fragment of about 2.5 kb was recovered.

The pAMoEC2-derived BamHI (blunt end) fragment (11.5 kb; 0.1 µg) and pBR322-derived DraI-PvuII fragment (2.5 kb; 0.2 µg) obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin- and tetracycline-resistant strain was obtained. From this transformant, a plasmid was isolated by a known method. This plasmid was named pAMoEC3 and its structure was identified by digestion with restriction enzymes.

Figure 10:
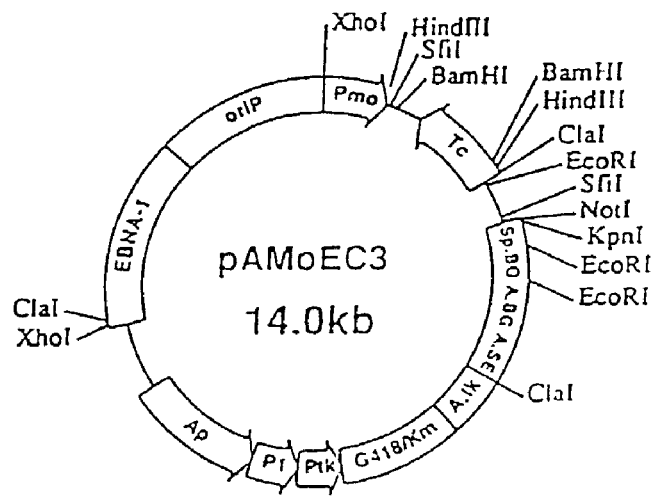
FIG. 10 shows a construction scheme for the plasmid pAMoERC3.
Figure 10:
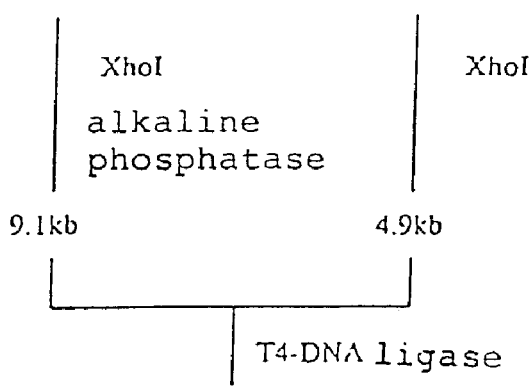
Figure 10:
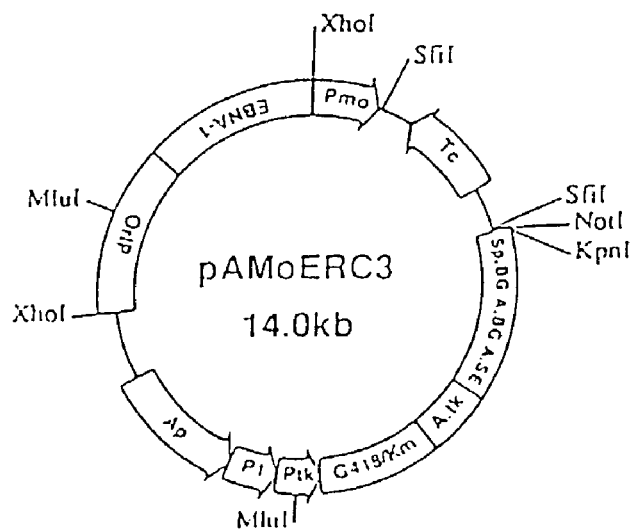

(10) Construction of pAMoERC3 (cf. FIG. 10)

A plasmid, pAMoERC3, was constructed in the manner described below by reversing the direction of the oriP and EBNA-1 gene unit in pAMoEC3.

pAMoEC3 (1 µg) obtained in (9) was dissolved in 30 µl of Y-100 buffer, 20 units of XhoI was added and the digestion reaction was carried out at 37° C. for 2 hours. Then, 30 µl of 1 M Tris-hydrochloride (pH 8.0) and 1 unit of *Escherichia coli*-derived alkaline phosphatase (Takara Shuzo) were added and the dephosphorylation reaction was carried out at 37° C. for 2 hours. After precipitation with ethanol, the precipitate was dissolved in 30 µl of a buffer comprising 10 mM Tris-hydrochloride (pH 8.0) and 1 mM EDTA (sodium ethylenediaminetetraacetate) (hereinafter "TE buffer") and subjected to agarose gel electrophoresis and a DNA fragment of about 9.1 kb was recovered.

Separately, 1 µg of the same plasmid was dissolved in 30 µl of Y-100 buffer, 20 units of XhoI was added and the digestion reaction was carried out at 37° C. for 2 hours. The reaction mixture was subjected to agarose gel electrophoresis and a DNA fragment of about 4.9 kb was recovered.

The pAMoEC3-derived XhoI fragment (9.1 kb; 0.1 µg) and the XhoI fragment (4.9 kb; 0.2 µg) derived from the same plasmid, obtained in the above manner, were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoERC3 and its structure was identified by digestion with restriction enzymes.

Figure 11:
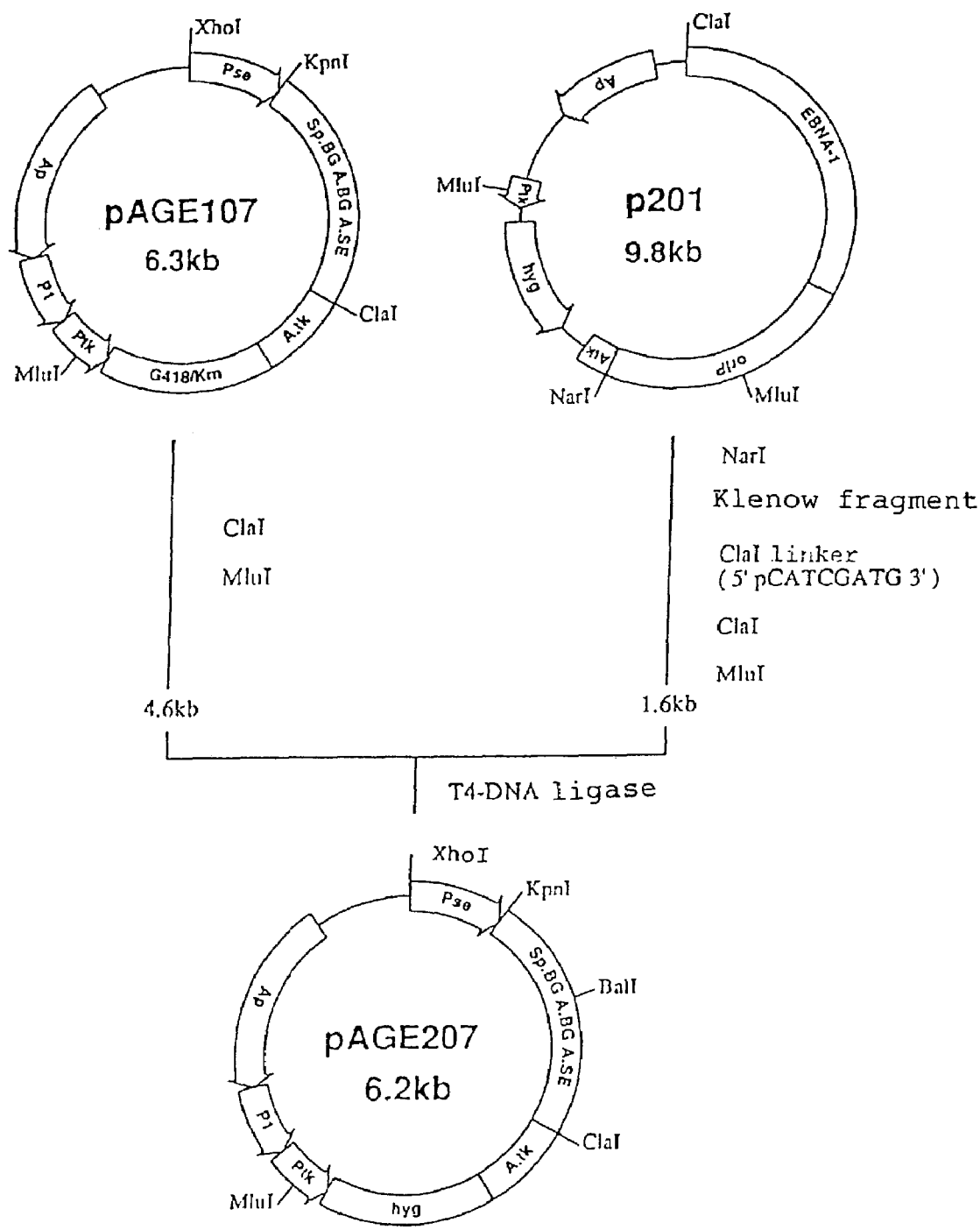
FIG. 11 shows a construction scheme for the plasmid pAGE207.

(11) Construction of pAGE207 (cf. FIG. 11)

A plasmid, pAGE207, was constructed in the manner described below by replacing the G418 resistance gene in pAGE107 with the hygromycin (hyg) resistance gene. The hyg resistance gene was excised for use from p201 [Bill Sugden et al.: Nature, 313, 812 (1985)].

pAGE107 (1 µg) was dissolved in 30 µl of Y-50 buffer, 20 units of ClaI was added and the digestion reaction was carried out at 37° C. for 2 hours. Then, sodium chloride was added to a sodium chloride concentration of 150 mM, 20 units of MluI was added and the digestion reaction was further carried out at 37° C. for 2 hours. The reaction mixture was subjected to agarose gel electrophoresis and a DNA fragment of about 4.6 kb was recovered.

p201 [Bill Sugden et al.: Nature, 313, 812 (1985); 0.5 µg] was dissolved in 30 µl of Y-50 buffer, 20 units of NarI (New England Biolabs) was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end formed upon NarI digestion to a blunt end. The reaction was terminated by extraction with phenol. After extraction with chloroform and precipitation with ethanol, the precipitate was dissolved in 20 µl of T4 ligase buffer, 0.05 µg of a ClaI linker (5' pCATCGATG 3'; Takara Shuzo) and 175 units of T4 DNA ligase were added and the ligation reaction was carried out at 12° C. for 16 hours. After precipitation with ethanol, the precipitate was dissolved in 30 µl of Y-50 buffer, 10 units of ClaI was added and the digestion reaction was carried out at 37° C. for 2 hours. Then, sodium chloride was added to a sodium chloride concentration of 150 mM, 10 units of MluI was added and, further, the digestion reaction was carried out at 37° C. for 2 hours. The reaction mixture was subjected to agarose gel electrophoresis and a DNA fragment of about 1.6 kb was recovered.

The pAGE107-derived ClaI-MluI fragment (4.6 kb; 0.2 µg) and p201-derived ClaI-MluI fragment (1.6 kb; 0.1 µg) obtained in the above manner were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAGE207 and its structure was identified by digestion with restriction enzymes.

Figure 12:
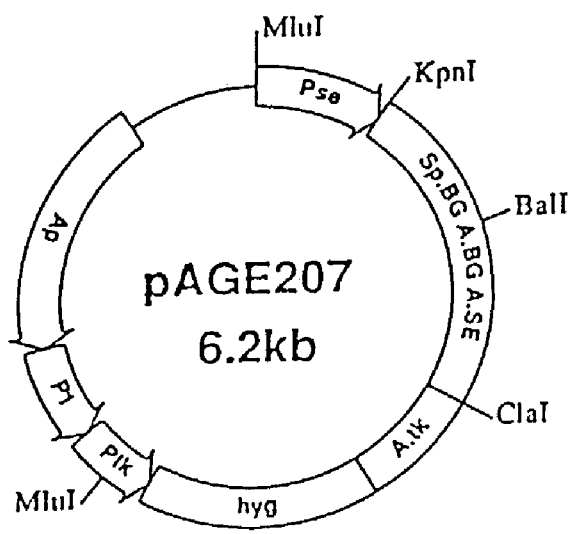
FIG. 12 shows a construction scheme for the plasmid pAGE207ScN.
Figure 12:
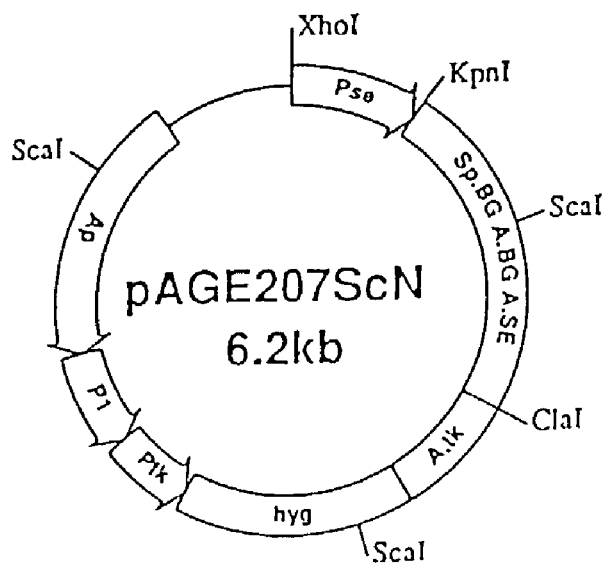

(12) Construction of pAGE207ScN (cf. FIG. 12)

For eliminating the SfiI-site-related sequence occurring in the rabbit β globin gene, a plasmid, pAGE207ScN, was constructed in the manner described below by inserting a ScaI linker into pAGE207 at the BalI site. In pAGE207ScN, the number of ScaI linkers inserted is unknown.

pAGE207 (0.5 µg) obtained in (11) was dissolved in 30 µl of Y-0 buffer, 10 units of BalI was added and the digestion reaction was carried out at 37° C. for 2 hours. After precipitation with ethanol, the precipitate was dissolved in 20 µl of T4 ligase buffer, 0.01 µg of a ScaI linker (5'pAAG-TACTT 3'; Takara Shuzo) and 175 units of T4 DNA ligase were added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAGE207ScN and its structure was identified by digestion with restriction enzymes.

Figure 13:
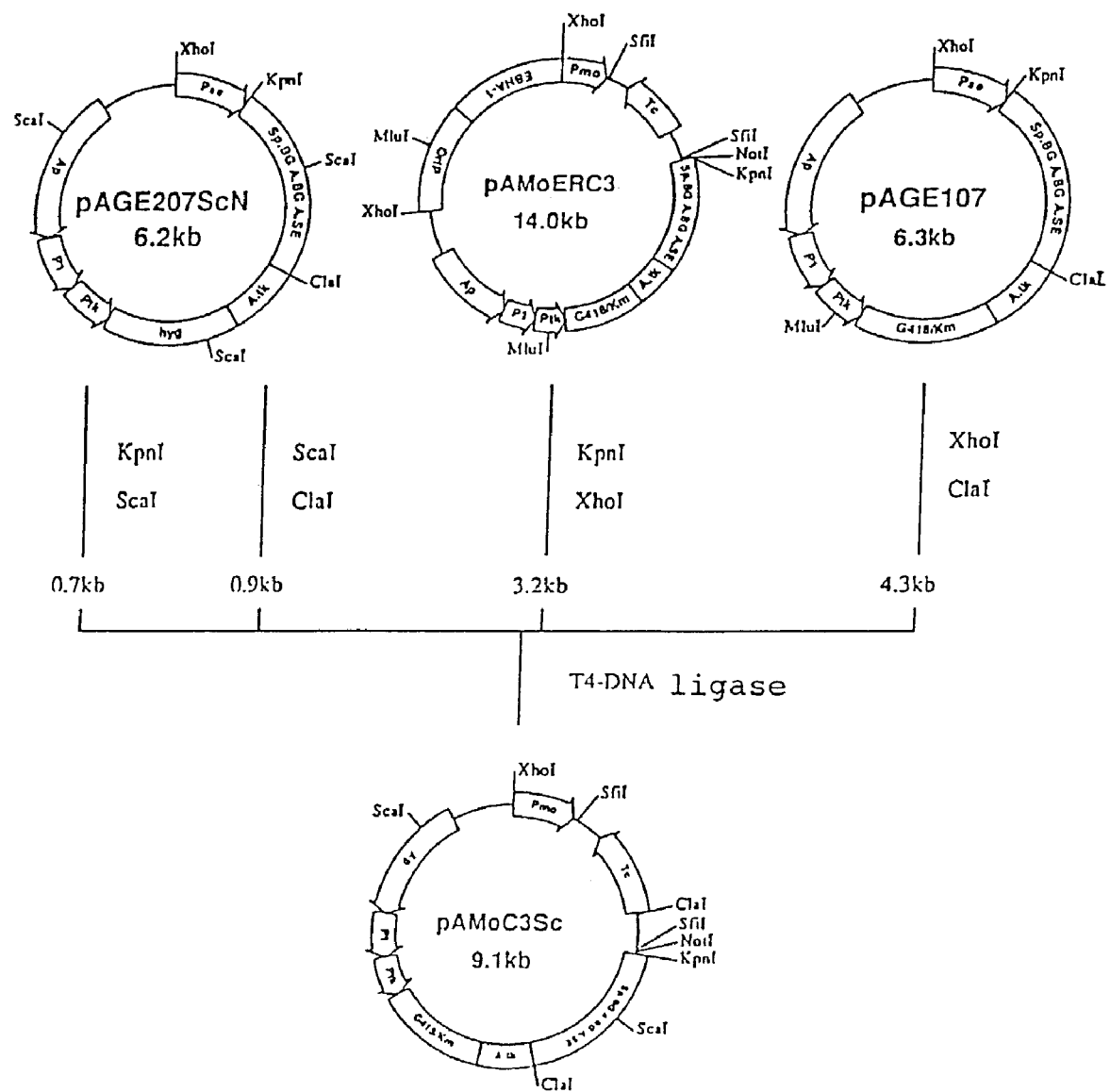
FIG. 13 shows a construction scheme for the plasmid pAMoC3Sc.

(13) Construction of pAMoC3Sc (cf. FIG. 13)

For eliminating the SfiI-site-related sequence occurring in the rabbit β globin gene in pAMoERC3, a plasmid, pAMoERC3Sc, was constructed in the manner described below by replacing the rabbit β globin gene in pAMoERC3 with the rabbit β globin gene in pAGE207ScN no longer having the related sequence in question. For convenience sake, pAMoC3Sc was first constructed and then pAMoERC3Sc was constructed. While, in the above-described pAGE207ScN, the number of ScaI linkers inserted for eliminating the SfiI-site-related sequence is unknown, in the case of pAMoERC3Sc, the number of ScaI sites inserted is presumably 1, since pAGE207ScN was once cleaved with ScaI.

pAGE207ScN (1 μg) obtained in (12) was dissolved in 30 μl of Y-0 buffer, 20 units of KpnI was added and the digestion reaction was carried out at 37° C. for 2 hours. Then, sodium chloride was added to a sodium chloride concentration of 100 mM, 20 units of ScaI was added and the digestion reaction was further carried out at 37° C. for 2 hours. The reaction mixture was subjected to agarose gel electrophoresis and a DNA fragment of about 0.7 kb was recovered.

Separately, 1 μg of the same plasmid was dissolved in 30 μl of Y-100 buffer, 20 units of ScaI and 20 units of ClaI were added and the digestion reaction was carried out at 37° C. for 2 hours. The reaction mixture was subjected to agarose gel electrophoresis and a DNA fragment of about 0.9 kb was recovered.

Further, separately, 1 μg of pAMoERC3 obtained in (10) was dissolved in 30 μl of Y-0 buffer, 20 units of KpnI was added and the digestion reaction was carried out at 37° C. for 2 hours. Then, sodium chloride was added to a sodium chloride concentration of 100 mM, 20 units of XhoI was added and the digestion reaction was further carried out at 37° C. for 2 hours. The reaction mixture was subjected to agarose gel electrophoresis and a DNA fragment of about 3.2 kb was recovered.

Then, 1 μg of pAGE107 (JP-A-2-227075) was dissolved in 30 μl of Y-100 buffer, 20 units of XhoI and 20 units of ClaI were added and the digestion reaction as carried out at 37° C. for 2 hours. The reaction mixture was subjected to agarose gel electrophoresis and a DNA fragment of about 4.3 kb was recovered.

The pAGE207ScN-derived KpnI-ScaI fragment (0.7 kb; 0.1 μg), pAGE207ScN-derived ScaI-ClaI fragment (0.9 kb; 0.1 μg), pAMoERC3-derived KpnI-XhoI fragment (3.2 kb; 0.3 μg) and pAGE107-derived XhoI-ClaI fragment (4.3 kb; 0.3 μg) respectively obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 and an ampicillin-resistant strain was obtained. From this transformant, a plasmid was isolated by a known method. This plasmid was named pAMoC3Sc and its structure was identified by digestion with restriction enzymes.

Figure 14:
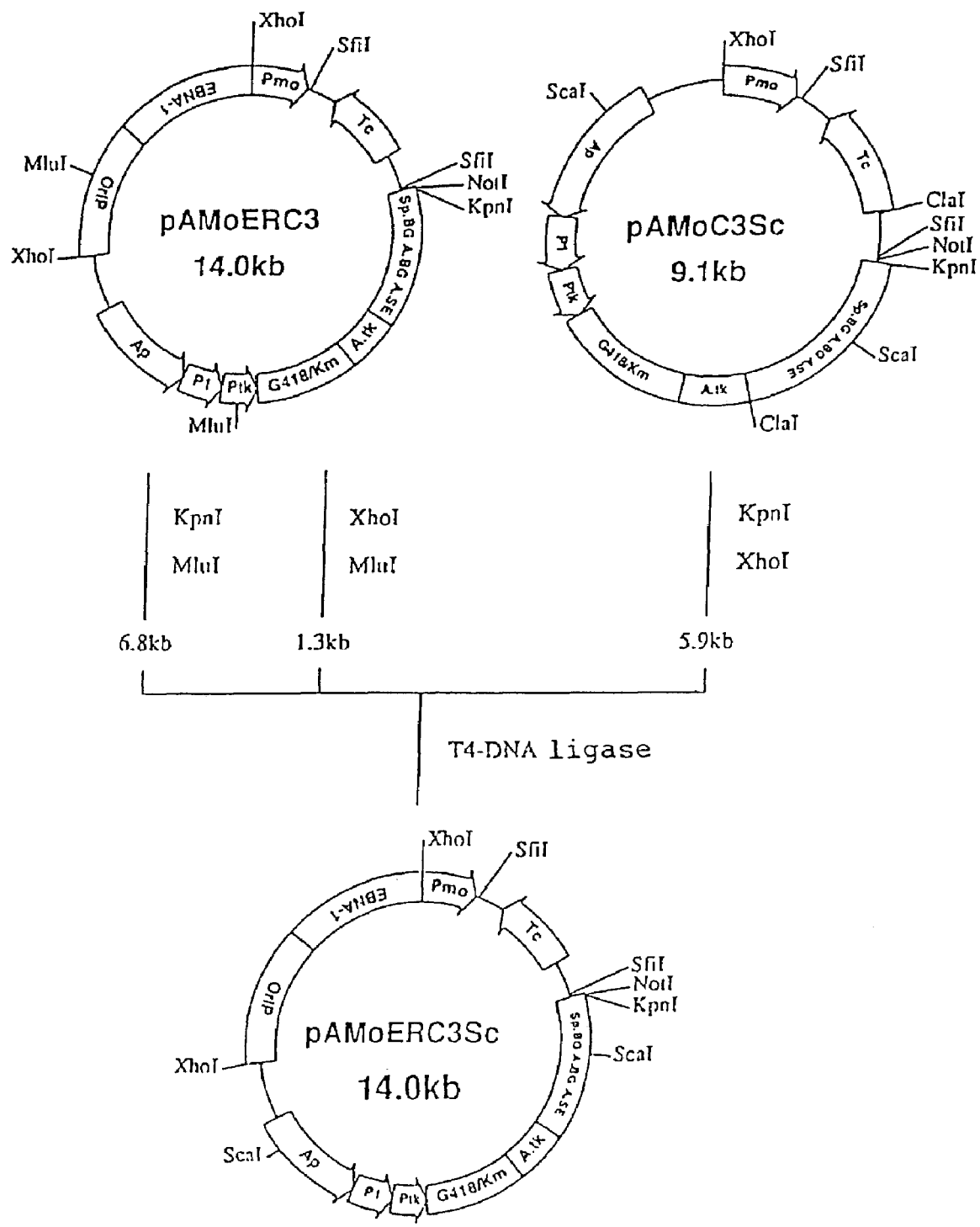
FIG. 14 shows a construction scheme for the plasmid pAMoERC3Sc.

(14) Construction of pAMoERC3Sc (cf. FIG. 14)

pAMoERC3 (1 μg) obtained in (10) was dissolved in 30 μl of Y-0 buffer, 20 units of KpnI was added and the digestion reaction was carried out at 37° C. for 2 hours. Then, sodium chloride was added to a sodium chloride concentration of 150 mM, 20 units of MluI was added and the digestion reaction was further carried out at 37° C. for 2 hours. The reaction mixture was subjected to agarose gel electrophoresis and a DNA fragment of about 6.8 kb was recovered.

Separately, 1 μg of the same plasmid was dissolved in 30 μl of Y-150 buffer, 20 units of XhoI and 20 units of MluI were added and the digestion reaction was carried out at 37° C. for 2 hours. The reaction mixture was subjected to agarose gel electrophoresis and a DNA fragment of about 1.3 kb was recovered.

Further, separately, 1 μg of pAMoC3Sc obtained in (3) was dissolved in 30 μl of Y-0 buffer, 20 units of KpnI was added and the digestion reaction was carried out at 37° C. for 2 hours. Then, sodium chloride was added to a sodium chloride concentration of 100 mM, 20 units of XhoI was added and the digestion reaction was further carried out at 37° C. for 2 hours. The reaction mixture was subjected to agarose gel electrophoresis and a DNA fragment of about 5.9 kb was recovered.

The pAMoERC3-derived KpnI-MluI fragment (6.8 kb; 0.2 μg), pAMoERC3-derived XhoI-MluI fragment (1.3 kb; 0.05 μg) and pAMoC3Sc-derived KpnI-XhoI fragment (5.9 kb; 0.2 μg) obtained as described above were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoERC3Sc and its structure was identified by digestion with restriction enzymes.

pAMoERC3Sc has the long terminal repeat of Moloney murine leukemia virus as a promoter for heterologous gene expression. Its design is such that, for efficient heterologous gene expression, the heterologous gene inserted is to be followed by the rabbit β globin gene splicing signal, rabbit β globin gene poly A addition signal and SV40 early gene poly A addition signal. Further, it has the G418 resistance gene as a drug resistance marker for animal cells and the kana mycin resistance gene (same as the G418 resistance gene) and ampicillin resistance gene as drug resistance markers for *Escherichia coli*. Further, it has the replication origin (oriP) of the Epstein-Barr virus and the EBNA-1 gene (acting trans on the oriP to induce replication), so that it can retain its plasmid state in Namalwa cells and many other cells except for rodent cells, without being incorporated into the chromosome.

cDNA library construction using pAMoERC3Sc can be realized by adding SfiI linkers to both ends of cDNA and then incorporating the addition product into pAMoERC3Sc at the SfiI site.

Figure 15:
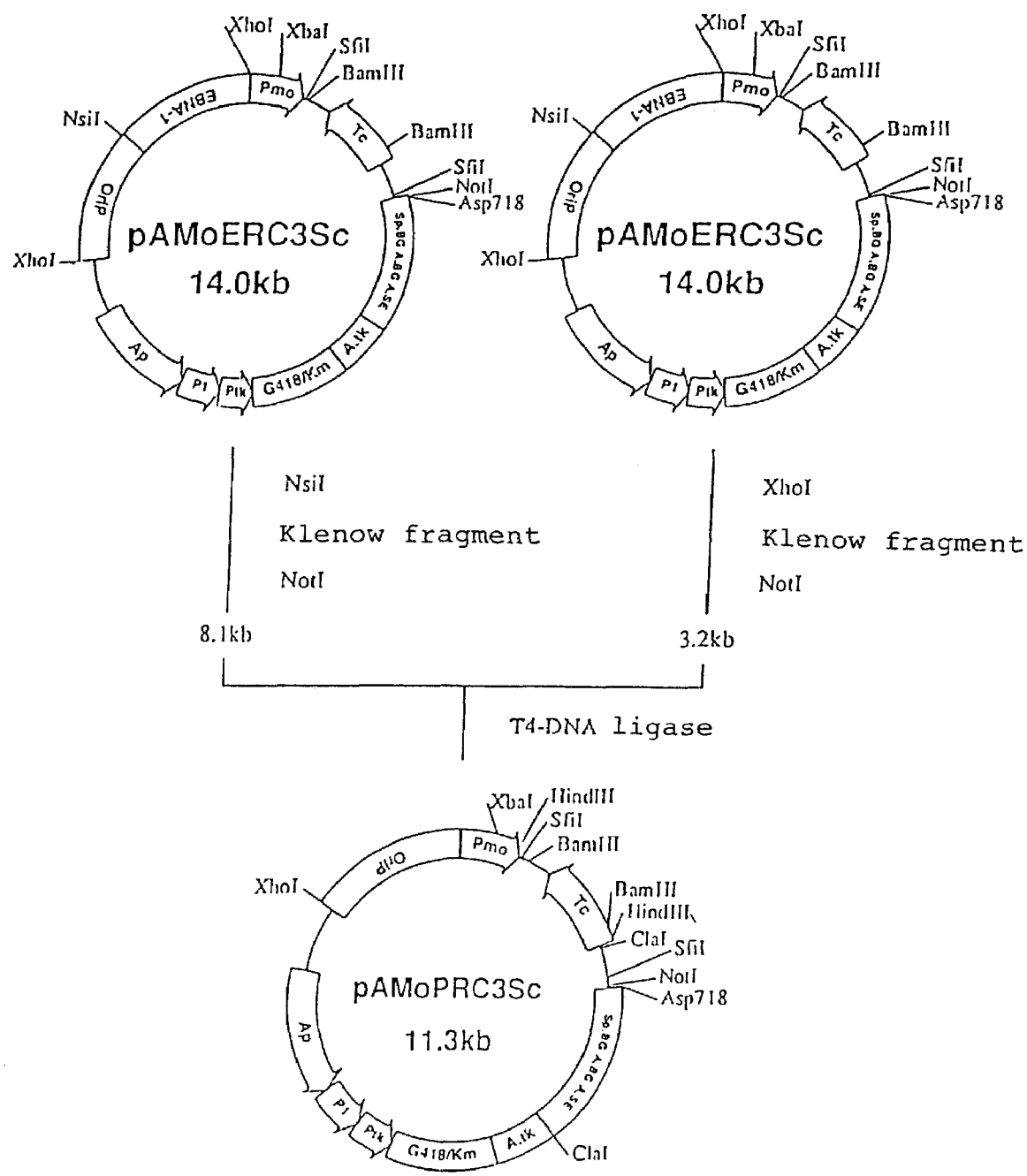
FIG. 15 shows a construction scheme for the plasmid pAMoPRC3Sc.

(15) Construction of pAMoPRC3Sc (cf. FIG. 15)

When cells expressing EBNA-1 by nature, for example Namalwa cells, are used as the host, it is supposed that the plasmid pAMoERC3Sc introduced into such host, even if it were lacking the EBNA-1 gene, could occur in the state of plasmid without being incorporated into the chromosome. Therefore, a plasmid, pAMoPRC3Sc, was constructed in the manner described below by eliminating the EBNA-1 gene from pAMoERC3Sc. Like pAMoERC3Sc, pAMoPRC3Sc can be used as a direct expression cloning vector.

pAMoERC3Sc (2 μg) obtained in (14) was dissolved in 30 μl of Y-50 buffer, 20 units of NsiI (New England Biolabs) was added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 3' cohesive end formed upon NsiI digestion to a blunt end. The reaction was terminated by extraction with phenol. After extraction with chloroform and precipitation with ethanol, the precipitate was dissolved in 30 μl of Y-100 buffer, 20 units of NotI was added and the digestion reaction was carried out at 37° C. for 2 hours. The reaction mixture was subjected to agarose gel electrophoresis and a DNA fragment of about 8.1 kb was recovered.

Separately, 2 μg of the same plasmid was dissolved in 30 μl of Y-100 buffer, 20 units of XhoI was added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 5' cohesive end formed upon XhoI digestion to a blunt end. The reaction was terminated by extraction with phenol. After extraction with chloroform and precipitation with ethanol, the precipitate was dissolved in 30 μl of Y-100 buffer, 20 units of NotI was added and the digestion reaction was carried out at 37° C. for 2 hours. The reaction mixture was subjected to agarose gel electrophoresis and a DNA fragment of about 3.2 kb was recovered.

The pAMoERC3Sc-derived NsiI(blunt end)-NotI fragment (8.1 kb; 0.1 μg) and XhoI(blunt end)-NotI fragment (3.2 kb; 0.1 μg) obtained in the above manner were dissolved in 30 μl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. From this transformant, a plasmid was isolated by a known method. This plasmid was named pAMoPRC3Sc and its structure was identified by digestion with restriction enzymes.

2. Cloning of α-2,8-sialyltransferase-Encoding cDNA (WP1)

(1) Extraction of mRNA from Cells of Human Melanoma Cell Line WM266-4

Using the mRNA extraction kit Fast Track (Invitrogen; article number K1593-02), about 30 μg of mRNA was obtained from 1×10⁸ WM266-4 cells (ATCC CRL 1676). The reagents and procedure used were as described in the manual attached to the kit.

(2) cDNA Library Construction

Using GIBCO BRL's kit cDNA Synthesis System, double-stranded cDNA was synthesized, with oligo dT as a primer, from 8 μg of the mRNA obtained in the above manner. On that occasion, GIBCO BRL's Super Script™ RNase H-Reverse Transcriptase was used as the reverse transcriptase in lieu of Moloney murine leukemia virus (M-MLV) reverse transcriptase belonging to the kit. Then, the cDNA was provided, on both ends, with the SfiI linker shown below and subjected to agarose gel electrophoresis for fractionating the cDNA by size. cDNA fragments not less than about 1.6 kb were thus recovered.

SfiI linker

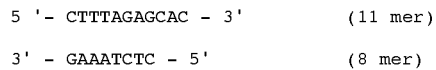

The above 11 mer (SEQ ID NO: 5) and 8 mer single-stranded DNAs were synthesized using an Applied Biosystems model 380A DNA synthesizer. Each DNA synthesized (50 μg) was individually dissolved in 50 μl of T4 kinase buffer, 30 units of T4 polynucleotide kinase (Takara Shuzo) was added and the phosphorylation reaction was carried out at 37° C. for 16 hours. The double-stranded cDNA described as mentioned above and the phosphorylated linkers (4 μg of the 11 mer and 2.9 μg of the 8 mer) phosphorylated as described above were dissolved in 45 μl of T4 ligase buffer, 1,050 units of T4 DNA ligase was added and the ligation reaction was carried out at 16° C. for 16 hours. The reaction mixture was subjected to agarose gel electrophoresis and cNDA fragments not less than about 1.6 kb in size were recovered.

Separately 24 μg of the direct expression cloning vector pAMoPRC3Sc obtained in 1-(14) was dissolved in 590 μl of Y-50 buffer, 80 units of SfiI was added and the digestion reaction was carried out at 37° C. for 16 hours. Then, a portion (5 μl) of the reaction mixture was subjected to agarose gel electrophoresis. After confirmation, in this manner, of completion of the cleavage, 40 units of BamHI was added and the digestion reaction was carried out at 37° C. for 2 hours to quantitatively reduce the background (clones without any cDNA insert) resulting from the cDNA library construction. The reaction mixture was then subjected to agarose gel electrophoresis and a DNA fragment of about 8.8 kb was recovered.

The pAMoPRC3Sc-derived SfiI fragment (8.8 kb; 2 μg) obtained as described above and the cDNA purified in the above manner were dissolved in 250 μl of T4 ligase buffer, 2,000 units of T4 DNA ligase was added and the ligation reaction was carried out at 16° C. for 16 hours. Then, after addition of 5 μg of transfer RNA (tRNA), precipitation was effected by addition of ethanol and the precipitate was dissolved in 20 μl of TE buffer. The reaction mixture was used to transform *Escherichia coli* LE392 [Maniatis et al. (editors): Molecular Cloning, second edition, Cold Spring Harbor Laboratory, 1989] by electroporation [William J. Dower et al.: Nucleic Acids Research, 16, 6127 (1988)] and about 260,000 ampicillin-resistant strains.

(3) Cloning of α-2,8-sialyltransferase-Encoding cDNA (WP1)

The ampicillin-resistant strains (about 260,000 strains; cDNA library) obtained in the above manner were mixed and plasmids were prepared using Qiagen's plasmid preparation kit>plasmid<maxi kit (article number 41031). The plasmids prepared were precipitated by addition of ethanol and then dissolved in TE buffer to a concentration of 1 μg/μl.

The above plasmid was introduced into Namalwa cells conditioned in serum-free medium (KJM-1 strain) [Hosoi et al.: Cytotechnology, 1, 151 (1988)] by electroporation [Miyaji et al.: Cytotechnology, 3, 133 (1990)]. After introduction of 4 μg of plasmid per 1.6×10⁶ cells, the cells were suspended in 8 ml of RPMI1640-ITPSGF medium [RPMI1640 medium supplemented with 1/40 volume of 7.5% NaHCO₃, 3% of 200 mM L-glutamine solution (Gibco), 0.5% of a penicillin-streptomycin solution (Gibco; 5,000 units/ml penicillin, 5,000 μg/ml streptomycin), N-2-hydroxyethylpiperazine-N'-2-hydroxypropane-3-sulfonic acid (HEPES) (10 mM), insulin (3 μg/ml), transferrin (5 μg/ml), sodium pyruvate (5 mM), sodium selenite (125 nM), galactose (1 mg/ml) and Pluronic F68 (0.1% w/v); Nissui Pharmaceutical] and cultured in a CO₂ incubator at 37° C. for 24 hours. Then, G418 (Gibco) was added to a concentration of 0.5 mg/ml and the incubation was further continued for 7 days, whereby transformants were obtained. The transformants obtained were cultured in RPMI1640-ITPSGF medium containing 0.5 mg/ml of G418 and then about 3×10⁷ cells were subjected to indirect immunofluorescent staining using an antibody against the ganglioside GD3, KM-643 (EP-A-0493686). Specifically, indirect immunofluorescent staining followed the procedure as described below.

About 3×10⁷ cells were placed in a 50-ml centrifugal tube (2059 tube; Falcon) and the cells were collected by centrifugation (130×g, 10 minutes). Then, the cells were washed with 20 ml of phosphate-buffered saline (PBS) containing 0.1% sodium azide [A-PBS; 8 g/l sodium chloride, 0.2 g/l potassium chloride, 1.15 g/l disodium hydrogen phosphate (anhydrous), 0.2 g/l potassium dihydrogen phosphate, 0.1% sodium azide]. To the cells collected was added 0.8 ml of KM-643 (10 μg/ml) for suspending the cells therein, and the reaction was carried out at 4° C. for 1 hour. The cells were rinsed with two portions of A-PBS and, then, 320 μl of anti-mouse IgG antibody and anti-mouse IgM antibody fluorescence-labeled with fluorescein isothiocyanate (FITC) (Kirkegaad & Perry Laboratories; 16-fold diluted with A-PBS) was added thereto for suspending them therein, and the reaction was carried out at 4° C. for 30 minutes. The cells were then rinsed with two portions of A-PBS and suspended in 1 ml of A-PBS and cells high in fluorescence intensity (highest 1%) were aseptically recovered using a fluorescence activated cell sorter (EPICS Elite Flow Cytometer; Coulter). The cells recovered were cultured for multiplication in RPMI1640-ITPSGF medium containing 0.5 mg/ml of G418. The cells thus grown were repeatedly treated in the same manner for separating and concentrating cells showing high fluorescence intensity. In the second, third, fourth and fifth treatments, cells with high fluorescence intensity (highest 1.5%, 3%, 3% and 8%, respectively) were recovered. As a result, cells with increased fluorescence intensity, namely cells with increased expression of the ganglioside GD3, could be obtained. These cells were cultured in RPMI1640-ITPSGF medium containing 0.5 mg/ml of G418 and then the plasmid was recovered from about 5×10⁶ cells by the Hart method [Robert F. Margolskee et al.: Molecular and Cellular Biology, 8, 2837 (1988)]. The plasmid recovered was introduced into *Escherichia coli* LE392 by electroporation [William J. Dower et al.: Nucleic Acids Research, 16, 6127 (1988)] and an ampicillin-resistant strain was obtained. From that transformant, a plasmid was prepared using Qiagen's plasmid preparation kit and its structure was studied by cleaving with various restriction enzymes. It was found that the plasmid contains a cDNA of about 2.1 kb. This plasmid was named pAMoPRWP1 and again introduced into the strain KJM-1 by the method described above. Indirect immunofluorescence staining using KM-643 revealed that the level of expression of the ganglioside GD3 was about 30 times higher in the strain KJM-1 harboring that plasmid as compared with the strain KJM-1 harboring the control plasmid (pAMoPRC3Sc). The above results indicate that cDNA is the cDNA coding for α-2,8-sialyltransferase enhancing the production of the ganglioside GD3.

Figure 16:
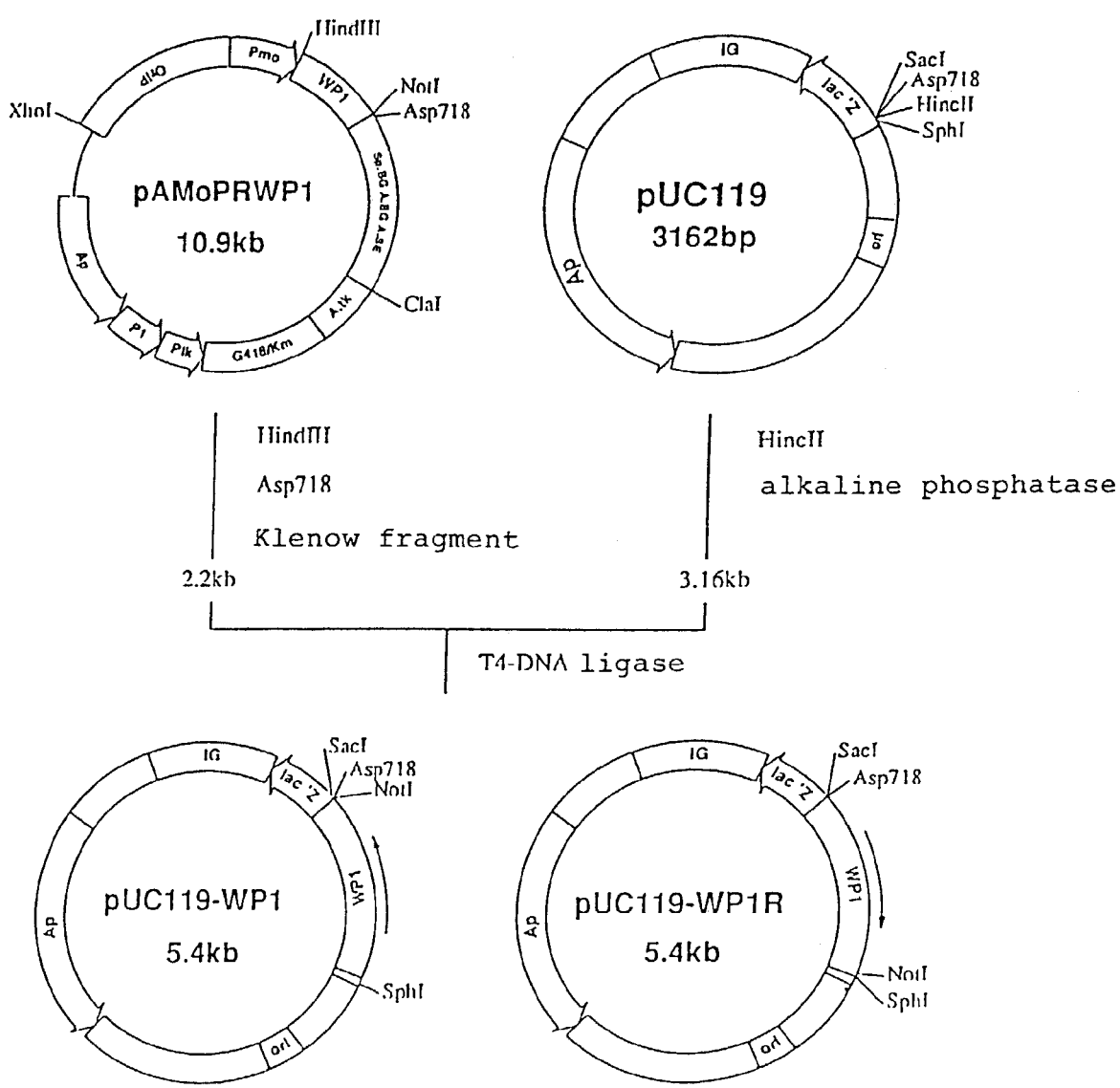
FIG. 16 shows a construction scheme for the plasmids pUC119-WP1 and pUC119-WP1R.

3. Sequencing of cDNA (WP1) Coding for α-2,8-sialyltransferase (1) Insertion of α-2,8-sialyltransferase-Encoding cDNA (WP1) into pUC119 (cf. FIG. 16)

The plasmid pAMoPRWP1 (2 μg) obtained in section 2-(3) was dissolved in 50 μl of Y-80 buffer, 30 units of HindIII and 30 units of Asp718 were added and the digestion reaction was carried out at 37° C. for 2 hours. After precipitation with ethanol, the precipitate was dissolved in 30 μl of DNA polymerase I buffer, 6 units of *Escherichia coli*-derived DNA polymerase I Klenow fragment was added and the reaction was carried out at 37° C. for 60 minutes to convert the 5' cohesive end formed upon HindIII digestion and the 5' cohesive end formed upon Asp718 digestion respectively to blunt ends. The reaction mixture was subjected to agarose gel electrophoresis and a DNA fragment of about 2.2 kb was recovered.

Separately, 1 μg of pUC119 [Messing et al.: Methods in Enzymology, 153, 3 (1987)] was dissolved in 30 μl of Y-100 buffer, 20 units of HincII was added and the digestion reaction was carried out at 37° C. for 2 hours. Then, 30 μl of 1 M Tris-hydrochloride (pH 8.0) and 1 unit of *Escherichia coli*-derived alkaline phosphatase (Takara Shuzo) were added and the de phosphorylation reaction was carried out at 37° C. for 2 hours. After precipitation with ethanol, the precipitate was dissolved in 30 μl of TE buffer and subjected to agarose gel electrophoresis and a DNA fragment of about 3.16 kb was recovered.

The pAMoPRW P1-derived HindIII (blunt end)-Asp718 (blunt end) fragment (2.2 kb; 0.05 μg) and pUC119-derived HincII fragment (3.16 kb; 0.05 μg) obtained in the above manner were dissolved in 30 μl of T4 ligase buffer, 175 units of T4 DNA ligase was added and the ligation reaction was carried out at 12° C. for 16 hours.

The reaction mixture was used to transform *Escherichia coli* JM105 [Yanisch-Perron et al.: Gene, 33, 103 (1985)] by the method of Cohen et al. and ampicillin-resistant strains were obtained. Plasmids were isolated from these transformant strains by known methods and their structures were identified by digestion with restriction enzymes. Two plasmids differing in the direction in pUC119 of the pAMo-PRWP1-derived HindIII (blunt end)-Asp718 (blunt end) fragment were isolated. The plasmids were named pUC119-WP1 and pUC119-WP1R, respectively.

(2) Construction of Deletion-Mutated Plasmids for Sequencing

The whole base sequence of the α-2,8-sialyltransferase-encoding cDNA (WP1) was determined by the following procedure.

pUC119-WP1R (2 μg) was dissolved in 30 μl of Y-0 buffer, 40 units of SacI was added and the digestion reaction was carried out at 37° C. for 16 hours. Then, sodium chloride was added to a sodium chloride concentration of 80 mM, 40 units of Asp718 was added and the digestion reaction was further carried out at 37° C. for 2 hours. After precipitation with ethanol, the precipitate was dissolved in 100 μl of ExoIII buffer (attached to Takara Shuzo's deletion kit for kilosequencing).

Separately, 2 μg of the same plasmid pUC119-WP1R was dissolved in 30 μl of Y-150 buffer, 40 units of SphI and 40 units of NotI were added and the digestion reaction was carried out at 37° C. for 16 hours. After precipitation with ethanol, the precipitate was dissolved in 100 μl of ExoIII buffer (attached to Takara Shuzo's deletion kit for kilosequencing).

Starting with the pUC119-WP1R-derived SacI-Asp718 fragment and pUC119-WP1R-derived SphI-NotI fragment obtained in the above manner, a total of 13 deletion mutation plasmids were prepared using Takara Shuzo's deletion kit for kilosequencing. The reagents and procedure actually employed were those described in the manual attached to the kit.

The base sequences of the deletion-mutated plasmids obtained in the above manner were determined using Applied Biosystems' sequencing kit (Taq DyeDeoxy™ Terminator Cycle Sequencing Kit; article number 401113). The sequence of the segment that could not be deter mined by using the deletion-mutated plasmids described ed above was determined by using, as primers, DNAs synthesized based on the base sequence determined by using the deletion-mutated plasmids. The base sequence of WP1 thus determined is shown under SEQ ID NO:1. It was revealed that WP1 codes for a protein composed of 356 amino acid residues. The amino acid sequence indicated that the protein has a structure common to glycosyltransferases (GT). Thus, apparently, the protein has a structure such that the N-terminal 27 amino acid residues are in the cytoplasm, the succeeding highly hydrophobic region composed of 22 amino acid residues are membrane bound and exposes the remaining C-terminal portion (including the site of catalysis) is present in the Golgi body. Comparison of that amino acid sequence with the known amino acid sequences of glycosyltransferases revealed that the protein is partially homologous to two species of α-2,3-sialyltransferase [Dawn X. Wen et al.: Journal of Biological Chemistry, 267, 21011 (1992); William Gillespie et al.: Journal of Biological Chemistry, 267, 21004 (1992)] and α-2,6-sialyltransferase [Jasminder Weinstein et al.: Journal of Biological Chemistry, 262, 17735 (1987)]. Based on the findings that expression of WP1 in Namalwa cells results in increased expression of the ganglioside GD3, that the protein encoded by WP1 is homologous to sialyltransferases and that the protein encoded by WP1 differs in amino acid sequence from the known sialyltransferase species, it is considered that WP1 codes for a novel sialyltransferase species.

Namalwa cells used as the host allow the expression of the ganglioside GM3 but do not allow the expression of the ganglioside GD3. The ganglioside GD3 is formed from the ganglioside GM3 upon further addition of a sialic acid residue to the terminal sialic acid residue of GM3 via α-2,8 linkage. An enzyme that catalyzes this reaction is α-2,8-sialyltransferase. Therefore, in view of the above results, it is considered that WP1 codes for α-2,8-sialyltransferase.

EXAMPLE 2

Synthesis of Ganglioside GD3 in KJM-1 Strain Harboring α-2,8-sialyltransferase Expression Plasmid The plasmids pAMoPRC3Sc (direct expression cloning vector; control) and pAMoPRWP1 (α-2,8-sialyltransferase expression plasmid) were prepared using Qiagen's plasmid preparation kit>plasmid<maxi kit (article number 41031). The plasmids obtained were precipitated with ethanol and then dissolved in TE buffer to a concentration of 1 µg/µl. Then, each plasmid was introduced into Namalwa KJM-1 cells by the technique of electroporation [Miyaji et al.: Cytotechnology, 3, 133 (1990)]. After introduction of 4 µg of plasmid per $1.6 \times 10^6$ cells, the cells were suspended in 8 ml of RPMI1640-ITPSGF medium and cultured in a carbon dioxide incubator at 37° C. for 24 hours. Then, G418 (Gibco) was added to a concentration of 0.5 mg/ml and incubation was continued for 7 days. Then, 22 ml of RPMI1640-ITPSGF medium (containing 0.5 mg/ml of G418) was added and incubation was further continued for 5 days. The thus-obtained transformants were cultured in RPMI1640-ITPSGF medium containing 0.5 mg/ml of G418. About $1 \times 10^6$ cells were placed in a microtube (1.5 ml; Eppendorf) and cells were collected by centrifugation (550× g, 7 minutes). The cells were then washed with 1 ml of phosphate-buffered saline (PBS) containing 0.1% of sodium azide (A-PBS; 8 g/l sodium chloride, 0.2 g/l potassium chloride, 1.15 g/l disodium hydrogen phosphate (anhydrous), 0.2 g/l potassium dihydrogen phosphate, 0.1% sodium azide). The cells collected were subjected to indirect immunofluorescent staining using KM-643 (EP-A-0493686), an antibody to the ganglioside GD3, for checking the expression of the ganglioside GD3 in these cells. Thus, 50 µl (10 µg/ml) of KM-643 was added to each lot of the cells collected for causing the cells to be suspended therein, and the reaction was carried out at 4° C. for 1 hour. The cells were washed with three portions of A-PBS, 20 µl of fluorescein isothiocyanate (FITC)-labeled anti-mouse IgG antibody and IgM antibody (product of Kirkegaad & Perry Laboratories; 16-fold diluted with A-PBS) was added for suspending the cells, and the reaction was carried out at 4° C. for 30 minutes. The cells were washed with three portions of A-PBS, again suspended in A-PBS and subjected to analysis using an EPICS Elite flow cytometer (Coulter). As a control, the same procedure as described above was followed using normal mouse serum (500-fold diluted with A-PBS) in lieu of KM-643.

Figure 17:
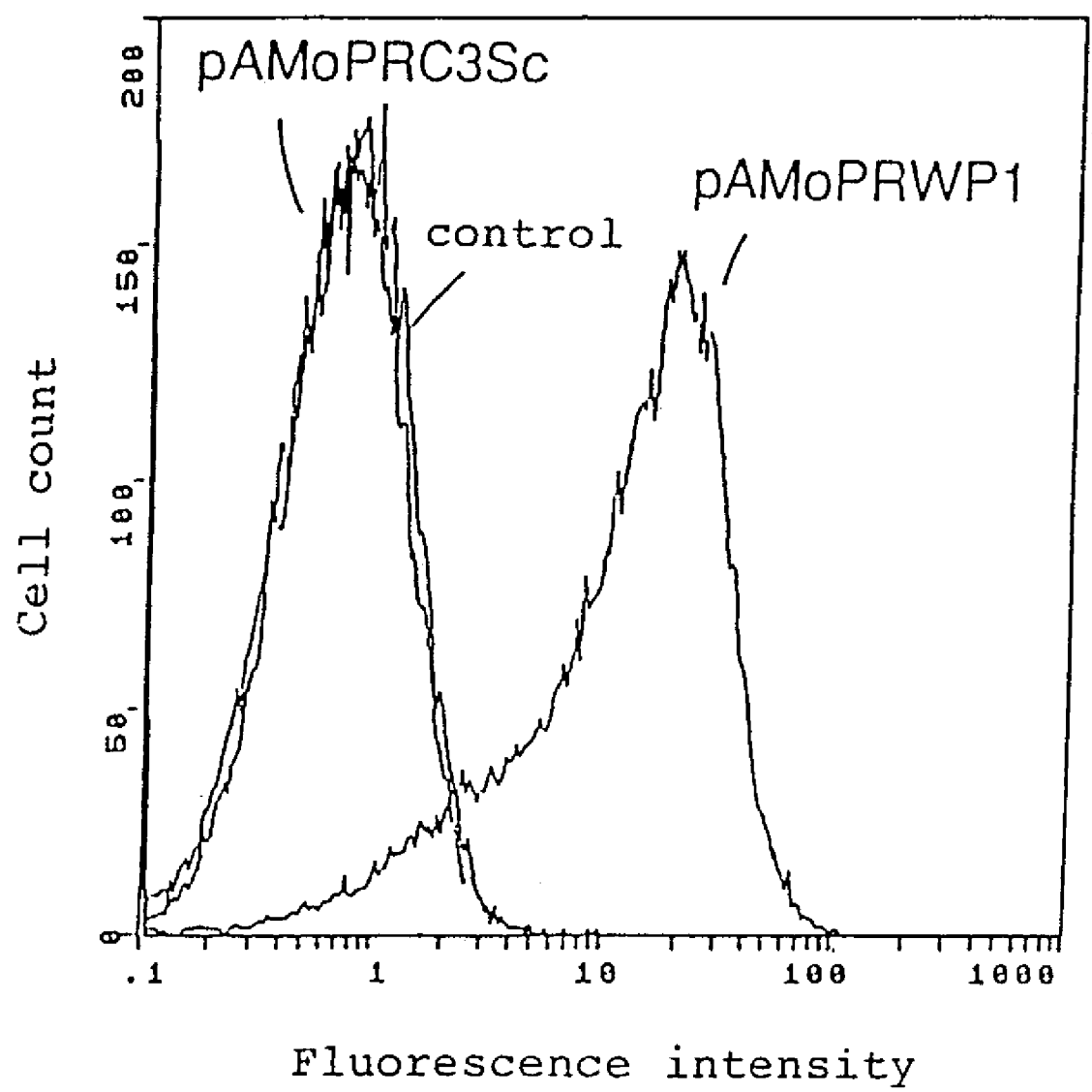
FIG. 17 shows the results of analysis on an EPICS Elite flow cytometer (Coulter) following indirect immunofluorescent staining of the KJM-1 strain after introduction therein of pAMoPRC3Sc (control plasmid) or pAMoPRWP1 (α-2, 8-sialyltransferase expression plasmid) using KM-643. The results obtained by subjecting the KJM-1 strain after introduction therein of pAMoPRC3Sc (control plasmid) to indirect immunofluorescent staining using normal mouse serum are shown as a control.

The results thus obtained are shown in FIG. 17. In the KJM-1 cells after introduction of the direct expression cloning vector pAMoPRC3Sc (control plasmid), the fluorescence intensity of cells stained with KM-643 was approximately the same as the fluorescence intensity in the control, confirming that there was no expression of the ganglioside GD3 in the KJM-1 cells. The fluorescence intensity of the KJM-1 cells harboring pAMoPRWP1 (α-2,8-sialyl transferase expression plasmid) as stained with KM-643 was found to be about 25 times higher as compared with the fluorescence intensity of the KJM-1 cells harboring pAMoPRC3Sc (control plasmid) as stained with KM-643. The above results indicate that the ganglioside GD3 can be newly synthesized by causing intracellular expression of α-2,8-sialyltransferase encoded by WP1.

EXAMPLE 3

Secretory Production of α-2,8-sialyltransferase

Figure 18:
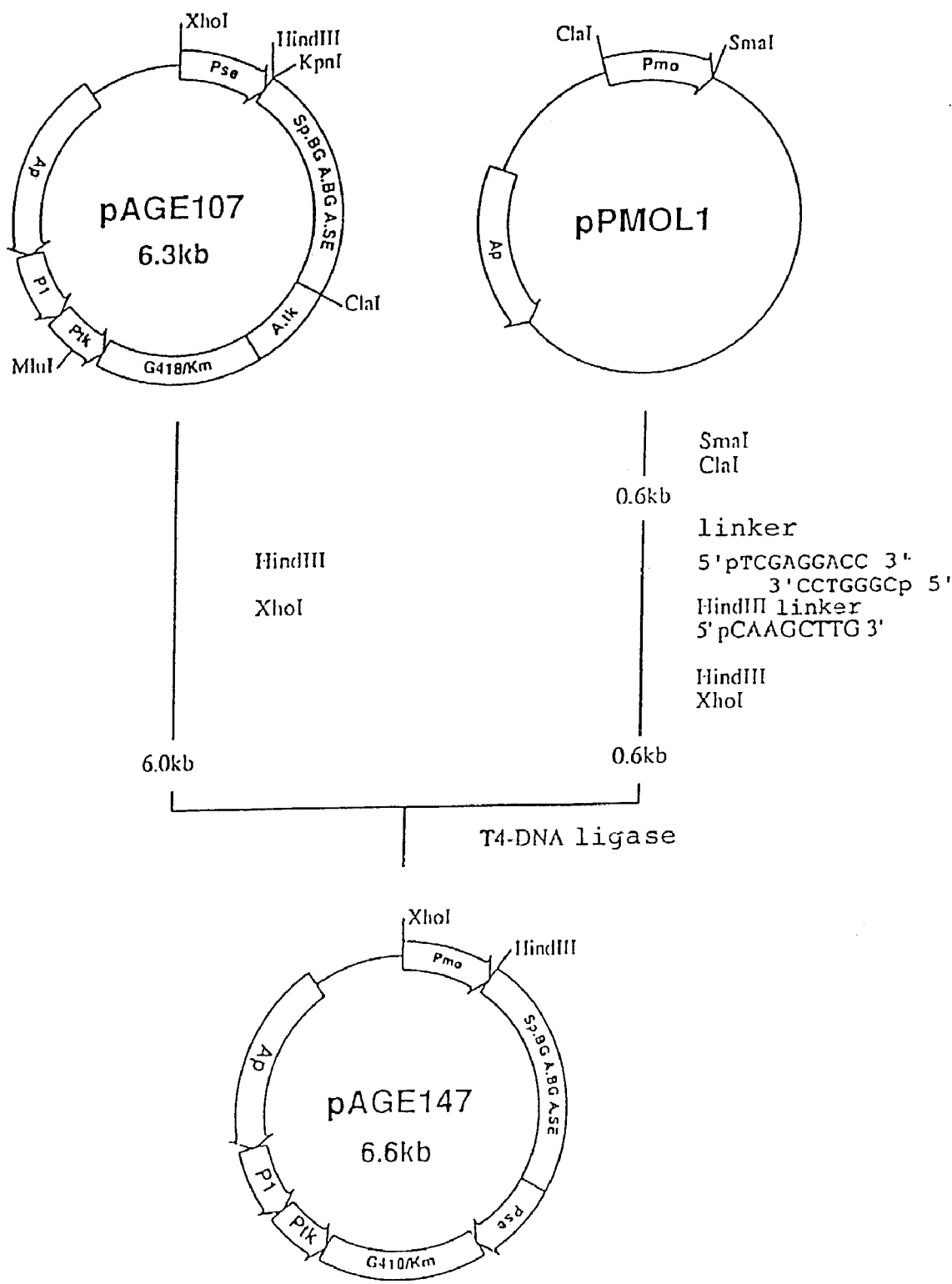
FIG. 18 shows a construction scheme for the plasmid pAGE147.

1. Construction of Secretory Expression Vector pAMoPRSA (1) Construction of pAGE147 (cf. FIG. 18)

A plasmid, pAGE147, was constructed by replacing the SV40 early gene promoter of pAGE107 with the long terminal repeat (hereinafter LTR) promoter of the Moloney murine leukemia virus. The plasmid pPMOL1 (JP-A-1-63394; 2 µg) was dissolved in 30 µl of Y-0 buffer, 20 units of SmaI was added and the digestion reaction was carried out at 30° C. for 3 hours. Then, sodium chloride was added to a concentration of 50 mM, 20 units of ClaI was added and the digestion reaction was carried out at 37° C. for 2 hours. The reaction mixture was subjected to agarose gel electrophoresis and a DNA fragment (about 0.6 kb) containing the LTR promoter of the Moloney murine leukemia virus was recovered.

Separately, 25 picomoles (pmoles) each of the two DNA linkers synthesized in Example 1, section 1-(8) were dissolved in 10 µl of T4 kinase buffer, 5 units of T4 DNA kinase was added and the reaction was carried out at 37° C. for 30 minutes for the phosphorylation at the 5' end.

The pPMOL1-derived ClaI-SmaI fragment (0.6 kb; 0.05 µg) and two 5'-phosphorylated synthetic DNAs (1 picomole each) respectively obtained as described above and a HindIII linker (5'-pCAAGCTTG-3'; Takara Shuzo; 1 picomole) were dissolved in 30 µl of T4 ligase buffer, 200 units of T4 DNA ligase was added and the ligation reaction was carried out at 12° C. for 16 hours. The resulting DNA fragment was recovered by precipitation with ethanol and dissolved in Y-100 buffer, 10 units of HindIII and 10 units of XhoI were added and the digestion reaction was carried out at 37° C. for 2 hours. The reaction was terminated by extraction with phenol and chloroform and the DNA fragment was recovered by precipitation with ethanol.

Separately, 1 µg of pAGE107 [JP-A-3-22979; Miyaji et al.: Cytotechnology, 3, 133 (1990)] was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 6.0 kb) containing the G418 resistance gene and ampicillin resistance gene was recovered.

The pAGE107-derived HindIII-XhoI fragment (6.0 kb; 0.3 µg) and pPMOL1-derived HindIII-XhoI fragment (0.6 kb; 0.01 µg) obtained as described above were dissolved in 20 µl of T4 ligase buffer, 200 units of T4 DNA ligase was added and the ligation reaction was carried out at 12° C. for 16 hours.

The reaction mixture was used to transform *Escherichia coli* HB101 by the method of Cohen et al. and an ampicillin resistant strain was obtained. A plasmid was isolated from this transformant by a known method. This plasmid was named pAGE147 and its structure was identified by digestion with restriction enzymes.

Figure 19:
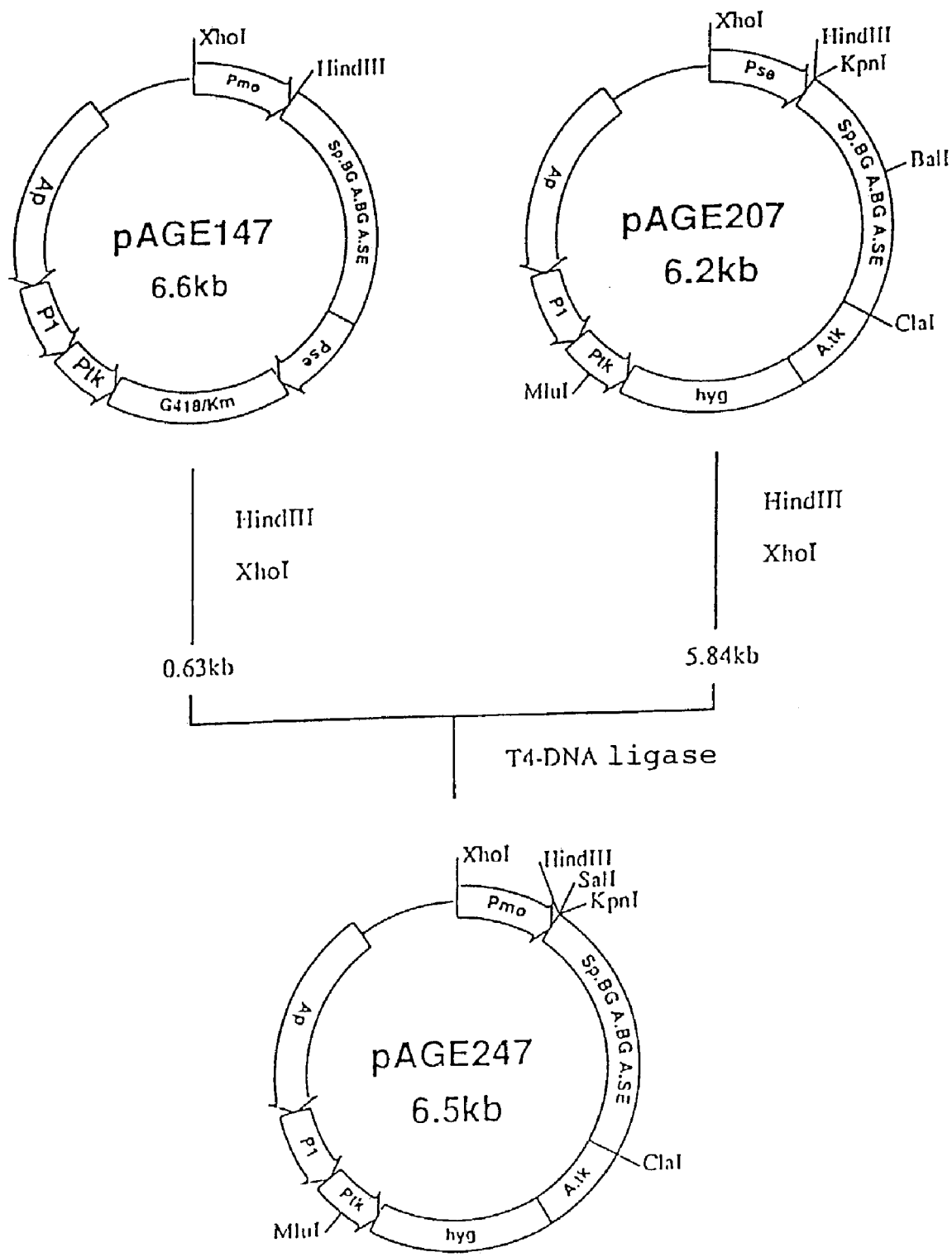
FIG. 19 shows a construction scheme for the plasmid pAGE247.

(2) Construction of pAGE247 (cf. FIG. 19)

A plasmid, pAGE247, was constructed in the manner described below by replacing the SV40 early gene promoter of pAGE207 with the LTR promoter of the Moloney murine leukemia virus.

pAGE147 (2 µg) obtained above was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 0.63 kb) containing the Moloney murine leukemia virus LTR promoter was recovered. Separately, pAGE207 (2 µg) constructed in Example 1, section 1-(11) was dissolved in 30 µl of Y-100 buffer, 10 units of HindIII and 10 units of XhoI were added and the digestion reaction was carried out at 37° C. for 2 hours. The reaction mixture was subjected to agarose gel electrophoresis and a DNA fragment (about 5.84 kb) containing the Hygromycin resistance gene and ampicillin resistance gene was recovered.

The pAGE147-derived HindIII-XhoI fragment (0.63 kb; 0.05 µg) and pAGE207-derived HindIII-XhoI fragment (5.84 kb; 0.1 µg) obtained as described above were dissolved in 30 µl of T4 ligase buffer, 100 units of T4 DNA ligase was added and the ligation reaction was carried out at 12° C. for 16 hours.

The reaction mixture was used to transform *Escherichia coli* HB101 by the method of Cohen et al. and an ampicillin-resistant strain was obtained. A plasmid was isolated from this transformant by a known method. This plasmid was named pAGE247 and its structure was identified by digestion with restriction enzymes.

Figure 20:
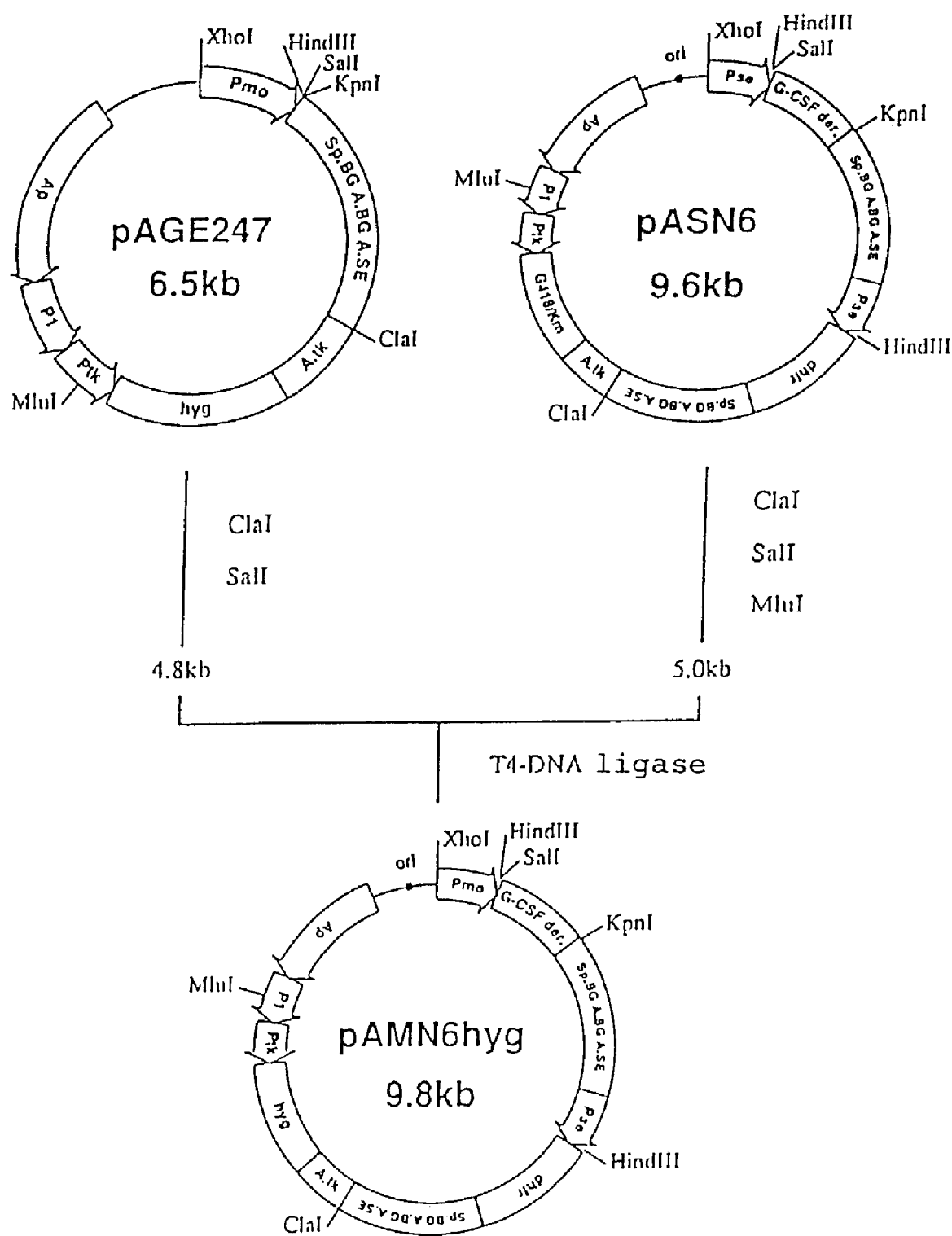
FIG. 20 shows a construction scheme for the plasmid pAMN6hyg.

(3) Construction of pAMN6hyg (cf. FIG. 20)

An expression plasmid, pAMN6hyg, for a human granulocyte colony stimulating factor derivative was constructed with the Moloney murine leukemia virus LTR as a promoter and the hygromycin resistance gene as a marker, as follows.

pAGE247 (2 µg) obtained as described above was dissolved in 30 µl of Y-50 buffer, 20 units of ClaI was added and the digestion reaction was carried out at 37° C. for 2 hours. Then, sodium chloride was added to a concentration of 175 mM, 20 units of SalI was added and the digestion reaction was carried out at 37° C. for 2 hours. The reaction mixture was subjected to agarose gel electrophoresis and a DNA fragment (about 4.8 kb) containing the Moloney murine leukemia virus LTR promoter, ampicillin resistance gene and hygromycin resistance gene was recovered.

Separately, the plasmid pASN6 (2 µg) obtained by the method disclosed in JP-A-2-227075 was dissolved in 30 µl of Y-50 buffer, 20 units of ClaI was added and the digestion reaction was carried out at 37° C. for 2 hours. Then, sodium chloride was added to a concentration of 175 mM, 20 units of SalI and 20 units of MluI were added and the digestion reaction was carried out at 37° C. for 2 hours. The reaction mixture was subjected to agarose gel electrophoresis and a DNA fragment (about 5.0 kb) containing the human granulocyte colony stimulating factor derivative gene was recovered.

The pAGE247-derived ClaI-SalI fragment (4.8 kb; 0.1 µg) and pASN6-derived ClaI-SalI fragment (5.0 kb; 0.1 µg) obtained as described above were dissolved in 20 µl of T4 ligase buffer, 200 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant by a known method. This plasmid was named pAMN6hyg and its structure was identified by digestion with restriction enzymes.

Figure 21:
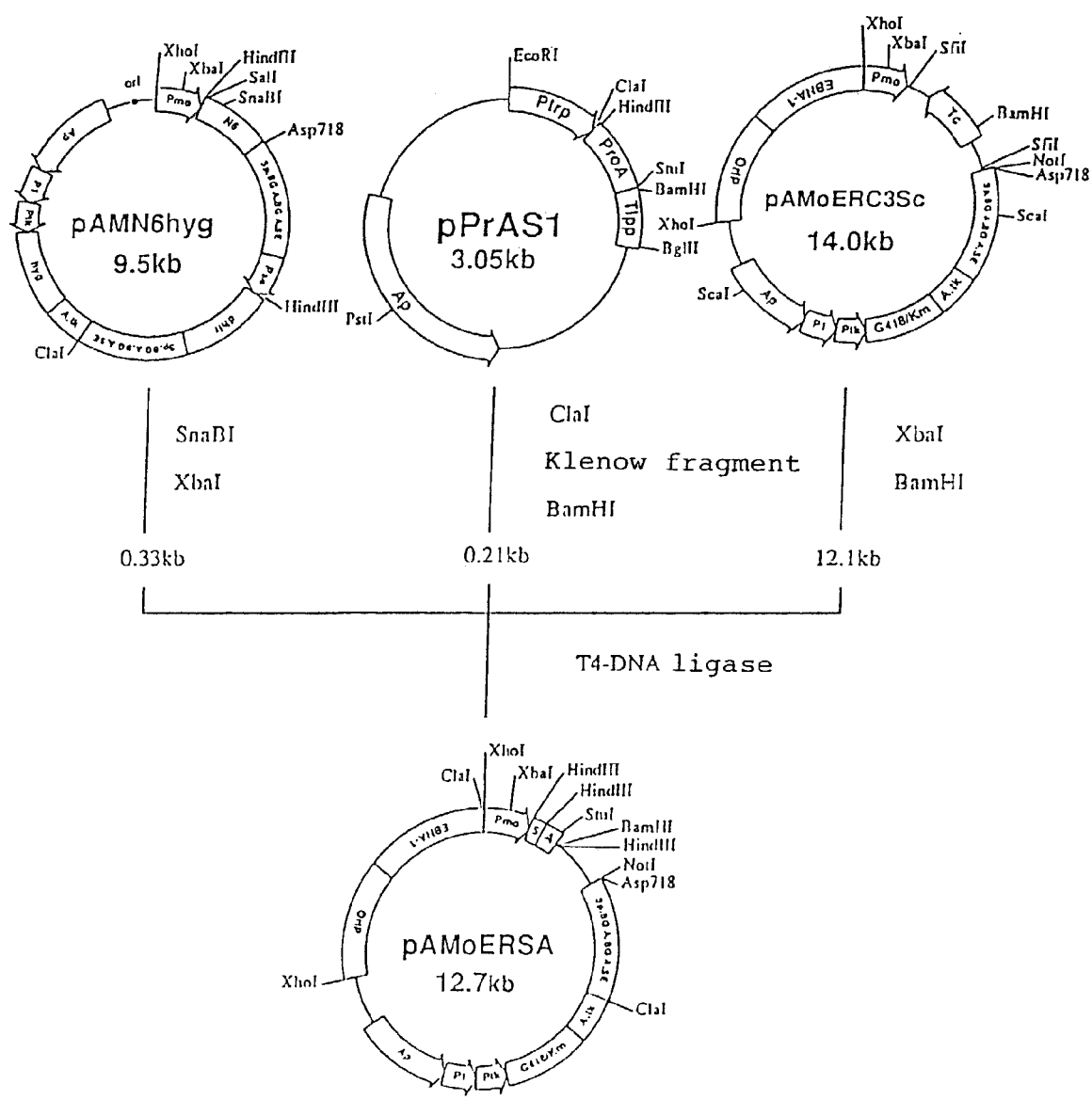
FIG. 21 shows a construction scheme for the plasmid pAMoERSA.

(4) Construction of pAMoERSA (cf. FIG. 21)

A vector, pAMoERSA, for secretory expression of α-2, 8-sialyltransferase in a form fused to the immunoglobulin G (IgG) binding region of *Staphylococcus aureus* protein A was constructed in the following manner.

pAMN6hyg (2 µg) obtained above was dissolved in 30 µl of Y-50 buffer, 20 units of SnaBI was added and the digestion reaction was carried out at 37° C. for 2 hours. Then, sodium chloride was added to a concentration of 100 mM, 20 units of XbaI was added and the digestion reaction was carried out at 37° C. for 2 hours. The reaction mixture was subjected to agarose gel electrophoresis and a DNA fragment (about 0.33 kb) containing the human granulocyte colony stimulating factor signal sequence was recovered.

Separately, 2 µg of pPrAS1 [Saito et al.: Protein Engineering, 2, 481 (1989)] was dissolved in 30 µl of Y-50 buffer, 20 units of ClaI was added and the digestion reaction was carried out at 37° C. for 2 hours. After precipitation with ethanol, the precipitate was dissolved in 30 µl of DNA polymerase I buffer, 6 units of *Escherichia coli*-derived DNA polymerase I Klenow fragment was added and the reaction was carried out at 37° C. for 60 minutes to convert the 5' cohesive end formed upon ClaI digestion to a blunt end. The reaction was terminated by extraction with phenol. After extraction with chloroform and precipitation with ethanol, the precipitate was dissolved in 30 µl of Y-100 buffer, 20 units of BamHI was added and the digestion reaction was carried out at 37° C. for 2 hours. The reaction mixture was subjected to agarose gel electrophoresis and a DNA fragment (about 0.21 kb) containing the IgG binding region of protein A was recovered.

Further, separately, 2 µg of pAMoERC3Sc obtained in Example 1, section 1-(13) was dissolved in 30 µl of Y-100 buffer, 20 units of XbaI and 20 units of BamHI were added and the digestion reaction was carried out at 37° C. for 2 hours. The reaction mixture was subjected to agarose gel electrophoresis and a DNA fragment of about 12.1 kb was recovered.

The pAMN6hyg-derived SnaBI-XbaI fragment (0.33 kb; 0.05 µg), pPrAS1-derived ClaI (blunt end)-BamHI fragment (0.21 kb; 0.05 µg) and pAMoERC3Sc-derived XbaI-BamHI fragment (12.1 kb; 0.1 µg) obtained as described above were dissolved in 30 µl of T4 ligase buffer, 175 units of T4 DNA ligase was added and the ligation reaction was carried out at 12° C. for 16 hours.

The reaction mixture was used to transform *Escherichia coli* HB101 by the method of Cohen et al. and an ampicillin-resistant strain was obtained. A plasmid was isolated from this transformant by a known method. This plasmid was named pAMoERSA and its structure was identified by digestion with restriction enzymes.

Figure 22:
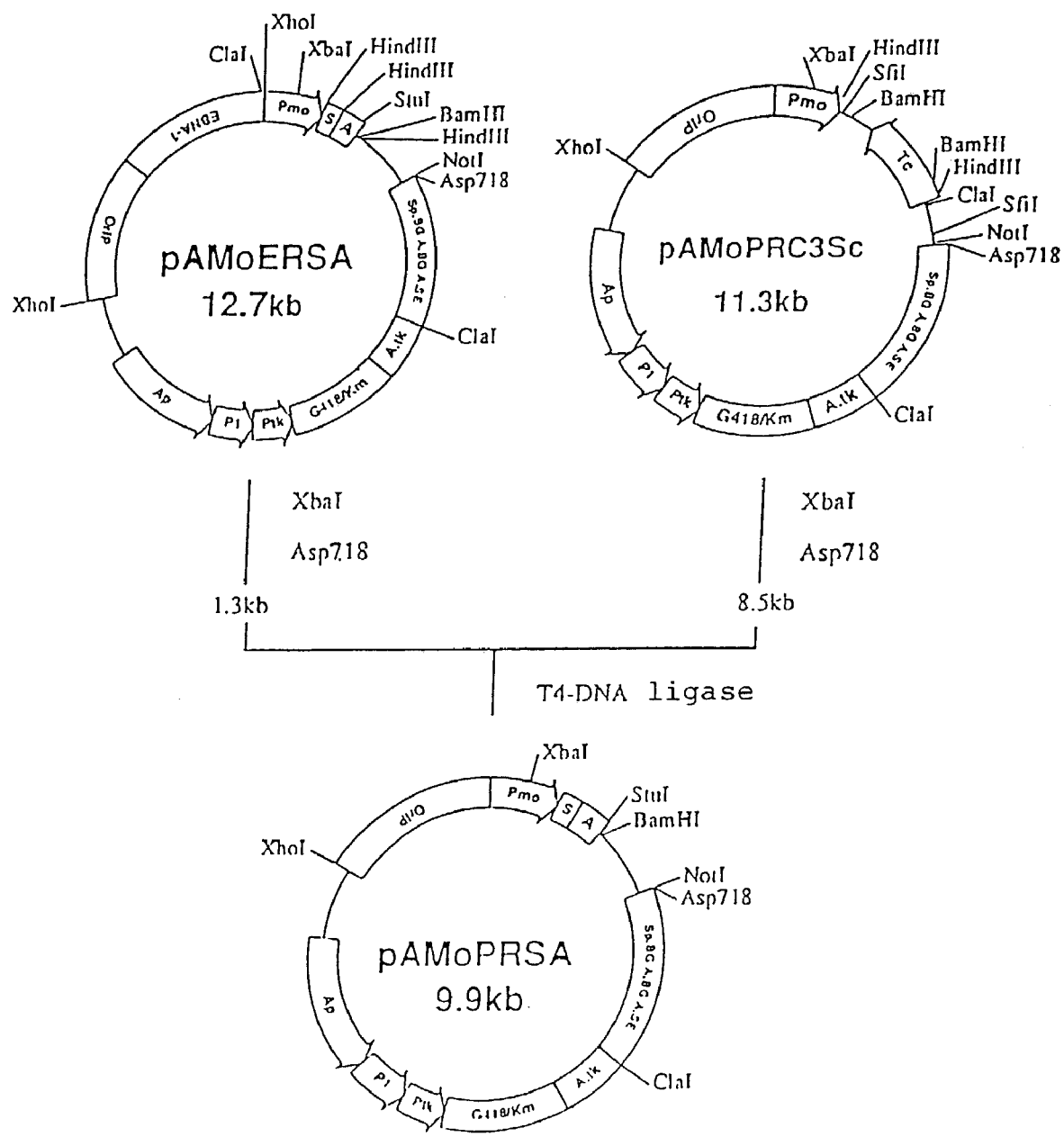
FIG. 22 shows a construction scheme for the plasmid pAMoPRSA.

(5) Construction of pAMoPRSA (cf. FIG. 22)

A plasmid, pAMoPRSA, was constructed by eliminating the EBNA-1 gene from pAMoERSA as follows. Like pAMoERSA, pAMoPRSA can be used as a secretory expression vector.

pAMoERSA (2 µg) was dissolved in 30 µl of a buffer comprising 10 mM Tris-HCl (pH 7.5), 6 mM MgCl 2, 80 mM NaCl and 6 mM 2-mercaptoethanol (herein after "Y-80 buffer"), 20 units of XbaI and 20 units of Asp718 (Boehringer Mannheim) were added and the digestion reaction was carried out at 37° C. for 2 hours. The reaction mixture was subjected to agarose gel electrophoresis and a DNA fragment of about 1.3 kb was recovered. Separately, 2 µg of pAMoPRC3Sc was dissolved in 30 µl of Y-100 buffer, 20 units of XbaI and 20 units of Asp718 were added and the digestion reaction was carried out at 37° C. for 2 hours. The reaction mixture was subjected to agarose gel electrophoresis and a DNA fragment of about 8.5 kb was recovered.

The pAMoERSA-derived XbaI-Asp718 fragment (1.3 kb; 0.05 µg) and pAMoPRC3Sc-derived XbaI-Asp718 fragment (8.5 kb; 0.1 µg) obtained in the above manner were dissolved in 30 µl of T4 ligase buffer, 175 units of T4 DNA ligase was added and the ligation reaction was carried out at 12° C. for 16 hours.

The reaction mixture was used to transform *Escherichia coli* 101 by the method of Cohen et al. and an ampicillin-resistant strain was obtained. A plasmid was isolated from this transformant strain. This plasmid was named pAMoPRSA and its structure was identified by digestion with restriction enzymes.

Figure 23:
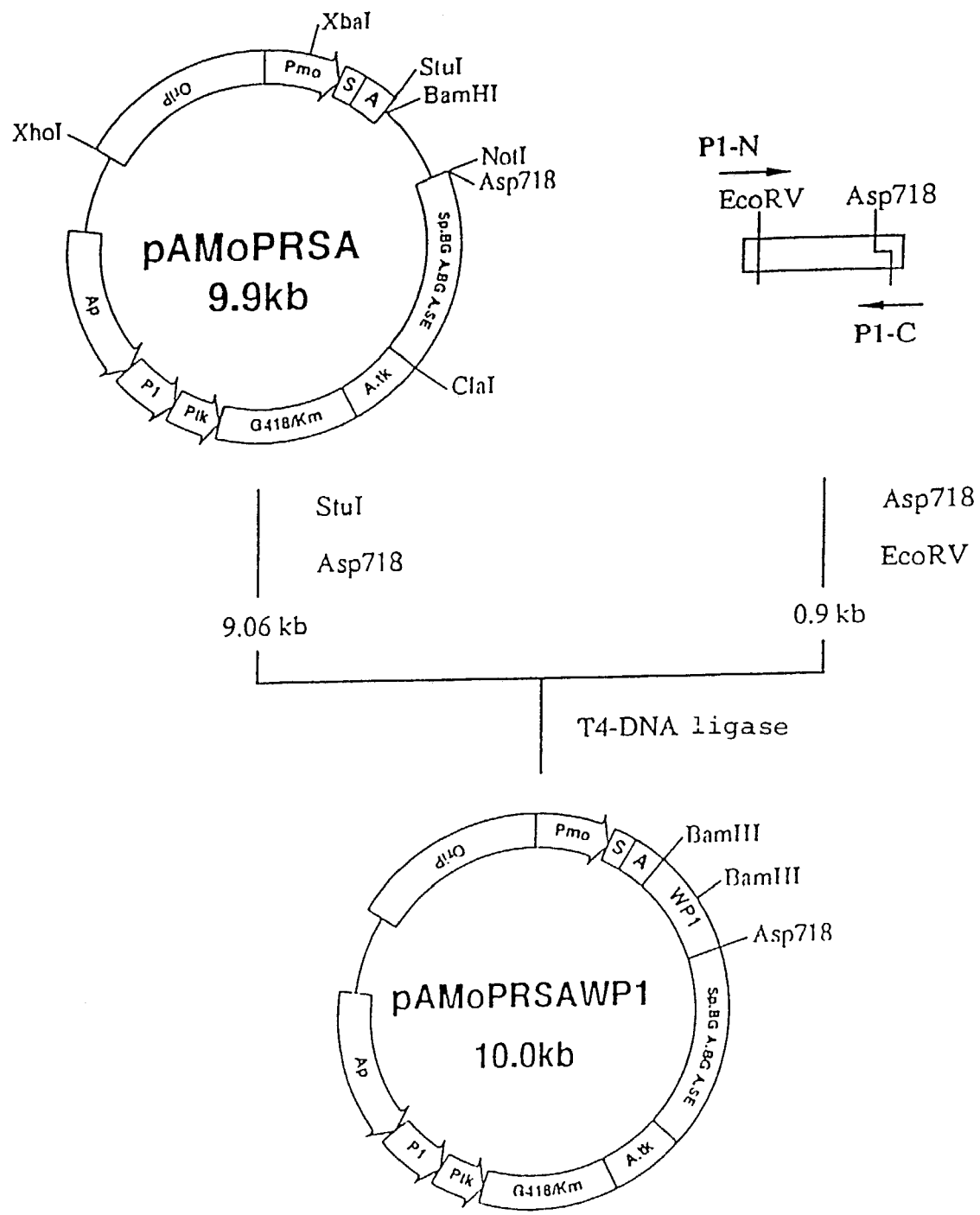
FIG. 23 shows a construction scheme for the plasmid pAMoPRSAWP1.

2. Construction of Plasmid pAMoPRSAWP1 for Secretory Production of α-2,8-sialyltransferase (cf. FIG. 23)

Based on its primary sequence, the cloned α-2,8-sialyltransferase presumably has a structure such that the N-terminal 29 amino acid residues extend into the cytoplasm, the succeeding region composed of 19 amino acid residues and rich in hydrophobicity binds to the membrane, and the remaining C terminal portion (including the site of catalysis) is exposed in the Golgi body cavity. Therefore, an attempt was made to cause secretory production of α-2,8-sialyltransferase by eliminating the N-terminal portion including the membrane binding region and, instead, adding the signal sequence of human granulocyte colony stimulating factor and the IgG binding region of protein A. DNA coding for the presumed catalytic region [from the 57th amino acid (isoleucine) residue to the 356th amino acid (serine) residue in SEQ ID NO:1] was prepared by the PCR method and inserted into the secretory expression vector pAMoPRSA construct ed in the above manner.

The following two synthetic DNAs [P1-N (36 mer) and P1-C (37 mer)] were synthesized, for use as primers for PCR, using an Applied Biosystems model 380A DNA synthesizer.

```
P1-N (36 mer)
5' - CTCTCGGATATCCGATCGTGCAGGGGGTGCTGCAAC -
3'

P1-C (37 mer)
5' - GTCAACGGTACCTTCCTAGGAAGTGGGCTGGAGTGAG -
3'
```

Since P1-N (36 mer; SEQ ID NO:6) is designed for introduction of an EcoRV site and P1-C (37 mer; SEQ ID NO:7) for introduction of an A 718 site, the DNA fragment amplified by PCR can be inserted, after cleavage with EcoRV and Asp718, into pAMoPRSA between the StuI site and Asp718 site. The PCR was carried out using Takara Shuzo's kit (GeneAmp™ DNA Amplification Reagent Kit with AmpliTaq™ Recombinant Taq DNA Polymerase). The reaction solution was prepared as described in the manual attached to the kit and the reaction steps (94° C., 1 minute; 65° C., 1 minute; and 72° C., 3 minutes) were repeated (20 cycles) using Perkin Elmer Cetus' DNA Thermal Cycler (distributed by Takara Shuzo) and then the reaction was further conducted at 72° C. for 7 minutes. The plasmid pUC119-WP1R (70 ng) was used as the template. After completion of the reaction, chloroform extraction and ethanol precipitation were performed. The precipitate was dissolved in 30 µl of Y-80 buffer, 20 units of Asp718 was added and the digestion reaction was carried out at 37° C. for 2 hours. Then, sodium chloride was added to a concentration of 150 mM, 20 units of EcoRV was added and the digestion reaction was carried out at 37° C. for 2 hours. The reaction mixture was subjected to agarose gel electrophoresis and a DNA fragment of about 0.9 kb was recovered.

Separately, 2 µg of pAMoPRSA was dissolved in 30 µl of Y-100 buffer, 20 units of StuI and 20 units of Asp718 were added and the digestion reaction was carried out at 37° C. for 2 hours. The reaction mixture was subjected to agarose gel electrophoresis and a DNA fragment of about 9.06 kb was recovered.

The EcoRV-Asp718 fragment (0.9 kb; 0.1 µg) derived from the PCR-amplified DNA and the pAMoPRSA-derived StuI-Asp718 fragment (9.06 kb; 0.1 µg) obtained as described above were dissolved in 30 µl of T4 ligase buffer, 175 units of T4 DNA ligase was added and the ligation reaction was carried out at 12° C. for 16 hours. The reaction mixture was used to transform *Escherichia coli* HB101 by the method of Cohen et al. and an ampicillin-resistant strain was obtained. A plasmid was isolated from this transformant strain by a known method. This plasmid was named pAMoPRSAWP1 and its structure was identified by digesting with restriction enzymes.

3. Secretory Production of α-2,8-sialyltransferase Using Namalwa KJM-1 Cells as Host The plasmids pAMoPRSA (secretory expression vector) and pAMoPRSAWP1 (plasmid for secretory expression of α-2,8-sialyltransferase) obtained as described above were prepared using Qiagen's plasmid preparation kit>plasmid<maxi kit (article number 41031). The plasmids prepared were dissolved in TE buffer to a concentration of 1 µg/µl. Each plasmid was then introduced into Namalwa KJM-1 cells by electroporation [Miyaji et al.: Cytotechnology, 3, 133 (1990)]. After introduction of 4 µg of plasmid per 1.6×10⁶ cells, the cells were suspended in 8 ml of RPMI1640-ITPSGF medium and cultured in a carbon dioxide gas incubator at 37° C. for 24 hours. Then, G418 (Gibco) was added to a concentration of 0.5 mg/ml and incubation was continued for 7 days. Then, 22 ml of RPMI1640-

ITPSGF medium (containing 0.5 mg/ml of G418) was added and incubation was further continued for 5 days. The thus-obtained transformants were suspended in 30 ml of RPMI1640-ITPSGF medium containing 0.5 mg/ml of G418 to a concentration of $5 \times 10^4$ cells/ml and cultured in a carbon dioxide gas incubator at 37° C. for 8 days. Then, cells were removed by centrifugation (160×g, 10 minutes) and the supernatant was recovered and again subjected to centrifugation (1,500×g, 10 minutes), followed by recovery of the supernatant. The thus-obtained culture supernatant was stored at −80° C. until use.

Figure 24:
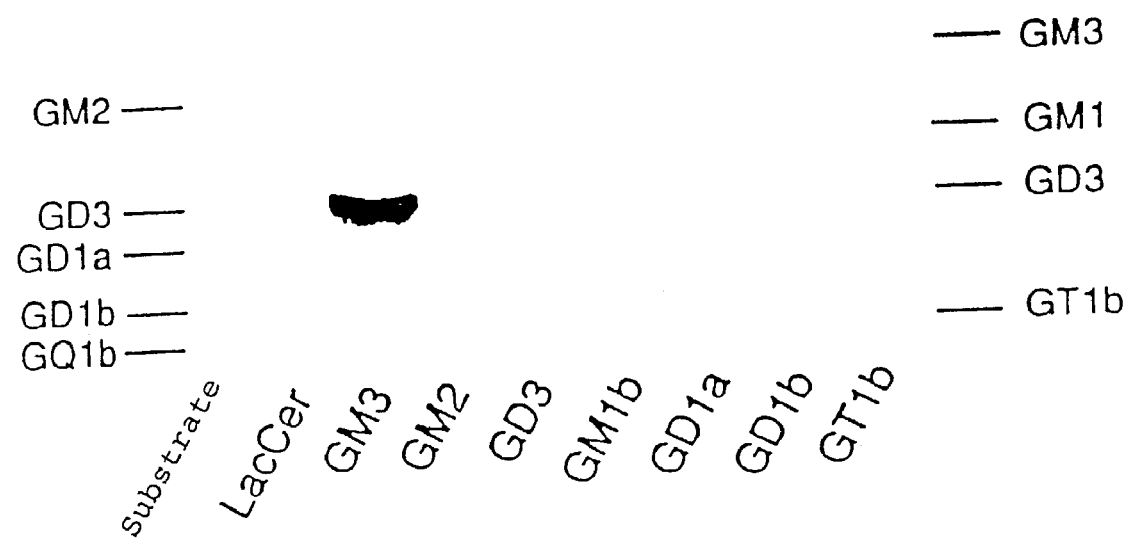
FIG. 24 shows the results of the measurement of sialyltransferase activity of the α-2,8-sialyltransferase, using various glycolipids as substrates, which has purified from a culture supernatant of Namalwa cells having plasmid pAMoPRSAWP1 introduced therein using IgG-sepharose. The results are shown as an analytic pattern obtained by applying a HPTLC plate following HPTLC treatment to a model BAS2000 bioimaging analyzer (Fujix).

The α-2,8-sialyltransferase encoded by the plasmid pAMoPRSAWP1 is expressed in the secretory manner in the form of a protein fused to the IgG binding region of protein A and therefore can be readily purified using IgG-Sepharose. Thus, sodium azide was added to the culture supernatant obtained in the above manner to a final concentration of 0.1%, 15 µl of IgG-Sepharose (Pharmacia) pretreated as described in the product manual was added and the mixture was gently stirred overnight at 4° C. The IgG-Sepharose was then recovered by centrifugation (160×g, 10 minutes), washed with three 1-ml portions of phosphate-buffered saline [PBS; 8 g/ml sodium chloride, 0.2 g/l potassium chloride, 1.15 g/l disodium hydrogen phosphate (anhydrous), 0.2 g/l potassium dihydrogen phosphate, 0.1% sodium azide] and suspended in 20 µl of RPMI1640 medium (serum-free). Using this IgG-Sepharose suspension, the GD3 synthetase activity was determined by the conventional method [Samuelson: Methods in Enzymology, 138, 567; Basu et al.: Methods in Enzymology, 138, 575]. After carrying out the reaction in 10 µl of an assay mixture [0.1 M cacodylic acid-hydrochloric acid (pH 6.0), 20 mM manganese chloride, 1% Triton, 120 µM CMP-[$^{14}$C] sialic acid (Amersham), 10 µg substrate glycolipid, IgG-Sepharose suspension mentioned above (5 µl)] at 37° C. for 4 hours, 200 µl of PBS was added and the resulting mixture was applied to a C-18 column (100 mg; Whatman). After washing with 3 ml of water, the glycolipid adsorbed on the column was eluted with 1 ml of methanol and 1 ml of chloroform-methanol (1:1) and the solvent was distilled off using gaseous nitrogen. The glycolipid was then dissolved in 10 µl of chloroform and subjected to high-performance thin layer chromatography (hereinafter, "HPTLC") using chloroform-methanol-potassium chloride (55:45:10) as the developing solvent system. The HPTLC plate after chromatography was analyzed using a model BAS2000 bioimaging analyzer (Fujix) for identification and quantitation of the radiolabeled product. The substrates used were lactosylceramide (hereinafter, "LacCer") and the gangliosides GM3, GM2, GM1b, GD3, GD1a, GD1b and GT1b. GM3 and GD3 were prepared by the conventional method [Hanai et al.: Journal of Biological Chemistry, 263, 10915–10921 (1988); Hanai et al.: Anticancer Research, 10, 1579–1586 (1990)]. LacCer, GM2, GM1b, GD1a and GD1b were purchased from Sigma. GT1b was purchased from Biosynth AG. Product identification was performed by comparing the position after development with those of standard glycolipids. The standard glycolipids were detected using orcinol-sulfuric acid. The results thus obtained are shown in FIG. 24. When the IgG-Sepharose treated by mixing with the culture supernatant derived from Namalwa cells harboring pAMoPRSAWP1 introduced therein was used, GD3 synthetase activity (activity catalyzing the synthesis of GD3 from GM3) was detected (the secretory enzyme produced in 1 ml of medium caused production of 0.1 picomole of GD3 per hour), while no such activity was detected when the IgG-Sepharose derived from the culture supernatant of Namalwa cells harboring the vector pAMoPRSA introduced therein was used. Furthermore, it was revealed that since any other glycolipid than GM3 did not serve as a substrate of the sialyltransferase encoded by pAMoPRSAWP1, the sialyltransferase is α-2,8-sialyltransferase (GD3 synthetase) having high substrate specificity to GM3 (FIG. 24).

The results described above indicate that the α-2,8-sialyltransferase of the present invention can be produced in the culture supernatant fused with the IgG binding region of *Staphylococcus aureus* protein A and that the secretion product can be readily recovered and purified using IgG-Sepharose.

INDUSTRIAL APPLICABILITY

As described in detail hereinabove, the present invention provides α-2,8-sialyltransferase which is useful, for example, in the production of carbohydrate chains having a useful physiological activity, for example the ganglioside GD3, and modifications thereof.

What is claimed is:

1. An isolated DNA coding for α-2,8-sialyltransferase, said α-2,8-sialyltransferase comprising an amino acid sequence encoded by (a) a DNA comprising the nucleotide sequence defined in SEQ ID NO:1; or (b) a DNA which hybridizes with the DNA consisting of the nucleotide sequence defined in SEQ ID NO:1 under conditions which comprises performing hybridization at 65° C. in the presence of 1.0M sodium chloride and then washing at 65° C. in a 0.1-fold concentrated SSC solution, and which encodes a protein having α-2,8-sialyltransferase activity.

2. An isolated DNA comprising the nucleotide sequence defined in SEQ ID NO:1.

3. A recombinant vector comprising, as an insert, a DNA sequence coding for an α-2,8-sialyltransferase comprising an amino acid sequence encoded by (a) a DNA comprising the nucleotide sequence defined in SEQ ID NO:1; or (b) a DNA which hybridizes with the DNA consisting of the nucleotide sequence defined in SEQ ID NO:1 under conditions which comprise performing hybridization at 65° C. in the presence of 1.0 M sodium chloride and then washing a 65° C. in a 0.1-fold concentrated SSC solution, and which encodes a protein having α-2,8-sialyltransferase activity.

4. A method of producing an α-2,8-sialyltransferase, which comprises cultivating cells transformed with the recombinant vector of claim 3 in a medium under conditions such that said DNA sequence is expressed and α-2,8-sialyltransferase thereby produced and accumulated in the culture and recovering the α-2,8-sialyltransferase from said culture.

5. The plasmid pUC119-WP1.

6. An isolated host cell transformed with the recombinant vector of claim 3.

7. A method of detecting the presence in a sample of a DNA sequence encoding an α-2,8-sialyltransferase which comprises contacting the sample with the DNA of claim 1 or 2 under conditions such that said encoding DNA sequence and said DNA of claim 3 or 4 can hybridize so that a complex is formed, and detecting the presence of said complex.

8. A method of detecting the presence in a sample of a DNA sequence encoding an α-2,8-sialyltransferase which comprises subjecting the sample to a polymerase chain reaction using as primers oligonucleotides selected from the nucleotide defined in SEQ ID NO:1, and detecting the presence of an amplification product.

9. A strain of *Escherichia coli* which is transformed with the recombinant vector of claim 3.

10. *Escherichia coli* JM105/pUC119-WP1R (FERM BP-4192).

11. An isolated nucleic acid sequence which encodes the amino acid sequence set forth in SEQ ID NO:2.

* * * * *